(12) United States Patent
Sleeman et al.

(10) Patent No.: US 9,951,127 B2
(45) Date of Patent: Apr. 24, 2018

(54) ANTI-ANGPTL3 ANTIBODIES AND USES THEREOF

(71) Applicant: Regeneron Pharmaceuticals, Inc., Tarrytown, NY (US)

(72) Inventors: Mark W. Sleeman, Richmond (AU); Viktoria Gusarova, Pleasantville, NY (US); Andrew J. Murphy, Croton-on-Hudson, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 127 days.

(21) Appl. No.: 14/667,121

(22) Filed: Mar. 24, 2015

(65) Prior Publication Data

US 2015/0197564 A1 Jul. 16, 2015

Related U.S. Application Data

(62) Division of application No. 13/517,662, filed on Jun. 14, 2012, now Pat. No. 9,018,356.

(60) Provisional application No. 61/578,309, filed on Dec. 21, 2011, provisional application No. 61/498,518, filed on Jun. 17, 2011.

(51) Int. Cl.
*A61K 39/395* (2006.01)
*C07K 16/22* (2006.01)
*A61K 45/06* (2006.01)
*A61K 39/00* (2006.01)

(52) U.S. Cl.
CPC .............. *C07K 16/22* (2013.01); *A61K 45/06* (2013.01); *A61K 2039/505* (2013.01); *C07K 2317/21* (2013.01); *C07K 2317/33* (2013.01); *C07K 2317/34* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 6,030,831 | A | 2/2000 | Godowski |
| 6,348,351 | B1 | 2/2002 | Fong |
| 7,267,819 | B2 | 9/2007 | Ferrara |
| 7,935,796 | B2 | 5/2011 | Lee |
| 9,322,018 | B2 * | 4/2016 | Bettencourt ....... C12N 15/1136 |
| 2008/0177045 | A1 | 7/2008 | Lee |
| 2009/0098117 | A1 | 4/2009 | Ferrara |
| 2011/0243948 | A1 | 10/2011 | Lee |
| 2011/0245096 | A1 | 10/2011 | Aggarwal |
| 2013/0064834 | A1 | 3/2013 | Sleeman |
| 2017/0233466 | A1 | 8/2017 | Gromada |
| 2017/0253666 | A1 | 9/2017 | Gusarova |
| 2017/0291937 | A1 | 10/2017 | Gromada |
| 2017/0312359 | A1 | 11/2017 | Pordy |

FOREIGN PATENT DOCUMENTS

| | | |
|---|---|---|
| CN | 101905024 | 12/2010 |
| EP | 1482041 | 12/2004 |
| JP | 2005080508 | 3/2005 |
| JP | 2010-512320 | 4/2010 |
| TW | 200846364 | 12/2008 |
| WO | WO 2003/044172 | 5/2003 |
| WO | WO 2006/098887 | 9/2006 |
| WO | WO 2008/073300 | 6/2008 |
| WO | WO 2010/111892 | 10/2010 |
| WO | WO 2011/008773 | 1/2011 |
| WO | WO 2011/085271 | 7/2011 |
| WO | WO 2012/174178 | 12/2012 |
| WO | WO 2014/194168 | 12/2014 |
| WO | WO 2015/100394 | 7/2015 |
| WO | WO 2016/011256 | 1/2016 |

OTHER PUBLICATIONS

Sonnenburg et al. GPIHBP1 stabilizes lipoprotein lipase and prevents its inhibition by angiopoietin-like 3 and angiopoietin-like 4. Journal of Lipid Research (2009), 50(12), 2421-2429.*
Yau et al. A Highly Conserved Motif within the NH2-terminal Coiled-coil Domain of Angiopoietin-like Protein 4 Confers Its Inhibitory Effects on Lipoprotein Lipase by Disrupting the Enzyme Dimerization. Journal of Biological Chemistry (2009), 284(18),1942-11952.*
Shimamura et al. Leptin and insulin down-regulate angiopoietin-like protein 3, a plasma triglyceride-increasing factor. Biochemical and Biophysical Research Communications (2004), 322(3), 1080-1085.*
Lee et al. Identification of a New Functional Domain in Angiopoietin-like 3 (ANGPTL3) and Angiopoietin-like 4 (ANGPTL4) Involved in Binding and Inhibition of Lipoprotein Lipase (LPL). Journal of Biological Chemistry (2009), 284(20), 13735-13745.*
Correia (2010) mAbs 2(3):221-232, "Stability of IgG isotypes in serum".
English translation of the opposition brief dated Mar. 13, 2015 for corresponding Ecuadorian application No. SP 2013-13085.
Lee, et al. (2009) Journal of Biological Chemistry 284:20:13735-13745, "Identification of a New Functional Domain in Angiopoietin-like 3 (ANGPTL3) and Angiopoietin-like4 (ANGPTL4) Involved in Binding and Inhibition of Lipoprotein Lipase (LPL)".

(Continued)

*Primary Examiner* — Maher M Haddad

(57) ABSTRACT

A fully human antibody or antigen-binding fragment of a human antibody that specifically binds and inhibits or interferes with at least one activity of human angiopoietin-like protein 3 (hANGPTL3) is provided. The human anti-hANGPTL3 antibodies are useful in treating diseases or disorders associated with ANGPTL3, such as hyperlipidemia, hyperlipoproteinemia and dyslipidemia, including hypertriglyceridemia, hypercholesterolemia, chylomicronemia, and so forth. Furthermore, the anti-hANGPTL3 antibodies can be administered to a subject in need thereof to prevent or treat diseases or disorders, for which abnormal lipid metabolism is a risk factor. Such diseases or disorders include cardiovascular diseases, such as atherosclerosis and coronary artery diseases; acute pancreatitis; nonalcoholic steatohepatitis (NASH); diabetes; obesity; and the like.

5 Claims, 2 Drawing Sheets

(56) References Cited

OTHER PUBLICATIONS

Ono, et al. (2003) Journal of Biological Chemistry, The American Society of Biological Chemists, Inc. 278(43):41804-41809, "Protein Region Important for Regulation of Lipid Metabolism in Angiopoietin-like 3 (ANGTPL3): ANGPTL3 Is Cleaved and Activated In Vivo".
Yau, et al. (2009) J. Biol. Chem. 284:11942-11952, "A Highly Conserved Motif within the NH2-terminal Coiled-coil Domain of Angiopoietin-like Protein 4 Confers Its Inhibitory Effects on Lipoprotein Lipase by Disrupting the Enzyme Dimerization."
Ando et al., (2003) J. Lipid. Res 44(6):1216-1223, "A decreased expression of angiopoietin-like 3 is protective against atherosclerosis in apoE-deficient mice".
Camenisch et al. (2002) J. Biol. Chem. 277(19):17281-17290, "ANGPTL3 Stimulates Endothelial Cell Adhesion and Migration via Integrin alpha v beta 3 and induces Blood Vessel Formation in Vivo".
Conklin et al. (1999) Genomics 62(3):477-482, "Identification of a Mammalian Angiopoietin-Related Protein Expressed Specifically in Liver".
Koishi et al., (2002) Nat. Genet. 30(2):151-157, "Angptl3 regulates lipid metabolism in mice".
Rossetti and Goldberg (2002) Nat. Med. 8(2):112-114, "A new piece in the diabetes puzzle".
Shimizugawa et al., (2002) J. Biol. Chem. 277(37):33742-33748, "ANGPTL3 Decreases Very Low Density Lipoprotein Triglyceride Clearance by Inhibition of Lipoprotein Lipase".
International Search Report dated Aug. 23, 2012 for Corresponding International Application No. PCT/US2012/042338.
Borodovsky et al. (2014) Alnylam Pharmaceuticals "Developments of Monthly to Quarterly Subcutaneous Administration of RNAi Therapeutics Targeting the Metabolic Disease Genes PCSK9, ApoC3 and ANGPTL3 ALN-PCS Phase I Study Results" Website [Online] Available Website: www.alnylam.com/web/assets/Cardiometaboliclike_AHA_Poster_111714.pdf; Last Update: unknown; Accessed on: May 9, 2017.
Gaudet (2016) Journal of Clinical Lipidology 10(3):715 "Safety and Efficacy of Evinacumab, a monoclonal antibody to ANGPTL3, in Patients with Homozygous Familial Hypercholesterolemia Receiving Concomitant Lipid-Lowering Therapies".
Gaudet (2017) Journal of Clinical Lipidology 11(3): 837-838 "Safety and Efficacy of Evinacumab, A Monoclonal Antibody to ANGPTL3, in Homozygous Familial Hypercholesterolemia".
Gusarova (2015) Journal of Lipid Research 56(7):1308-1317 "ANGPTL3 Blockade with a Human Monoclonal Antibody Reduces Plasma Lipids in Dyslipidemic Mice and Monkeys".
Hanson (2016) Molecular Genetics and Metabolism Academic Press 118(2):128-137 "The ARG59Trp Variant in ANGPTL8 (betatrophin) is Associated with Total and HDL-Cholesterol in American Indians and Mexican Americans and Differentially Affects Cleavage of ANGPTL3".
Kühnast et al. (2014) J Lipid Res. 55(10):2103-2112 "Alirocumab inhibits atherosclerosis, improves the plaque morphology, and enhances the effects of a statin".
Rader et al. (2015) Cell Metabolism 23(3): 405-412 "New Therapeutic Approaches to the Treatment of Dyslipidemia".
Tikka et al. (2016) Endocrine 52(2):187-193 "The Role of ANGPTL3 in Controlling Lipoprotein Metabolism".
Wang (2015) Journal of Lipid Research 56(7):1296-1307 "Inactivation of ANGPTL3 Reduces Hepatic VLDL-Triglyceride Secretion".
Zhang (2016) Open Biology 6(4):150727 "The ANGPTL3-4-7 Model, a Molecular Mechanism for Triglyceride Trafficking".

\* cited by examiner

| NP_055310 # | 3 3 0 | 3 3 1 | 3 3 2 | 3 3 3 | 3 3 4 | 3 3 5 | 3 3 6 | 3 3 7 | 3 3 8 | 3 3 9 | 3 4 0 | 3 4 1 | 3 4 2 | 3 4 3 | 3 4 4 | 3 4 5 | 3 4 6 | 3 4 7 | 3 4 8 | 3 4 9 | 3 5 0 | 3 5 1 | 3 5 2 | 3 5 3 | 3 5 4 | 3 5 5 | 3 5 6 | 3 5 7 | 3 5 8 | 3 5 9 | 3 6 0 | 3 6 1 | 3 6 2 | 3 6 3 | 3 6 4 | 3 6 5 | 3 6 6 | 3 6 7 | 3 6 8 | 3 6 9 | 3 7 0 |
|---|---|---|---|---|---|---|---|---|---|---|---|---|---|---|---|---|---|---|---|---|---|---|---|---|---|---|---|---|---|---|---|---|---|---|---|---|---|---|---|---|---|
| ANGPTL3 | S | P | E | P | K | S | R | F | A | M | L | D | D | V | K | I | L | A | N | G | L | L | Q | L | G | H | G | L | K | D | F | V | H | K | T | K | G | Q | I | N | D |
| Peptide 1 | | | | | | | R | F | A | S | W | D | E | M | N | V | L | A | H | G | L | Q | L | G | Q | G | L | R | E | H | A | E | R | T | R | S | Q | L | | |
| Peptide 2 | | | | | | | R | F | A | M | L | D | D | V | K | I | L | A | N | G | L | Q | L | G | H | G | L | K | D | F | V | H | K | T | K | G | Q | I | | |
| Peptide 3 | E | P | | K | S | | R | F | A | M | L | D | D | V | K | I | L | A | N | G | L | L | Q | L | G | H | G | L | | | | | | | | | | | | | |

Fig. 1

SEQUENCE LISTING

```
<160> NUMBER OF SEQ ID NOS: 194

<210> SEQ ID NO 1
<211> LENGTH: 369
<212> TYPE: DNA
<213> ORGANISM: Artificial Sequence
<220> FEATURE:
<223> OTHER INFORMATION: Synthetic

<400> SEQUENCE: 1
caggtgcagc tggtggagtc tgggggaggc gtggtccagc ctgggaggtc cctgagactc      60
tcctgtgcag cctctggatt caccttcagt agttatggca tgcactgggt ccgccaggct     120
ccaggcaagg ggctggagtg ggtggcagtt atatcatatg atggaagtaa taaatactat     180
gcagactccg tgaagggccg attcaccatt tccagagaca attccaagaa cacgctgtat     240
ctgcaaatga acagcctgag agctgaggac acggctgtgt attactgtgc gaaagtggga     300
```

```
gctactactt tctactacta ctacggtatg gacgtctggg gccaagggac cacggtcacc    360
gtctcctca                                                            369
```

<210> SEQ ID NO 2
<211> LENGTH: 123
<212> TYPE: PRT
<213> ORGANISM: Artificial Sequence
<220> FEATURE:
<223> OTHER INFORMATION: Synthetic

<400> SEQUENCE: 2

```
Gln Val Gln Leu Val Glu Ser Gly Gly Val Val Gln Pro Gly Arg
  1               5                  10                  15

Ser Leu Arg Leu Ser Cys Ala Ala Ser Gly Phe Thr Phe Ser Ser Tyr
             20                  25                  30

Gly Met His Trp Val Arg Gln Ala Pro Gly Lys Gly Leu Glu Trp Val
         35                  40                  45

Ala Val Ile Ser Tyr Asp Gly Ser Asn Lys Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Val Gly Ala Thr Thr Phe Tyr Tyr Tyr Gly Met Asp Val
            100                 105                 110

Trp Gly Gln Gly Thr Thr Val Thr Val Ser Ser
        115                 120
```

<210> SEQ ID NO 3
<211> LENGTH: 24
<212> TYPE: DNA
<213> ORGANISM: Artificial Sequence
<220> FEATURE:
<223> OTHER INFORMATION: Synthetic

<400> SEQUENCE: 3

```
ggattcacct tcagtagtta tggc                                           24
```

<210> SEQ ID NO 4
<211> LENGTH: 8
<212> TYPE: PRT
<213> ORGANISM: Artificial Sequence
<220> FEATURE:
<223> OTHER INFORMATION: Synthetic

<400> SEQUENCE: 4

```
Gly Phe Thr Phe Ser Ser Tyr Gly
  1               5
```

<210> SEQ ID NO 5
<211> LENGTH: 24
<212> TYPE: DNA
<213> ORGANISM: Artificial Sequence
<220> FEATURE:
<223> OTHER INFORMATION: Synthetic

<400> SEQUENCE: 5

```
atatcatatg atggaagtaa taaa                                           24
```

<210> SEQ ID NO 6
<211> LENGTH: 8
<212> TYPE: PRT

<210> SEQ ID NO 6
<211> LENGTH: 7
<212> TYPE: PRT
<213> ORGANISM: Artificial Sequence
<220> FEATURE:
<223> OTHER INFORMATION: Synthetic

<400> SEQUENCE: 6

Ile Ser Tyr Asp Gly Ser Asn Lys
1               5

<210> SEQ ID NO 7
<211> LENGTH: 48
<212> TYPE: DNA
<213> ORGANISM: Artificial Sequence
<220> FEATURE:
<223> OTHER INFORMATION: Synthetic

<400> SEQUENCE: 7
gcgaaagtgg gagctactac tttctactac tactacggta tggacgtc         48

<210> SEQ ID NO 8
<211> LENGTH: 16
<212> TYPE: PRT
<213> ORGANISM: Artificial Sequence
<220> FEATURE:
<223> OTHER INFORMATION: Synthetic

<400> SEQUENCE: 8

Ala Lys Val Gly Ala Thr Thr Phe Tyr Tyr Tyr Tyr Gly Met Asp Val
1               5                   10                  15

<210> SEQ ID NO 9
<211> LENGTH: 321
<212> TYPE: DNA
<213> ORGANISM: Artificial Sequence
<220> FEATURE:
<223> OTHER INFORMATION: Synthetic

<400> SEQUENCE: 9
gacatccaga tgacccagtc tccatcttcc gtgtctgcat ttgtaggaga cagagtcacc      60
atcacttgtc gggcgagtca gggtattagc agctggttag cctggtatca gcagaaacca     120
gggaaagccc ctaagctcct gatctatgct gcatccagtt tgcaaagtgg ggtcccatca     180
aggttcagcg gcagtggatc tgggacagat ttcactctca ccatcagcag cctgcagcct     240
gaagattttg caacttacta ttgtcaaaag gctaacagtt tcccattcac tttcggccct     300
gggaccaaag tggatatcaa a                                                321

<210> SEQ ID NO 10
<211> LENGTH: 107
<212> TYPE: PRT
<213> ORGANISM: Artificial Sequence
<220> FEATURE:
<223> OTHER INFORMATION: Synthetic

<400> SEQUENCE: 10

Asp Ile Gln Met Thr Gln Ser Pro Ser Ser Val Ser Ala Phe Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Lys Ala Asn Ser Phe Pro Phe
                85                  90                  95

Thr Phe Gly Pro Gly Thr Lys Val Glu Ile Lys
            100                 105

<210> SEQ ID NO 11
<211> LENGTH: 18
<212> TYPE: DNA
<213> ORGANISM: Artificial Sequence
<220> FEATURE:
<223> OTHER INFORMATION: Synthetic

<400> SEQUENCE: 11
cagggtatta gcagctgg                                                       18

<210> SEQ ID NO 12
<211> LENGTH: 6
<212> TYPE: PRT
<213> ORGANISM: Artificial Sequence
<220> FEATURE:
<223> OTHER INFORMATION: Synthetic

<400> SEQUENCE: 12

Gln Gly Ile Ser Ser Trp
 1               5

<210> SEQ ID NO 13
<211> LENGTH: 9
<212> TYPE: DNA
<213> ORGANISM: Artificial Sequence
<220> FEATURE:
<223> OTHER INFORMATION: Synthetic

<400> SEQUENCE: 13 gctgcatcc                                                                  9

<210> SEQ ID NO 14
<211> LENGTH: 3
<212> TYPE: PRT
<213> ORGANISM: Artificial Sequence
<220> FEATURE:
<223> OTHER INFORMATION: Synthetic

<400> SEQUENCE: 14

Ala Ala Ser
 1

<210> SEQ ID NO 15
<211> LENGTH: 27
<212> TYPE: DNA
<213> ORGANISM: Artificial Sequence
<220> FEATURE:
<223> OTHER INFORMATION: Synthetic

<400> SEQUENCE: 15
caaaaggcta acagtttccc attcact                                             27

<210> SEQ ID NO 16
<211> LENGTH: 9
<212> TYPE: PRT
<213> ORGANISM: Artificial Sequence
<220> FEATURE:
<223> OTHER INFORMATION: Synthetic

<400> SEQUENCE: 16

Gln Lys Ala Asn Ser Phe Pro Phe Thr
1               5

<210> SEQ ID NO 17
<211> LENGTH: 369
<212> TYPE: DNA
<213> ORGANISM: Artificial Sequence
<220> FEATURE:
<223> OTHER INFORMATION: Synthetic

<400> SEQUENCE: 17

```
caggtgcagc tggtggagtc tgggggaggc gtggtccagc ctgggaggtc cctgagactc      60
tcctgtgcag cctctggatt caccttcagt agctatggca tgcactgggt ccgccaggct     120
ccaggcaagg ggctggagtg ggtggcagtt atatcaaatg atggaagtaa taaatactat     180
gtagattccg tgaagggccg attcaccatg gcagagaca attccaagaa cacgctgtat      240
ctccaaatga acagcctgag agttgaggac acggctgtgt attactgtgc gaaaggggct     300
ggaactcttt actactacta ctacggtatg gacgtctggg gccaagggac cacggtcacc     360
gtctcctca                                                             369
```

<210> SEQ ID NO 18
<211> LENGTH: 123
<212> TYPE: PRT
<213> ORGANISM: Artificial Sequence
<220> FEATURE:
<223> OTHER INFORMATION: Synthetic

<400> SEQUENCE: 18

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Asn Asp Gly Ser Asn Lys Tyr Tyr Val Asp Ser Val
    50                  55                  60

Lys Gly Arg Phe Thr Met Gly Arg Asp Asn Ser Lys Asn Thr Leu Tyr
65                  70                  75                  80

Leu Gln Met Asn Ser Leu Arg Val Glu Asp Thr Ala Val Tyr Tyr Cys
                85                  90                  95

Ala Lys Gly Ala Gly Thr Leu Tyr Tyr Tyr Tyr Gly Met Asp Val
            100                 105                 110

Trp Gly Gln Gly Thr Thr Val Thr Val Ser Ser
        115                 120

<210> SEQ ID NO 19
<211> LENGTH: 24
<212> TYPE: DNA
<213> ORGANISM: Artificial Sequence
<220> FEATURE:
<223> OTHER INFORMATION: Synthetic

<400> SEQUENCE: 19

```
ggattcacct tcagtagcta tggc                                             24
```

<210> SEQ ID NO 20
<211> LENGTH: 8
<212> TYPE: PRT

```
<213> ORGANISM: Artificial Sequence
<220> FEATURE:
<223> OTHER INFORMATION: Synthetic

<400> SEQUENCE: 20

Gly Phe Thr Phe Ser Ser Tyr Gly
 1               5

<210> SEQ ID NO 21
<211> LENGTH: 24
<212> TYPE: DNA
<213> ORGANISM: Artificial Sequence
<220> FEATURE:
<223> OTHER INFORMATION: Synthetic

<400> SEQUENCE: 21
atatcaaatg atggaagtaa taaa                                          24

<210> SEQ ID NO 22
<211> LENGTH: 8
<212> TYPE: PRT
<213> ORGANISM: Artificial Sequence
<220> FEATURE:
<223> OTHER INFORMATION: Synthetic

<400> SEQUENCE: 22

Ile Ser Asn Asp Gly Ser Asn Lys
 1               5

<210> SEQ ID NO 23
<211> LENGTH: 48
<212> TYPE: DNA
<213> ORGANISM: Artificial Sequence
<220> FEATURE:
<223> OTHER INFORMATION: Synthetic

<400> SEQUENCE: 23
gcgaaagggg ctggaactct ttactactac tactacggta tggacgtc               48

<210> SEQ ID NO 24
<211> LENGTH: 16
<212> TYPE: PRT
<213> ORGANISM: Artificial Sequence
<220> FEATURE:
<223> OTHER INFORMATION: Synthetic

<400> SEQUENCE: 24

Ala Lys Gly Ala Gly Thr Leu Tyr Tyr Tyr Tyr Tyr Gly Met Asp Val
 1               5                  10                  15

<210> SEQ ID NO 25
<211> LENGTH: 321
<212> TYPE: DNA
<213> ORGANISM: Artificial Sequence
<220> FEATURE:
<223> OTHER INFORMATION: Synthetic

<400> SEQUENCE: 25
gacatccaga tgacccagtc tccttccacc ctgtctgcat ctgtaggaaa cagagtcacc    60
atcacttgcc gggccagtca agtattagt agctggttgg cctggtatca acaaaaacca   120
gggaaagccc ctaagttcct gatctataag gcgtctagtt tagaaagtgg ggtcccatca   180
aggttcagcg gcagtggatc tgggacagaa ttcactctca ccatcaccag cctgcagcct   240
gatgattttg caactattta ctgccaacag tacaatattt attcgtggac gttcggccaa   300
```

```
gggaccaagg tggaaatcaa a                                              321
```

<210> SEQ ID NO 26
<211> LENGTH: 107
<212> TYPE: PRT
<213> ORGANISM: Artificial Sequence
<220> FEATURE:
<223> OTHER INFORMATION: Synthetic

<400> SEQUENCE: 26

```
Asp Ile Gln Met Thr Gln Ser Pro Ser Thr Leu Ser Ala Ser Val Gly
  1               5                  10                  15

Asn Arg Val Thr Ile Thr Cys Arg Ala Ser Gln Ser Ile Ser Ser Trp
             20                  25                  30

Leu Ala Trp Tyr Gln Gln Lys Pro Gly Lys Ala Pro Lys Phe Leu Ile
         35                  40                  45

Tyr Lys Ala Ser Ser Leu Glu Ser Gly Val Pro Ser Arg Phe Ser Gly
     50                  55                  60

Ser Gly Ser Gly Thr Glu Phe Thr Leu Thr Ile Thr Ser Leu Gln Pro
 65                  70                  75                  80

Asp Asp Phe Ala Thr Tyr Tyr Cys Gln Gln Tyr Asn Ile Tyr Ser Trp
                 85                  90                  95

Thr Phe Gly Gln Gly Thr Lys Val Glu Ile Lys
            100                 105
```

<210> SEQ ID NO 27
<211> LENGTH: 18
<212> TYPE: DNA
<213> ORGANISM: Artificial Sequence
<220> FEATURE:
<223> OTHER INFORMATION: Synthetic

<400> SEQUENCE: 27

```
caaagtatta gtagctgg                                                   18
```

<210> SEQ ID NO 28
<211> LENGTH: 6
<212> TYPE: PRT
<213> ORGANISM: Artificial Sequence
<220> FEATURE:
<223> OTHER INFORMATION: Synthetic

<400> SEQUENCE: 28

```
Gln Ser Ile Ser Ser Trp
  1               5
```

<210> SEQ ID NO 29
<211> LENGTH: 9
<212> TYPE: DNA
<213> ORGANISM: Artificial Sequence
<220> FEATURE:
<223> OTHER INFORMATION: Synthetic

<400> SEQUENCE: 29

```
aaggcgtct                                                              9
```

<210> SEQ ID NO 30
<211> LENGTH: 3
<212> TYPE: PRT
<213> ORGANISM: Artificial Sequence
<220> FEATURE:
<223> OTHER INFORMATION: Synthetic

<400> SEQUENCE: 30

```
<210> SEQ ID NO 31
<211> LENGTH: 27
<212> TYPE: DNA
<213> ORGANISM: Artificial Sequence
<220> FEATURE:
<223> OTHER INFORMATION: Synthetic

<400> SEQUENCE: 31
caacagtaca atatttattc gtggacg                                           27

<210> SEQ ID NO 32
<211> LENGTH: 9
<212> TYPE: PRT
<213> ORGANISM: Artificial Sequence
<220> FEATURE:
<223> OTHER INFORMATION: Synthetic

<400> SEQUENCE: 32
```

Gln Gln Tyr Asn Ile Tyr Ser Trp Thr
 1               5

```
<210> SEQ ID NO 33
<211> LENGTH: 372
<212> TYPE: DNA
<213> ORGANISM: Artificial Sequence
<220> FEATURE:
<223> OTHER INFORMATION: Synthetic

<400> SEQUENCE: 33
caggtgcagc tggtggagtc tgggggaggc gtggtccagc ctgggaggtc cctgagactc        60
tcctgtgcag cctctggatt caccttcagt acctatggca tgcactgggt ccgccaggct       120
ccaggcaagg ggctggagtg gatggcagtt atatcatttg atagaggtaa taaatactat       180
gcagactccg tgaagggccg attcaccatc tccagagaca attccaagaa cacgctgtat       240
ctgcaaatga acagcctgag agctgaggac acggctgtgt attactgtgc gaaggggggg       300
ggttcgggga ctttctacta ctactacggt atggacgtct ggggccaagg gaccacggtc       360
accgtctcct ca                                                          372

<210> SEQ ID NO 34
<211> LENGTH: 124
<212> TYPE: PRT
<213> ORGANISM: Artificial Sequence
<220> FEATURE:
<223> OTHER INFORMATION: Synthetic

<400> SEQUENCE: 34
```

Gln Val Gln Leu Val Gln Ser Gly Gly Gly Val Val Gln Pro Gly Arg
 1               5                  10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Met
        35                  40                  45

Ala Val Ile Ser Phe Asp Arg Gly Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys

```
                   85                  90                  95
Ala Lys Gly Gly Gly Ser Gly Thr Phe Tyr Tyr Tyr Tyr Gly Met Asp
                100                 105                 110

Val Trp Gly Gln Gly Thr Thr Val Thr Val Ser Ser
        115                 120
```

<210> SEQ ID NO 35
<211> LENGTH: 24
<212> TYPE: DNA
<213> ORGANISM: Artificial Sequence
<220> FEATURE:
<223> OTHER INFORMATION: Synthetic

<400> SEQUENCE: 35
ggattcacct tcagtaccta tggc        24

<210> SEQ ID NO 36
<211> LENGTH: 8
<212> TYPE: PRT
<213> ORGANISM: Artificial Sequence
<220> FEATURE:
<223> OTHER INFORMATION: Synthetic

<400> SEQUENCE: 36

```
Gly Phe Thr Phe Ser Thr Tyr Gly
1               5
```

<210> SEQ ID NO 37
<211> LENGTH: 24
<212> TYPE: DNA
<213> ORGANISM: Artificial Sequence
<220> FEATURE:
<223> OTHER INFORMATION: Synthetic

<400> SEQUENCE: 37
atatcatttg atagaggtaa taaa        24

<210> SEQ ID NO 38
<211> LENGTH: 8
<212> TYPE: PRT
<213> ORGANISM: Artificial Sequence
<220> FEATURE:
<223> OTHER INFORMATION: Synthetic

<400> SEQUENCE: 38

```
Ile Ser Phe Asp Arg Gly Asn Lys
1               5
```

<210> SEQ ID NO 39
<211> LENGTH: 51
<212> TYPE: DNA
<213> ORGANISM: Artificial Sequence
<220> FEATURE:
<223> OTHER INFORMATION: Synthetic

<400> SEQUENCE: 39
gcgaaagggg ggggttcggg gactttctac tactactacg gtatggacgt c        51

<210> SEQ ID NO 40
<211> LENGTH: 17
<212> TYPE: PRT
<213> ORGANISM: Artificial Sequence
<220> FEATURE:
<223> OTHER INFORMATION: Synthetic

<400> SEQUENCE: 40

Ala Lys Gly Gly Gly Ser Gly Thr Phe Tyr Tyr Tyr Gly Met Asp
1               5                   10                  15

Val

<210> SEQ ID NO 41
<211> LENGTH: 324
<212> TYPE: DNA
<213> ORGANISM: Artificial Sequence
<220> FEATURE:
<223> OTHER INFORMATION: Synthetic

<400> SEQUENCE: 41
gacatccaga tgacccagtc tccatcttcc gtgtctgcat ctgtaggaaa cagagtcacc    60
atcacttgtc gggcgagtca gggtattagc agctggttag cctggtatca ccagaaacca   120
gggaaagtcc ctaaggtcct gatctatgct gcatccagtt tgcaaagtgg ggtcccatca   180
aggttcagcg gcagtggatc tgggacagat tcactctcac ccatcagcag cctgcagcct   240
gaagattttg caacttacta ttgtcaacag gctaacagtt ccccattcac tttcggccct   300
gggaccaaag tggatatcaa acga                                          324

<210> SEQ ID NO 42
<211> LENGTH: 108
<212> TYPE: PRT
<213> ORGANISM: Artificial Sequence
<220> FEATURE:
<223> OTHER INFORMATION: Synthetic

<400> SEQUENCE: 42

Asp Ile Gln Met Thr Gln Ser Pro Ser Ser Val Ser Ala Ser Val Gly
1               5                   10                  15

Asn Arg Val Thr Ile Thr Cys Arg Ala Ser Gln Gly Ile Ser Ser Trp
            20                  25                  30

Leu Ala Trp Tyr His Gln Lys Pro Gly Lys Val Pro Lys Val Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Phe
                85                  90                  95

Thr Phe Gly Pro Gly Thr Lys Val Glu Ile Lys Arg
            100                 105

<210> SEQ ID NO 43
<211> LENGTH: 18
<212> TYPE: DNA
<213> ORGANISM: Artificial Sequence
<220> FEATURE:
<223> OTHER INFORMATION: Synthetic

<400> SEQUENCE: 43
cagggtatta gcagctgg                                                  18

<210> SEQ ID NO 44
<211> LENGTH: 6
<212> TYPE: PRT
<213> ORGANISM: Artificial Sequence
<220> FEATURE:
<223> OTHER INFORMATION: Synthetic -continued

<400> SEQUENCE: 44

Gln Gly Ile Ser Ser Trp
 1               5

<210> SEQ ID NO 45
<211> LENGTH: 9
<212> TYPE: DNA
<213> ORGANISM: Artificial Sequence
<220> FEATURE:
<223> OTHER INFORMATION: Synthetic

<400> SEQUENCE: 45 gctgcatcc                                                                 9

<210> SEQ ID NO 46
<211> LENGTH: 3
<212> TYPE: PRT
<213> ORGANISM: Artificial Sequence
<220> FEATURE:
<223> OTHER INFORMATION: Synthetic

<400> SEQUENCE: 46

Ala Ala Ser
 1

<210> SEQ ID NO 47
<211> LENGTH: 27
<212> TYPE: DNA
<213> ORGANISM: Artificial Sequence
<220> FEATURE:
<223> OTHER INFORMATION: Synthetic

<400> SEQUENCE: 47
caacaggcta acagtttccc attcact                                            27

<210> SEQ ID NO 48
<211> LENGTH: 9
<212> TYPE: PRT
<213> ORGANISM: Artificial Sequence
<220> FEATURE:
<223> OTHER INFORMATION: Synthetic

<400> SEQUENCE: 48

Gln Gln Ala Asn Ser Phe Pro Phe Thr
 1               5

<210> SEQ ID NO 49
<211> LENGTH: 375
<212> TYPE: DNA
<213> ORGANISM: Artificial Sequence
<220> FEATURE:
<223> OTHER INFORMATION: Synthetic

<400> SEQUENCE: 49
caggtacagc tgcagcagtc aggtccagga ctggtgaaac cctcgcagac cctctcactc        60
acctgtgcca tctccgggga cagtgtctct agcaacagtc ctgcttggaa ctggatcagg       120
cagtccccat cgagaggcct tgagtggctg ggaaggacat actacaggtc caagtggtat       180
aatgattatg cagtgtctgt gagaggtcga ataaccatca cccagacac atccaataac        240 cagttctccc tacatctgaa ctctgtgact cccgaggaca cggcgatgta ttactgtgca       300
agagacaagg gtctaacagc tcgtccgacc tactttgact actggggcca gggaaccctg       360
gtcaccgtct cctca                                                        375

```
<210> SEQ ID NO 50
<211> LENGTH: 125
<212> TYPE: PRT
<213> ORGANISM: Artificial Sequence
<220> FEATURE:
<223> OTHER INFORMATION: Synthetic

<400> SEQUENCE: 50

Gln Val Gln Leu Gln Gln Ser Gly Pro Gly Leu Val Lys Pro Ser Gln
 1               5                  10                  15

Thr Leu Ser Leu Thr Cys Ala Ile Ser Gly Asp Ser Val Ser Ser Asn
            20                  25                  30

Ser Pro Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Arg Gly Arg Ile Thr Ile Asn Pro Asp Thr Ser Asn Asn
65                  70                  75                  80

Gln Phe Ser Leu His Leu Asn Ser Val Thr Pro Glu Asp Thr Ala Met
                85                  90                  95

Tyr Tyr Cys Ala Arg Asp Lys Gly Leu Thr Ala Arg Pro Thr Tyr Phe
            100                 105                 110

Asp Tyr Trp Gly Gln Gly Thr Leu Val Thr Val Ser Ser
        115                 120                 125

<210> SEQ ID NO 51
<211> LENGTH: 30
<212> TYPE: DNA
<213> ORGANISM: Artificial Sequence
<220> FEATURE:
<223> OTHER INFORMATION: Synthetic

<400> SEQUENCE: 51
ggggacagtg tctctagcaa cagtcctgct                                       30

<210> SEQ ID NO 52
<211> LENGTH: 10
<212> TYPE: PRT
<213> ORGANISM: Artificial Sequence
<220> FEATURE:
<223> OTHER INFORMATION: Synthetic

<400> SEQUENCE: 52

Gly Asp Ser Val Ser Ser Asn Ser Pro Ala
 1               5                  10

<210> SEQ ID NO 53
<211> LENGTH: 27
<212> TYPE: DNA
<213> ORGANISM: Artificial Sequence
<220> FEATURE:
<223> OTHER INFORMATION: Synthetic

<400> SEQUENCE: 53
acatactaca ggtccaagtg gtataat                                          27

<210> SEQ ID NO 54
<211> LENGTH: 9
<212> TYPE: PRT
<213> ORGANISM: Artificial Sequence
<220> FEATURE:
<223> OTHER INFORMATION: Synthetic
```

<400> SEQUENCE: 54

Thr Tyr Tyr Arg Ser Lys Trp Tyr Asn
1               5

<210> SEQ ID NO 55
<211> LENGTH: 45
<212> TYPE: DNA
<213> ORGANISM: Artificial Sequence
<220> FEATURE:
<223> OTHER INFORMATION: Synthetic

<400> SEQUENCE: 55
gcaagagaca agggtctaac agctcgtccg acctactttg actac           45

<210> SEQ ID NO 56
<211> LENGTH: 15
<212> TYPE: PRT
<213> ORGANISM: Artificial Sequence
<220> FEATURE:
<223> OTHER INFORMATION: Synthetic

<400> SEQUENCE: 56

Ala Arg Asp Lys Gly Leu Thr Ala Arg Pro Thr Tyr Phe Asp Tyr
1               5                   10                  15

<210> SEQ ID NO 57
<211> LENGTH: 326
<212> TYPE: DNA
<213> ORGANISM: Artificial Sequence
<220> FEATURE:
<223> OTHER INFORMATION: Synthetic

<400> SEQUENCE: 57
gacatccaga tgacccagtc tccttccacc ctgtctgcat ctgtaggaga cagagtcacc      60
atcacttgcc gggccagtca gagtattaat tactggttgg cctggtatca gcagaaacca    120
gggaaagccc ctaagcccct tatctataag gcgtctagtt tagaaagtgg ggtcccatca    180
aggttcagcg gcagtggatc tgggacagag ttcactctca ccatcagcag cctgcagcct    240
gacgatttta caacttatta ctgccaacag tataatagtt attctccgac gttcggccaa    300
gggaccaagg tggaaatcaa acgaac                                          326

<210> SEQ ID NO 58
<211> LENGTH: 108
<212> TYPE: PRT
<213> ORGANISM: Artificial Sequence
<220> FEATURE:
<223> OTHER INFORMATION: Synthetic

<400> SEQUENCE: 58

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Asn Tyr Trp
            20                  25                  30

Leu Ala Trp Tyr Gln Gln Lys Pro Gly Lys Ala Pro Lys Pro Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Thr Thr Tyr Tyr Cys Gln Gln Tyr Asn Ser Tyr Ser Pro
                85                  90                  95

Thr Phe Gly Gln Gly Thr Lys Leu Glu Ile Lys Arg
            100                 105

<210> SEQ ID NO 59
<211> LENGTH: 18
<212> TYPE: DNA
<213> ORGANISM: Artificial Sequence
<220> FEATURE:
<223> OTHER INFORMATION: Synthetic

<400> SEQUENCE: 59
cagagtatta attactgg                                                   18

<210> SEQ ID NO 60
<211> LENGTH: 6
<212> TYPE: PRT
<213> ORGANISM: Artificial Sequence
<220> FEATURE:
<223> OTHER INFORMATION: Synthetic

<400> SEQUENCE: 60

Gln Ser Ile Asn Tyr Trp
 1               5

<210> SEQ ID NO 61
<211> LENGTH: 9
<212> TYPE: DNA
<213> ORGANISM: Artificial Sequence
<220> FEATURE:
<223> OTHER INFORMATION: Synthetic

<400> SEQUENCE: 61 aaggcgtct                                                              9

<210> SEQ ID NO 62
<211> LENGTH: 3
<212> TYPE: PRT
<213> ORGANISM: Artificial Sequence
<220> FEATURE:
<223> OTHER INFORMATION: Synthetic

<400> SEQUENCE: 62

Lys Ala Ser
 1

<210> SEQ ID NO 63
<211> LENGTH: 27
<212> TYPE: DNA
<213> ORGANISM: Artificial Sequence
<220> FEATURE:
<223> OTHER INFORMATION: Synthetic

<400> SEQUENCE: 63
caacagtata atagttattc tccgacg                                          27

<210> SEQ ID NO 64
<211> LENGTH: 9
<212> TYPE: PRT
<213> ORGANISM: Artificial Sequence
<220> FEATURE:
<223> OTHER INFORMATION: Synthetic

<400> SEQUENCE: 64

Gln Gln Tyr Asn Ser Tyr Ser Pro Thr
 1               5

<210> SEQ ID NO 65
<211> LENGTH: 378
<212> TYPE: DNA
<213> ORGANISM: Artificial Sequence
<220> FEATURE:
<223> OTHER INFORMATION: Synthetic

<400> SEQUENCE: 65

```
gaggtgcagc tggtggagtc tgggggaggc gtgatacagc ctgggggtc cctgagactc      60 tcctgtgcag cctctggatt caccttcgat gattatgcca tgaactgggt ccgtcaaggt    120
ccagggaagg gtctggagtg gtctctgcc ataagtggtg atggcggtag cacatactat    180
gcagactcgg tgaagggccg attcaccatc tccagagaca acagcaaaaa ctccctgtat    240
ctgcaaatga acagtctgag agctgaggac accgccttt tttactgtgc aaaagatctc    300
cgtaatacga tttttggagt ggttattccc gatgcttttg atatctgggg ccaagggaca    360
atggtcaccg tctcttca                                                  378
```

<210> SEQ ID NO 66
<211> LENGTH: 126
<212> TYPE: PRT
<213> ORGANISM: Artificial Sequence
<220> FEATURE:
<223> OTHER INFORMATION: Synthetic

<400> SEQUENCE: 66

```
Glu Val Gln Leu Val Glu Ser Gly Gly Gly Val Ile Gln Pro Gly Gly
  1               5                  10                  15

Ser Leu Arg Leu Ser Cys Ala Ala Ser Gly Phe Thr Phe Asp Asp Tyr
             20                  25                  30

Ala Met Asn Trp Val Arg Gln Gly Pro Gly Lys Gly Leu Glu Trp Val
         35                  40                  45

Ser Ala Ile Ser Gly Asp Gly Gly Ser Thr Tyr Tyr Ala Asp Ser Val
     50                  55                  60

Lys Gly Arg Phe Thr Ile Ser Arg Asp Asn Ser Lys Asn Ser Leu Tyr
 65                  70                  75                  80

Leu Gln Met Asn Ser Leu Arg Ala Glu Asp Thr Ala Phe Phe Tyr Cys
                 85                  90                  95

Ala Lys Asp Leu Arg Asn Thr Ile Phe Gly Val Val Ile Pro Asp Ala
            100                 105                 110

Phe Asp Ile Trp Gly Gln Gly Thr Met Val Thr Val Ser Ser
        115                 120                 125
```

<210> SEQ ID NO 67
<211> LENGTH: 24
<212> TYPE: DNA
<213> ORGANISM: Artificial Sequence
<220> FEATURE:
<223> OTHER INFORMATION: Synthetic

<400> SEQUENCE: 67

```
ggattcacct tcgatgatta tgcc                                            24
```

<210> SEQ ID NO 68
<211> LENGTH: 8
<212> TYPE: PRT
<213> ORGANISM: Artificial Sequence
<220> FEATURE:
<223> OTHER INFORMATION: Synthetic

<400> SEQUENCE: 68

```
<210> SEQ ID NO 69
<211> LENGTH: 24
<212> TYPE: DNA
<213> ORGANISM: Artificial Sequence
<220> FEATURE:
<223> OTHER INFORMATION: Synthetic

<400> SEQUENCE: 69
ataagtggtg atggcggtag caca                                          24

<210> SEQ ID NO 70
<211> LENGTH: 8
<212> TYPE: PRT
<213> ORGANISM: Artificial Sequence
<220> FEATURE:
<223> OTHER INFORMATION: Synthetic

<400> SEQUENCE: 70

Ile Ser Gly Asp Gly Gly Ser Thr
 1               5

<210> SEQ ID NO 71
<211> LENGTH: 57
<212> TYPE: DNA
<213> ORGANISM: Artificial Sequence
<220> FEATURE:
<223> OTHER INFORMATION: Synthetic

<400> SEQUENCE: 71
gcaaaagatc tccgtaatac gattttgga gtggttattc ccgatgcttt tgatatc       57

<210> SEQ ID NO 72
<211> LENGTH: 19
<212> TYPE: PRT
<213> ORGANISM: Artificial Sequence
<220> FEATURE:
<223> OTHER INFORMATION: Synthetic

<400> SEQUENCE: 72

Ala Lys Asp Leu Arg Asn Thr Ile Phe Gly Val Val Ile Pro Asp Ala
 1               5                  10                  15
Phe Asp Ile

<210> SEQ ID NO 73
<211> LENGTH: 324
<212> TYPE: DNA
<213> ORGANISM: Artificial Sequence
<220> FEATURE:
<223> OTHER INFORMATION: Synthetic

<400> SEQUENCE: 73
gacatccaga tgacccagtc tccttccacc ctgtctgcat ctgtaggaga cagagtcacc    60
atcacttgcc gggccagtca gagcattagg agctggttgg cctggtatca gcagaaacca   120
gggaaagccc ctaaactcct gatctataag gcgtctagtt tagaaagtgg ggtcccatca   180
aggttcagcg gcagtggatc tgggacagaa ttcactctca ccatcagcag cctgcagcct   240
gatgattttg caacttatta ctgccaacaa tataatagtt attcgtacac ttttggccag   300
gggaccaagc tggagatcaa acga                                          324
```

Gly Phe Thr Phe Asp Asp Tyr Ala
 1               5

```
<210> SEQ ID NO 74
<211> LENGTH: 108
<212> TYPE: PRT
<213> ORGANISM: Artificial Sequence
<220> FEATURE:
<223> OTHER INFORMATION: Synthetic

<400> SEQUENCE: 74

Asp Ile Gln Met Thr Gln Ser Pro Ser Thr Leu Ser Ala Ser Val Gly
 1               5                  10                  15

Asp Arg Val Thr Ile Thr Cys Arg Ala Ser Gln Ser Ile Arg Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr Asn Ser Tyr Ser Tyr
                85                  90                  95

Thr Phe Gly Gln Gly Thr Lys Leu Glu Ile Lys Arg
                100                 105

<210> SEQ ID NO 75
<211> LENGTH: 18
<212> TYPE: DNA
<213> ORGANISM: Artificial Sequence
<220> FEATURE:
<223> OTHER INFORMATION: Synthetic

<400> SEQUENCE: 75
cagagcatta ggagctgg                                                        18

<210> SEQ ID NO 76
<211> LENGTH: 6
<212> TYPE: PRT
<213> ORGANISM: Artificial Sequence
<220> FEATURE:
<223> OTHER INFORMATION: Synthetic

<400> SEQUENCE: 76

Gln Ser Ile Arg Ser Trp
 1               5

<210> SEQ ID NO 77
<211> LENGTH: 9
<212> TYPE: DNA
<213> ORGANISM: Artificial Sequence
<220> FEATURE:
<223> OTHER INFORMATION: Synthetic

<400> SEQUENCE: 77 aaggcgtct                                                                   9

<210> SEQ ID NO 78
<211> LENGTH: 3
<212> TYPE: PRT
<213> ORGANISM: Artificial Sequence
<220> FEATURE:
<223> OTHER INFORMATION: Synthetic

<400> SEQUENCE: 78

Lys Ala Ser
 1
```

<210> SEQ ID NO 79
<211> LENGTH: 27
<212> TYPE: DNA
<213> ORGANISM: Artificial Sequence
<220> FEATURE:
<223> OTHER INFORMATION: Synthetic

<400> SEQUENCE: 79
caacaatata atagttattc gtacact                                27

<210> SEQ ID NO 80
<211> LENGTH: 9
<212> TYPE: PRT
<213> ORGANISM: Artificial Sequence
<220> FEATURE:
<223> OTHER INFORMATION: Synthetic

<400> SEQUENCE: 80

Gln Gln Tyr Asn Ser Tyr Ser Tyr Thr
 1               5

<210> SEQ ID NO 81
<211> LENGTH: 354
<212> TYPE: DNA
<213> ORGANISM: Artificial Sequence
<220> FEATURE:
<223> OTHER INFORMATION: Synthetic

<400> SEQUENCE: 81
caggtgcagc tggtggagtc gggggggaggc ttggtcaagc ctggagggtc cctgagactc     60
tcctgtgcag cctctggatt cactttcagt gactactaca tgagctggat ccgtcaggct    120
ccagggaagg ggctggagtg ggtttcatac attggtagta gtggtgtcaa catgtactac    180
gcagactctg tgaagggccg attcaccatc tccagggaca acgccaagaa ttcattatat    240
ctggaaatga acagcctgag agccgaggac acggctgttt attactgtgc gagagactct    300
tcccaactgg gttttgacta ctggggccag ggaaccctgg tcaccgtctc ctca          354

<210> SEQ ID NO 82
<211> LENGTH: 118
<212> TYPE: PRT
<213> ORGANISM: Artificial Sequence
<220> FEATURE:
<223> OTHER INFORMATION: Synthetic

<400> SEQUENCE: 82

Gln Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Gly Ser Ser Gly Val Asn Met Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Glu Met Asn Ser Leu Arg Ala Glu Asp Thr Ala Val Tyr Tyr Cys
                85                  90                  95

Ala Arg Asp Ser Ser Gln Leu Gly Phe Asp Tyr Trp Gly Gln Gly Thr
            100                 105                 110

Leu Val Thr Val Ser Ser
        115

<210> SEQ ID NO 83
<211> LENGTH: 24
<212> TYPE: DNA
<213> ORGANISM: Artificial Sequence
<220> FEATURE:
<223> OTHER INFORMATION: Synthetic

<400> SEQUENCE: 83
ggattcactt tcagtgacta ctac                                          24

<210> SEQ ID NO 84
<211> LENGTH: 8
<212> TYPE: PRT
<213> ORGANISM: Artificial Sequence
<220> FEATURE:
<223> OTHER INFORMATION: Synthetic

<400> SEQUENCE: 84

Gly Phe Thr Phe Ser Asp Tyr Tyr
1               5

<210> SEQ ID NO 85
<211> LENGTH: 24
<212> TYPE: DNA
<213> ORGANISM: Artificial Sequence
<220> FEATURE:
<223> OTHER INFORMATION: Synthetic

<400> SEQUENCE: 85
attggtagta gtggtgtcaa catg                                          24

<210> SEQ ID NO 86
<211> LENGTH: 8
<212> TYPE: PRT
<213> ORGANISM: Artificial Sequence
<220> FEATURE:
<223> OTHER INFORMATION: Synthetic

<400> SEQUENCE: 86

Ile Gly Ser Ser Gly Val Asn Met
1               5

<210> SEQ ID NO 87
<211> LENGTH: 33
<212> TYPE: DNA
<213> ORGANISM: Artificial Sequence
<220> FEATURE:
<223> OTHER INFORMATION: Synthetic

<400> SEQUENCE: 87
gcgagagact cttcccaact gggttttgac tac                                33

<210> SEQ ID NO 88
<211> LENGTH: 11
<212> TYPE: PRT
<213> ORGANISM: Artificial Sequence
<220> FEATURE:
<223> OTHER INFORMATION: Synthetic

<400> SEQUENCE: 88

Ala Arg Asp Ser Ser Gln Leu Gly Phe Asp Tyr
1               5                   10

<210> SEQ ID NO 89
<211> LENGTH: 324
<212> TYPE: DNA
<213> ORGANISM: Artificial Sequence
<220> FEATURE:
<223> OTHER INFORMATION: Synthetic

<400> SEQUENCE: 89

```
gacatccaga tgacccagtc tccatcctcc ctgtctgcat ctgtaggaga cagagtcacc      60
atcacttgcc ggacaagtca gaatattatc aactttttaa attggtatca acagaaacct     120
gggaaggccc ctaaactcct gatctatact acttccactt tacaaagtgg ggtcccatca     180
aggttcagtg gcagtggatc tgggacagat ttcactctct ccatcaatag tctacaacct     240
gaagattttg caacttactt ctgtcaacag acttacagta atccactcac tttcggcgga     300
gggaccaagg tggagatcaa acga                                             324
```

<210> SEQ ID NO 90
<211> LENGTH: 108
<212> TYPE: PRT
<213> ORGANISM: Artificial Sequence
<220> FEATURE:
<223> OTHER INFORMATION: Synthetic

<400> SEQUENCE: 90

Asp Ile Gln Met Thr Gln Ser Pro Ser Ser Leu Ser Ala Ser Val Gly
1               5                   10                  15

Asp Arg Val Thr Ile Thr Cys Arg Thr Ser Gln Asn Ile Ile Asn Phe
            20                  25                  30

Leu Asn Trp Tyr Gln Gln Lys Pro Gly Lys Ala Pro Lys Leu Leu Ile
        35                  40                  45

Tyr Thr Thr Ser Thr Leu Gln Ser Gly Val Pro Ser Arg Phe Ser Gly
    50                  55                  60

Ser Gly Ser Gly Thr Asp Phe Thr Leu Ser Ile Asn Ser Leu Gln Pro
65                  70                  75                  80

Glu Asp Phe Ala Thr Tyr Phe Cys Gln Gln Thr Tyr Ser Asn Pro Leu
                85                  90                  95

Thr Phe Gly Gly Gly Thr Lys Leu Glu Ile Lys Arg
            100                 105

<210> SEQ ID NO 91
<211> LENGTH: 18
<212> TYPE: DNA
<213> ORGANISM: Artificial Sequence
<220> FEATURE:
<223> OTHER INFORMATION: Synthetic

<400> SEQUENCE: 91

```
cagaatatta tcaactttt                                                   18
```

<210> SEQ ID NO 92
<211> LENGTH: 6
<212> TYPE: PRT
<213> ORGANISM: Artificial Sequence
<220> FEATURE:
<223> OTHER INFORMATION: Synthetic

<400> SEQUENCE: 92

Gln Asn Ile Ile Asn Phe
1               5

<210> SEQ ID NO 93

<210> SEQ ID NO 93
<211> LENGTH: 9
<212> TYPE: DNA
<213> ORGANISM: Artificial Sequence
<220> FEATURE:
<223> OTHER INFORMATION: Synthetic

<400> SEQUENCE: 93 actacttcc                                                                                      9

<210> SEQ ID NO 94
<211> LENGTH: 3
<212> TYPE: PRT
<213> ORGANISM: Artificial Sequence
<220> FEATURE:
<223> OTHER INFORMATION: Synthetic

<400> SEQUENCE: 94

Thr Thr Ser
 1

<210> SEQ ID NO 95
<211> LENGTH: 27
<212> TYPE: DNA
<213> ORGANISM: Artificial Sequence
<220> FEATURE:
<223> OTHER INFORMATION: Synthetic

<400> SEQUENCE: 95
caacagactt acagtaatcc actcact                                                                  27

<210> SEQ ID NO 96
<211> LENGTH: 9
<212> TYPE: PRT
<213> ORGANISM: Artificial Sequence
<220> FEATURE:
<223> OTHER INFORMATION: Synthetic

<400> SEQUENCE: 96

Gln Gln Thr Tyr Ser Asn Pro Leu Thr
 1               5

<210> SEQ ID NO 97
<211> LENGTH: 360
<212> TYPE: DNA
<213> ORGANISM: Artificial Sequence
<220> FEATURE:
<223> OTHER INFORMATION: Synthetic

<400> SEQUENCE: 97
gaggtgcagc tggtgcagtc tggggaggc gtggtccagc ctggaggtc cctgagactc         60 tcctgtgcag cgtctggatt caccttcagt aattatggca tgcactgggt ccgccaggct      120
ccaggcaagg ggctggagtg ggtggcagtt gtttggtatg atggagataa taaatactat      180
gcagactccg tgaagggccg attcaccatc tccagagaca attccaagaa cacgctgtat      240
ctgcaaatga acagcctgag agccgaggac acggctgtgt attactgtgc gagagatatt      300
atcacatctc gcccgacttt ggactactgg ggccagggaa ccctggtcac tgtctcctca      360

<210> SEQ ID NO 98
<211> LENGTH: 120
<212> TYPE: PRT
<213> ORGANISM: Artificial Sequence
<220> FEATURE:
<223> OTHER INFORMATION: Synthetic

<400> SEQUENCE: 98

```
Glu Val Gln Leu Val Gln Ser Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Gly Met His Trp Val Arg Gln Ala Pro Gly Lys Gly Leu Glu Trp Val
        35                  40                  45

Ala Val Val Trp Tyr Asp Gly Asp Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ile Ile Thr Ser Arg Pro Thr Leu Asp Tyr Trp Gly Gln
            100                 105                 110

Gly Thr Leu Val Thr Val Ser Ser
        115                 120

<210> SEQ ID NO 99
<211> LENGTH: 24
<212> TYPE: DNA
<213> ORGANISM: Artificial Sequence
<220> FEATURE:
<223> OTHER INFORMATION: Synthetic

<400> SEQUENCE: 99
ggattcacct tcagtaatta tggc                                          24

<210> SEQ ID NO 100
<211> LENGTH: 8
<212> TYPE: PRT
<213> ORGANISM: Artificial Sequence
<220> FEATURE:
<223> OTHER INFORMATION: Synthetic

<400> SEQUENCE: 100

Gly Phe Thr Phe Ser Asn Tyr Gly
1               5

<210> SEQ ID NO 101
<211> LENGTH: 24
<212> TYPE: DNA
<213> ORGANISM: Artificial Sequence
<220> FEATURE:
<223> OTHER INFORMATION: Synthetic

<400> SEQUENCE: 101
gtttggtatg atggagataa taaa                                          24

<210> SEQ ID NO 102
<211> LENGTH: 8
<212> TYPE: PRT
<213> ORGANISM: Artificial Sequence
<220> FEATURE:
<223> OTHER INFORMATION: Synthetic

<400> SEQUENCE: 102

Val Trp Tyr Asp Gly Asp Asn Lys
1               5

<210> SEQ ID NO 103
<211> LENGTH: 39
<212> TYPE: DNA
```

<210> SEQ ID NO 103
<211> LENGTH: 39
<212> TYPE: DNA
<213> ORGANISM: Artificial Sequence
<220> FEATURE:
<223> OTHER INFORMATION: Synthetic

<400> SEQUENCE: 103
gcgagagata ttatcacatc tcgcccgact ttggactac                             39

<210> SEQ ID NO 104
<211> LENGTH: 13
<212> TYPE: PRT
<213> ORGANISM: Artificial Sequence
<220> FEATURE:
<223> OTHER INFORMATION: Synthetic

<400> SEQUENCE: 104

Ala Arg Asp Ile Ile Thr Ser Arg Pro Thr Leu Asp Tyr
 1               5                  10

<210> SEQ ID NO 105
<211> LENGTH: 324
<212> TYPE: DNA
<213> ORGANISM: Artificial Sequence
<220> FEATURE:
<223> OTHER INFORMATION: Synthetic

<400> SEQUENCE: 105
gacatccagt tgacccagtc tccatccttc ctgtctgcat ctgtaggaga cagagtcacc      60
atcacttgct gggccagtca gggcattaac agttatttag cctggtatca gcaaaaacca    120
gggaaagccc ctaagctcct gatctatcct gcatccactt tgcaaagtgg ggtcccatca    180
aggttcagcg gcagtggatc tgggacagaa ttcactctca caatcagcag cctgcagcct    240
gtagattttg caacttatta ctgtcaacag cttaatagtt acccgctcac tttcggcgga    300
gggaccaagg tggagatcaa acga                                           324

<210> SEQ ID NO 106
<211> LENGTH: 108
<212> TYPE: PRT
<213> ORGANISM: Artificial Sequence
<220> FEATURE:
<223> OTHER INFORMATION: Synthetic

<400> SEQUENCE: 106

Asp Ile Gln Leu Thr Gln Ser Pro Ser Phe Leu Ser Ala Ser Val Gly
 1               5                  10                  15

Asp Arg Val Thr Ile Thr Cys Trp Ala Ser Gln Gly Ile Asn Ser Tyr
             20                  25                  30

Leu Ala Trp Tyr Gln Gln Lys Pro Gly Lys Ala Pro Lys Leu Leu Ile
         35                  40                  45

Tyr Pro Ala Ser Thr Leu Gln Ser Gly Val Pro Ser Arg Phe Ser Gly
     50                  55                  60

Ser Gly Ser Gly Thr Glu Phe Thr Leu Thr Ile Ser Ser Leu Gln Pro
 65                  70                  75                  80

Val Asp Phe Ala Thr Tyr Tyr Cys Gln Gln Leu Asn Ser Tyr Pro Leu
                 85                  90                  95

Thr Phe Gly Gly Gly Thr Lys Val Glu Ile Lys Arg
            100                 105

<210> SEQ ID NO 107
<211> LENGTH: 18
<212> TYPE: DNA
<213> ORGANISM: Artificial Sequence

```
<220> FEATURE:
<223> OTHER INFORMATION: Synthetic

<400> SEQUENCE: 107
cagggcatta acagttat                                                   18

<210> SEQ ID NO 108
<211> LENGTH: 6
<212> TYPE: PRT
<213> ORGANISM: Artificial Sequence
<220> FEATURE:
<223> OTHER INFORMATION: Synthetic

<400> SEQUENCE: 108

Gln Gly Ile Asn Ser Tyr
 1               5

<210> SEQ ID NO 109
<211> LENGTH: 9
<212> TYPE: DNA
<213> ORGANISM: Artificial Sequence
<220> FEATURE:
<223> OTHER INFORMATION: Synthetic

<400> SEQUENCE: 109 cctgcatcc                                                              9

<210> SEQ ID NO 110
<211> LENGTH: 3
<212> TYPE: PRT
<213> ORGANISM: Artificial Sequence
<220> FEATURE:
<223> OTHER INFORMATION: Synthetic

<400> SEQUENCE: 110

Pro Ala Ser
 1

<210> SEQ ID NO 111
<211> LENGTH: 27
<212> TYPE: DNA
<213> ORGANISM: Artificial Sequence
<220> FEATURE:
<223> OTHER INFORMATION: Synthetic

<400> SEQUENCE: 111
caacagctta atagttaccc gctcact                                         27

<210> SEQ ID NO 112
<211> LENGTH: 9
<212> TYPE: PRT
<213> ORGANISM: Artificial Sequence
<220> FEATURE:
<223> OTHER INFORMATION: Synthetic

<400> SEQUENCE: 112

Gln Gln Leu Asn Ser Tyr Pro Leu Thr
 1               5

<210> SEQ ID NO 113
<211> LENGTH: 354
<212> TYPE: DNA
<213> ORGANISM: Artificial Sequence
<220> FEATURE:
<223> OTHER INFORMATION: Synthetic

<400> SEQUENCE: 113
```

```
caggtgcagc tggtggagtc ggggggaggc ttggtcaagc ctggagggtc cctgagactc    60
tcctgtgcag cctctggatt caccttcagt gactactaca tgagctggat ccgccaggct   120
ccagggaagg ggctggagtg ggtttcatac attagtagta gtggtagtac catatactac   180
gcagactctg tgaagggccg attcaccata tccagggaca cgccaagaa ctcactgtat    240 ctgcaaatga acagcctgag agccgaggac acggccgtgt attactgtgc gagagattct   300
tcccaactgg ttttgactac tggggccag ggaaccctgg tcaccgtctc ctca         354
```

<210> SEQ ID NO 114
<211> LENGTH: 118
<212> TYPE: PRT
<213> ORGANISM: Artificial Sequence
<220> FEATURE:
<223> OTHER INFORMATION: Synthetic

<400> SEQUENCE: 114

```
Gln Val Gln Leu Val Glu Ser Gly Gly Gly Leu Val Lys Pro Gly Gly
  1               5                  10                  15

Ser Leu Arg Leu Ser Cys Ala Ala Ser Gly Phe Thr Phe Ser Asp Tyr
             20                  25                  30

Tyr Met Ser Trp Ile Arg Gln Ala Pro Gly Lys Gly Leu Glu Trp Val
         35                  40                  45

Ser Tyr Ile Ser Ser Ser Gly Ser Thr Ile Tyr Tyr Ala Asp Ser Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Asp Ser Ser Gln Leu Gly Phe Asp Tyr Trp Gly Gln Gly Thr
            100                 105                 110

Leu Val Thr Val Ser Ser
        115
```

<210> SEQ ID NO 115
<211> LENGTH: 24
<212> TYPE: DNA
<213> ORGANISM: Artificial Sequence
<220> FEATURE:
<223> OTHER INFORMATION: Synthetic

<400> SEQUENCE: 115

```
ggattcacct tcagtgacta ctac                                           24
```

<210> SEQ ID NO 116
<211> LENGTH: 8
<212> TYPE: PRT
<213> ORGANISM: Artificial Sequence
<220> FEATURE:
<223> OTHER INFORMATION: Synthetic

<400> SEQUENCE: 116

```
Gly Phe Thr Phe Ser Asp Tyr Tyr
  1               5
```

<210> SEQ ID NO 117
<211> LENGTH: 24
<212> TYPE: DNA
<213> ORGANISM: Artificial Sequence
<220> FEATURE:
<223> OTHER INFORMATION: Synthetic

<400> SEQUENCE: 117
attagtagta gtggtagtac cata                                              24

<210> SEQ ID NO 118
<211> LENGTH: 8
<212> TYPE: PRT
<213> ORGANISM: Artificial Sequence
<220> FEATURE:
<223> OTHER INFORMATION: Synthetic

<400> SEQUENCE: 118

Ile Ser Ser Ser Gly Ser Thr Ile
 1               5

<210> SEQ ID NO 119
<211> LENGTH: 33
<212> TYPE: DNA
<213> ORGANISM: Artificial Sequence
<220> FEATURE:
<223> OTHER INFORMATION: Synthetic

<400> SEQUENCE: 119
gcgagagatt cttcccaact gggttttgac tac                                    33

<210> SEQ ID NO 120
<211> LENGTH: 11
<212> TYPE: PRT
<213> ORGANISM: Artificial Sequence
<220> FEATURE:
<223> OTHER INFORMATION: Synthetic

<400> SEQUENCE: 120

Ala Arg Asp Ser Ser Gln Leu Gly Phe Asp Tyr
 1               5                  10

<210> SEQ ID NO 121
<211> LENGTH: 324
<212> TYPE: DNA
<213> ORGANISM: Artificial Sequence
<220> FEATURE:
<223> OTHER INFORMATION: Synthetic

<400> SEQUENCE: 121
gacatccaga tgacccagtc tccatcctcc ctgtctgcat ctgtaggaga cagagtcacc        60
atcacttgcc gggcaagtca gagcattatc agcttttaa attggtatca gcagaaacca       120
gggaaggccc ctaagctcct gatctatact gcatccagtt tgcaaagtgg ggtcccatca       180
aggttcagtg gcagtggatc tgggacagat ttcactctca ccatcagcag tctacaacct       240
gaagattttg caacttacta ctgtcaacag acttacagta tccgctcac tttcggcgga        300 gggaccaagg tggaaatcaa acga                                             324

<210> SEQ ID NO 122
<211> LENGTH: 108
<212> TYPE: PRT
<213> ORGANISM: Artificial Sequence
<220> FEATURE:
<223> OTHER INFORMATION: Synthetic

<400> SEQUENCE: 122

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ile Ser Phe

```
                    20                  25                  30
Leu Asn Trp Tyr Gln Gln Lys Pro Gly Lys Ala Pro Lys Leu Leu Ile
                35                  40                  45

Tyr Thr Ala Ser Ser Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Thr Tyr Ser Asn Pro Leu
                 85                  90                  95

Thr Phe Gly Gly Gly Thr Lys Val Glu Ile Lys Arg
               100                 105
```

<210> SEQ ID NO 123
<211> LENGTH: 18
<212> TYPE: DNA
<213> ORGANISM: Artificial Sequence
<220> FEATURE:
<223> OTHER INFORMATION: Synthetic

<400> SEQUENCE: 123
cagagcatta tcagcttt                                                     18

<210> SEQ ID NO 124
<211> LENGTH: 6
<212> TYPE: PRT
<213> ORGANISM: Artificial Sequence
<220> FEATURE:
<223> OTHER INFORMATION: Synthetic

<400> SEQUENCE: 124

Gln Ser Ile Ile Ser Phe
 1               5

<210> SEQ ID NO 125
<211> LENGTH: 9
<212> TYPE: DNA
<213> ORGANISM: Artificial Sequence
<220> FEATURE:
<223> OTHER INFORMATION: Synthetic

<400> SEQUENCE: 125 actgcatcc                                                                9

<210> SEQ ID NO 126
<211> LENGTH: 3
<212> TYPE: PRT
<213> ORGANISM: Artificial Sequence
<220> FEATURE:
<223> OTHER INFORMATION: Synthetic

<400> SEQUENCE: 126

Thr Ala Ser
 1

<210> SEQ ID NO 127
<211> LENGTH: 27
<212> TYPE: DNA
<213> ORGANISM: Artificial Sequence
<220> FEATURE:
<223> OTHER INFORMATION: Synthetic

<400> SEQUENCE: 127
caacagactt acagtaatcc gctcact                                           27

<210> SEQ ID NO 128
<211> LENGTH: 9
<212> TYPE: PRT
<213> ORGANISM: Artificial Sequence
<220> FEATURE:
<223> OTHER INFORMATION: Synthetic

<400> SEQUENCE: 128

Gln Gln Thr Tyr Ser Asn Pro Leu Thr
1               5

<210> SEQ ID NO 129
<211> LENGTH: 342
<212> TYPE: DNA
<213> ORGANISM: Artificial Sequence
<220> FEATURE:
<223> OTHER INFORMATION: Synthetic

<400> SEQUENCE: 129
caggtgcagc tggtacagtc tggacctgag gtgaagaagc ctggggcctc agtgagggtc      60
tcctgtaagg cttctggtta ccttagtgac tttattatca cctgggtgcg acaggcccct     120
ggacaagggc ttgagtggat gggatggatc agcacttaca gtggtgacac agactctgca     180
ccgaagttcc agggcagagt caccatgacc acagacacat ccacgactac agtcttcttg     240
gaactgagga gcctgagatc tgacgacacg gccgtgtatt attgtgcgag agggcggctg     300
tttgactact ggggccaggg aaccctggtc accgtctcct ca                       342

<210> SEQ ID NO 130
<211> LENGTH: 114
<212> TYPE: PRT
<213> ORGANISM: Artificial Sequence
<220> FEATURE:
<223> OTHER INFORMATION: Synthetic

<400> SEQUENCE: 130

Gln Val Gln Leu Val Gln Ser Gly Pro Glu Val Lys Lys Pro Gly Ala
1               5                   10                  15

Ser Val Arg Val Ser Cys Lys Ala Ser Gly Tyr Leu Ser Asp Phe Ile
            20                  25                  30

Ile Thr Trp Val Arg Gln Ala Pro Gly Gln Gly Leu Glu Trp Met Gly
        35                  40                  45

Trp Ile Ser Thr Tyr Ser Gly Asp Thr Asp Ser Ala Pro Lys Phe Gln
    50                  55                  60

Gly Arg Val Thr Met Thr Thr Asp Thr Ser Thr Thr Thr Val Phe Leu
65                  70                  75                  80

Glu Leu Arg Ser Leu Arg Ser Asp Asp Thr Ala Val Tyr Tyr Cys Ala
                85                  90                  95

Arg Gly Arg Leu Phe Asp Tyr Trp Gly Gln Gly Thr Leu Val Thr Val
            100                 105                 110

Ser Ser

<210> SEQ ID NO 131
<211> LENGTH: 21
<212> TYPE: DNA
<213> ORGANISM: Artificial Sequence
<220> FEATURE:
<223> OTHER INFORMATION: Synthetic

<400> SEQUENCE: 131
ggttacctta gtgactttat t                                                21

<210> SEQ ID NO 132
<211> LENGTH: 7
<212> TYPE: PRT
<213> ORGANISM: Artificial Sequence
<220> FEATURE:
<223> OTHER INFORMATION: Synthetic

<400> SEQUENCE: 132

Gly Tyr Leu Ser Asp Phe Ile
 1               5

<210> SEQ ID NO 133
<211> LENGTH: 24
<212> TYPE: DNA
<213> ORGANISM: Artificial Sequence
<220> FEATURE:
<223> OTHER INFORMATION: Synthetic

<400> SEQUENCE: 133
atcagcactt acagtggtga caca                                          24

<210> SEQ ID NO 134
<211> LENGTH: 8
<212> TYPE: PRT
<213> ORGANISM: Artificial Sequence
<220> FEATURE:
<223> OTHER INFORMATION: Synthetic

<400> SEQUENCE: 134

Ile Ser Thr Tyr Ser Gly Asp Thr
 1               5

<210> SEQ ID NO 135
<211> LENGTH: 24
<212> TYPE: DNA
<213> ORGANISM: Artificial Sequence
<220> FEATURE:
<223> OTHER INFORMATION: Synthetic

<400> SEQUENCE: 135
gcgagagggc ggctgtttga ctac                                          24

<210> SEQ ID NO 136
<211> LENGTH: 8
<212> TYPE: PRT
<213> ORGANISM: Artificial Sequence
<220> FEATURE:
<223> OTHER INFORMATION: Synthetic

<400> SEQUENCE: 136

Ala Arg Gly Arg Leu Phe Asp Tyr
 1               5

<210> SEQ ID NO 137
<211> LENGTH: 339
<212> TYPE: DNA
<213> ORGANISM: Artificial Sequence
<220> FEATURE:
<223> OTHER INFORMATION: Synthetic

<400> SEQUENCE: 137
gatgttgtga tgactcagtc tccactctcc ctgcccgtca cccttggaca gccggcctcc    60
atctcctgca ggtctagtca aagcctcgta tacagtgatg aaacaccta cttgaattgg   120 tttcaacaga ggccaggcca atctccaagg cgcctaattt ataaggtttc taaccgggac   180

```
tctggggtcc cagacagatt cagcggcagt gggtcaggca ctgatttcac actgaaaatc        240
agcagggtgg aggctgagga tgttggggtt tattactgca tgcaaggtac acactggccg        300 tacactttg gccaggggac caagctggag atcaaacga                                339
```

<210> SEQ ID NO 138
<211> LENGTH: 113
<212> TYPE: PRT
<213> ORGANISM: Artificial Sequence
<220> FEATURE:
<223> OTHER INFORMATION: Synthetic

<400> SEQUENCE: 138

```
Asp Val Val Met Thr Gln Ser Pro Leu Ser Leu Pro Val Thr Leu Gly
 1               5                  10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Tyr Thr Phe Gly Gln Gly Thr Lys Leu Glu Ile Lys
            100                 105                 110

Arg
```

<210> SEQ ID NO 139
<211> LENGTH: 33
<212> TYPE: DNA
<213> ORGANISM: Artificial Sequence
<220> FEATURE:
<223> OTHER INFORMATION: Synthetic

<400> SEQUENCE: 139

```
caaagcctcg tatacagtga tggaaacacc tac                                      33
```

<210> SEQ ID NO 140
<211> LENGTH: 11
<212> TYPE: PRT
<213> ORGANISM: Artificial Sequence
<220> FEATURE:
<223> OTHER INFORMATION: Synthetic

<400> SEQUENCE: 140

```
Gln Ser Leu Val Tyr Ser Asp Gly Asn Thr Tyr
 1               5                  10
```

<210> SEQ ID NO 141
<211> LENGTH: 9
<212> TYPE: DNA
<213> ORGANISM: Artificial Sequence
<220> FEATURE:
<223> OTHER INFORMATION: Synthetic

<400> SEQUENCE: 141

```
aaggtttct                                                                  9
```

<210> SEQ ID NO 142

<211> LENGTH: 3
<212> TYPE: PRT
<213> ORGANISM: Artificial Sequence
<220> FEATURE:
<223> OTHER INFORMATION: Synthetic

<400> SEQUENCE: 142

Lys Val Ser
 1

<210> SEQ ID NO 143
<211> LENGTH: 27
<212> TYPE: DNA
<213> ORGANISM: Artificial Sequence
<220> FEATURE:
<223> OTHER INFORMATION: Synthetic

<400> SEQUENCE: 143
atgcaaggta cacactggcc gtacact                                          27

<210> SEQ ID NO 144
<211> LENGTH: 9
<212> TYPE: PRT
<213> ORGANISM: Artificial Sequence
<220> FEATURE:
<223> OTHER INFORMATION: Synthetic

<400> SEQUENCE: 144

Met Gln Gly Thr His Trp Pro Tyr Thr
 1               5

<210> SEQ ID NO 145
<211> LENGTH: 354
<212> TYPE: DNA
<213> ORGANISM: Artificial Sequence
<220> FEATURE:
<223> OTHER INFORMATION: Synthetic

<400> SEQUENCE: 145
caggtgcagc tggtggagtc tgggggagtc tcggtcaagc ctggagggtc cctgcgactc      60
tcctgtgcag cctctggatt caccttcagt gactactaca tgagctggat ccgccaggcg     120
ccagggaagg gactggagtg ggtttcgtac attggtagta gtggtactaa tgactactac     180
gcagactctg tgaagggccg attcaccatc tccagggaca cgccaagaa ctcactgtat      240 cttcaaatgg acagcctgag agccgaggac acggccgtct attactgtgc gagagattct     300
tcccaaatgg gttttgacta ctggggccag ggaaccctgg tcactgtctc ctca           354

<210> SEQ ID NO 146
<211> LENGTH: 118
<212> TYPE: PRT
<213> ORGANISM: Artificial Sequence
<220> FEATURE:
<223> OTHER INFORMATION: Synthetic

<400> SEQUENCE: 146

Gln Val Gln Leu Val Glu Ser Gly Gly Val Ser Val Lys Pro Gly Gly
 1               5                  10                  15

Ser Leu Arg Leu Ser Cys Ala Ala Ser Gly Phe Thr Phe Ser Asp Tyr
                20                  25                  30

Tyr Met Ser Trp Ile Arg Gln Ala Pro Gly Lys Gly Leu Glu Trp Val
            35                  40                  45

Ser Tyr Ile Gly Ser Ser Gly Thr Asn Asp Tyr Tyr Ala Asp Ser Val
        50                  55                  60

```
Lys Gly Arg Phe Thr Ile Ser Arg Asp Asn Ala Lys Asn Ser Leu Tyr
 65                  70                  75                  80

Leu Gln Met Asp Ser Leu Arg Ala Glu Asp Thr Ala Val Tyr Tyr Cys
                 85                  90                  95

Ala Arg Asp Ser Ser Gln Met Gly Phe Asp Tyr Trp Gly Gln Gly Thr
            100                 105                 110

Leu Val Thr Val Ser Ser
        115
```

<210> SEQ ID NO 147
<211> LENGTH: 24
<212> TYPE: DNA
<213> ORGANISM: Artificial Sequence
<220> FEATURE:
<223> OTHER INFORMATION: Synthetic

<400> SEQUENCE: 147
ggattcacct tcagtgacta ctac                                        24

<210> SEQ ID NO 148
<211> LENGTH: 8
<212> TYPE: PRT
<213> ORGANISM: Artificial Sequence
<220> FEATURE:
<223> OTHER INFORMATION: Synthetic

<400> SEQUENCE: 148

```
Gly Phe Thr Phe Ser Asp Tyr Tyr
 1               5
```

<210> SEQ ID NO 149
<211> LENGTH: 24
<212> TYPE: DNA
<213> ORGANISM: Artificial Sequence
<220> FEATURE:
<223> OTHER INFORMATION: Synthetic

<400> SEQUENCE: 149
attggtagta gtggtactaa tgac                                        24

<210> SEQ ID NO 150
<211> LENGTH: 8
<212> TYPE: PRT
<213> ORGANISM: Artificial Sequence
<220> FEATURE:
<223> OTHER INFORMATION: Synthetic

<400> SEQUENCE: 150

```
Ile Gly Ser Ser Gly Thr Asn Asp
 1               5
```

<210> SEQ ID NO 151
<211> LENGTH: 33
<212> TYPE: DNA
<213> ORGANISM: Artificial Sequence
<220> FEATURE:
<223> OTHER INFORMATION: Synthetic

<400> SEQUENCE: 151
gcgagagatt cttcccaaat gggttttgac tac                              33

<210> SEQ ID NO 152
<211> LENGTH: 11
<212> TYPE: PRT

<213> ORGANISM: Artificial Sequence
<220> FEATURE:
<223> OTHER INFORMATION: Synthetic

<400> SEQUENCE: 152

Ala Arg Asp Ser Ser Gln Met Gly Phe Asp Tyr
1               5                   10

<210> SEQ ID NO 153
<211> LENGTH: 324
<212> TYPE: DNA
<213> ORGANISM: Artificial Sequence
<220> FEATURE:
<223> OTHER INFORMATION: Synthetic

<400> SEQUENCE: 153

```
gacatccaga tgacccagtc tccatcctcc ctgtctgctt ctgtgggaga cagagtcacc    60
atcacttgcc gggcaagtca gaacattatc aacttttaa attggtatca gcagagacca   120
gggaaagccc ctcagctcct gatctatgtt gcagccagct tgcagagtgg ggtcccatca   180
aggttcactg gcagtggata tgggacagat ttcactctca ccatcagcag tctgcaacct   240
gaggatttcg caacttacta ctgtcaacag acttacacta acccgctcac tttcggcgga   300
gggaccaagg tggagatcaa acga                                          324
```

<210> SEQ ID NO 154
<211> LENGTH: 108
<212> TYPE: PRT
<213> ORGANISM: Artificial Sequence
<220> FEATURE:
<223> OTHER INFORMATION: Synthetic

<400> SEQUENCE: 154

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Ile Ile Asn Phe
            20                  25                  30

Leu Asn Trp Tyr Gln Gln Arg Pro Gly Lys Ala Pro Gln Leu Leu Ile
        35                  40                  45

Tyr Val Ala Ala Ser Leu Gln Ser Gly Val Pro Ser Arg Phe Thr Gly
    50                  55                  60

Ser Gly Tyr Gly Thr Asp Phe Thr Leu Thr Ile Ser Ser Leu Gln Pro
65                  70                  75                  80

Glu Asp Phe Ala Thr Tyr Tyr Cys Gln Gln Thr Tyr Thr Asn Pro Leu
                85                  90                  95

Thr Phe Gly Gly Gly Thr Lys Val Glu Ile Lys Arg
            100                 105

<210> SEQ ID NO 155
<211> LENGTH: 18
<212> TYPE: DNA
<213> ORGANISM: Artificial Sequence
<220> FEATURE:
<223> OTHER INFORMATION: Synthetic

<400> SEQUENCE: 155
cagaacatta tcaacttt                                                  18

<210> SEQ ID NO 156
<211> LENGTH: 6
<212> TYPE: PRT
<213> ORGANISM: Artificial Sequence

```
<220> FEATURE:
<223> OTHER INFORMATION: Synthetic

<400> SEQUENCE: 156

Gln Asn Ile Ile Asn Phe
 1               5

<210> SEQ ID NO 157
<211> LENGTH: 9
<212> TYPE: DNA
<213> ORGANISM: Artificial Sequence
<220> FEATURE:
<223> OTHER INFORMATION: Synthetic

<400> SEQUENCE: 157 gttgcagcc                                                                9

<210> SEQ ID NO 158
<211> LENGTH: 3
<212> TYPE: PRT
<213> ORGANISM: Artificial Sequence
<220> FEATURE:
<223> OTHER INFORMATION: Synthetic

<400> SEQUENCE: 158

Val Ala Ala
 1

<210> SEQ ID NO 159
<211> LENGTH: 27
<212> TYPE: DNA
<213> ORGANISM: Artificial Sequence
<220> FEATURE:
<223> OTHER INFORMATION: Synthetic

<400> SEQUENCE: 159
caacagactt acactaaccc gctcact                                            27

<210> SEQ ID NO 160
<211> LENGTH: 9
<212> TYPE: PRT
<213> ORGANISM: Artificial Sequence
<220> FEATURE:
<223> OTHER INFORMATION: Synthetic

<400> SEQUENCE: 160

Gln Gln Thr Tyr Thr Asn Pro Leu Thr
 1               5

<210> SEQ ID NO 161
<211> LENGTH: 460
<212> TYPE: PRT
<213> ORGANISM: Homo sapiens

<400> SEQUENCE: 161

Met Phe Thr Ile Lys Leu Leu Leu Phe Ile Val Pro Leu Val Ile Ser
 1               5                  10                  15

Ser Arg Ile Asp Gln Asp Asn Ser Ser Phe Asp Ser Leu Ser Pro Glu
                20                  25                  30

Pro Lys Ser Arg Phe Ala Met Leu Asp Asp Val Lys Ile Leu Ala Asn
            35                  40                  45

Gly Leu Leu Gln Leu Gly His Gly Leu Lys Asp Phe Val His Lys Thr
        50                  55                  60

Lys Gly Gln Ile Asn Asp Ile Phe Gln Lys Leu Asn Ile Phe Asp Gln
```

```
             65                  70                  75                  80
Ser Phe Tyr Asp Leu Ser Leu Gln Thr Ser Glu Ile Lys Glu Glu
                    85                  90                  95

Lys Glu Leu Arg Arg Thr Thr Tyr Lys Leu Gln Val Lys Asn Glu Glu
                100                 105                 110

Val Lys Asn Met Ser Leu Glu Leu Asn Ser Lys Leu Glu Ser Leu Leu
                115                 120                 125

Glu Glu Lys Ile Leu Leu Gln Gln Lys Val Lys Tyr Leu Glu Glu Gln
            130                 135                 140

Leu Thr Asn Leu Ile Gln Asn Gln Pro Glu Thr Pro Glu His Pro Glu
145                 150                 155                 160

Val Thr Ser Leu Lys Thr Phe Val Glu Lys Gln Asp Asn Ser Ile Lys
                165                 170                 175

Asp Leu Leu Gln Thr Val Glu Asp Gln Tyr Lys Gln Leu Asn Gln Gln
                180                 185                 190

His Ser Gln Ile Lys Glu Ile Glu Asn Gln Leu Arg Arg Thr Ser Ile
            195                 200                 205

Gln Glu Pro Thr Glu Ile Ser Leu Ser Ser Lys Pro Arg Ala Pro Arg
            210                 215                 220

Thr Thr Pro Phe Leu Gln Leu Asn Glu Ile Arg Asn Val Lys His Asp
225                 230                 235                 240

Gly Ile Pro Ala Glu Cys Thr Thr Ile Tyr Asn Arg Gly Glu His Thr
                245                 250                 255

Ser Gly Met Tyr Ala Ile Arg Pro Ser Asn Ser Gln Val Phe His Val
                260                 265                 270

Tyr Cys Asp Val Ile Ser Gly Ser Pro Trp Thr Leu Ile Gln His Arg
            275                 280                 285

Ile Asp Gly Ser Gln Asn Phe Asn Glu Thr Trp Glu Asn Tyr Lys Tyr
            290                 295                 300

Gly Phe Gly Arg Leu Asp Gly Glu Phe Trp Leu Gly Leu Glu Lys Ile
305                 310                 315                 320

Tyr Ser Ile Val Lys Gln Ser Asn Tyr Val Leu Arg Ile Glu Leu Glu
                325                 330                 335

Asp Trp Lys Asp Asn Lys His Tyr Ile Glu Tyr Ser Phe Tyr Leu Gly
                340                 345                 350

Asn His Glu Thr Asn Tyr Thr Leu His Leu Val Ala Ile Thr Gly Asn
            355                 360                 365

Val Pro Asn Ala Ile Pro Glu Asn Lys Asp Leu Val Phe Ser Thr Trp
370                 375                 380

Asp His Lys Ala Lys Gly His Phe Asn Cys Pro Glu Gly Tyr Ser Gly
385                 390                 395                 400

Gly Trp Trp Trp His Asp Glu Cys Gly Glu Asn Asn Leu Asn Gly Lys
                405                 410                 415

Tyr Asn Lys Pro Arg Ala Lys Ser Lys Pro Glu Arg Arg Arg Gly Leu
                420                 425                 430

Ser Trp Lys Ser Gln Asn Gly Arg Leu Tyr Ser Ile Lys Ser Thr Lys
            435                 440                 445

Met Leu Ile His Pro Thr Asp Ser Glu Ser Phe Glu
450                 455                 460

<210> SEQ ID NO 162
<211> LENGTH: 1383
<212> TYPE: DNA
<213> ORGANISM: Homo sapiens
```

<400> SEQUENCE: 162

```
atgttcacaa ttaagctcct tcttttatt gttcctctag ttatttcctc cagaattgat      60
caagacaatt catcatttga ttctctatct ccagagccaa atcaagatt tgctatgtta     120
gacgatgtaa aaattttagc caatggcctc cttcagttgg acatggtct taaagacttt     180
gtccataaga cgaagggcca attaatgac atatttcaaa aactcaacat atttgatcag     240
tcttttatg atctatcgct gcaaaccagt gaaatcaaag aagaagaaaa ggaactgaga     300
agaactacat ataaactaca agtcaaaaat gaagaggtaa agaatatgtc acttgaactc     360
aactcaaaac ttgaaagcct cctagaagaa aaaattctac ttcaacaaaa agtgaaatat     420
ttagaagagc aactaactaa cttaattcaa atcaacctg aaactccaga cacccagaa      480
gtaacttcac ttaaaacttt tgtagaaaaa caagataata gcatcaaaga ccttctccag     540
accgtggaag accaatataa acaattaaac caacagcata gtcaaataaa agaaatagaa     600
aatcagctca gaaggactag tattcaagaa cccacagaaa tttctctatc ttccaagcca     660
agagcaccaa gaactactcc ctttcttcag ttgaatgaaa taagaaatgt aaaacatgat     720
ggcattcctg ctgaatgtac caccatttat aacagaggtg aacatacaag tggcatgtat     780
gccatcagac ccagcaactc tcaagttttt catgtctact gtgatgttat atcaggtagt     840
ccatggacat taattcaaca tcgaatagat ggatcacaaa acttcaatga acgtgggag      900
aactacaaat atggttttgg gaggcttgat ggagaatttt ggttgggcct agagaagata     960
tactccatag tgaagcaatc taattatgtt ttacgaattg agttgaaga ctggaaagac     1020
aacaaacatt atattgaata ttcttttta cttgggaaatc acgaaaccaa ctatacgcta     1080
catctagttg cgattactgg caatgtcccc aatgcaatcc cggaaaacaa agatttggtg     1140
ttttctactt gggatcacaa agcaaaagga cacttcaact gtccagaggg ttattcagga     1200
ggctggtggt ggcatgatga gtgtggaaa acaacctaa atggtaaata taacaaacca      1260
agagcaaaat ctaagccaga gaggagaaga ggattatctt ggaagtctca aaatggaagg     1320
ttatactcta aaaatcaac caaaatgttg atccatccaa cagattcaga aagctttgaa     1380
tga                                                                  1383
```

<210> SEQ ID NO 163
<211> LENGTH: 455
<212> TYPE: PRT
<213> ORGANISM: Mus musculus

<400> SEQUENCE: 163

```
Met His Thr Ile Lys Leu Phe Leu Phe Val Val Pro Leu Val Ile Ala
 1               5                  10                  15

Ser Arg Val Asp Pro Asp Leu Ser Ser Phe Asp Ser Ala Pro Ser Glu
            20                  25                  30

Pro Lys Ser Arg Phe Ala Met Leu Asp Asp Val Lys Ile Leu Ala Asn
        35                  40                  45

Gly Leu Leu Gln Leu Gly His Gly Leu Lys Asp Phe Val His Lys Thr
    50                  55                  60

Lys Gly Gln Ile Asn Asp Ile Phe Gln Lys Leu Asn Ile Phe Asp Gln
65                  70                  75                  80

Ser Phe Tyr Asp Leu Ser Leu Arg Thr Asn Glu Ile Lys Glu Glu Glu
                85                  90                  95

Lys Glu Leu Arg Arg Thr Thr Ser Thr Leu Gln Val Lys Asn Glu Glu
            100                 105                 110
```

Val Lys Asn Met Ser Val Glu Leu Asn Ser Lys Leu Glu Ser Leu Leu
        115                 120                 125

Glu Glu Lys Thr Ala Leu Gln His Lys Val Arg Ala Leu Glu Glu Gln
    130                 135                 140

Leu Thr Asn Leu Ile Leu Ser Pro Ala Gly Ala Gln Glu His Pro Glu
145                 150                 155                 160

Val Thr Ser Leu Lys Ser Phe Val Glu Gln Gln Asp Asn Ser Ile Arg
                165                 170                 175

Glu Leu Leu Gln Ser Val Glu Gln Tyr Lys Gln Leu Ser Gln Gln
            180                 185                 190

His Met Gln Ile Lys Glu Ile Glu Lys Gln Leu Arg Lys Thr Gly Ile
        195                 200                 205

Gln Glu Pro Ser Glu Asn Ser Leu Ser Ser Lys Ser Arg Ala Pro Arg
    210                 215                 220

Thr Thr Pro Pro Leu Gln Leu Asn Glu Thr Glu Asn Thr Glu Gln Asp
225                 230                 235                 240

Asp Leu Pro Ala Asp Cys Ser Ala Val Tyr Asn Arg Gly Glu His Thr
                245                 250                 255

Ser Gly Val Tyr Thr Ile Lys Pro Arg Asn Ser Gln Gly Phe Asn Val
            260                 265                 270

Tyr Cys Asp Thr Gln Ser Gly Ser Pro Trp Thr Leu Ile Gln His Arg
        275                 280                 285

Lys Asp Gly Ser Gln Asp Phe Asn Glu Thr Trp Glu Asn Tyr Glu Lys
    290                 295                 300

Gly Phe Gly Arg Leu Asp Gly Glu Phe Trp Leu Gly Leu Glu Lys Ile
305                 310                 315                 320

Tyr Ala Ile Val Gln Gln Ser Asn Tyr Ile Leu Arg Leu Glu Leu Gln
                325                 330                 335

Asp Trp Lys Asp Ser Lys His Tyr Val Glu Tyr Ser Phe His Leu Gly
            340                 345                 350

Ser His Glu Thr Asn Tyr Thr Leu His Val Ala Glu Ile Ala Gly Asn
        355                 360                 365

Ile Pro Gly Ala Leu Pro Glu His Thr Asp Leu Met Phe Ser Thr Trp
    370                 375                 380

Asn His Arg Ala Lys Gly Gln Leu Tyr Cys Pro Glu Ser Tyr Ser Gly
385                 390                 395                 400

Gly Trp Trp Trp Asn Asp Ile Cys Gly Glu Asn Asn Leu Asn Gly Lys
                405                 410                 415

Tyr Asn Lys Pro Arg Thr Lys Ser Arg Pro Glu Arg Arg Gly Ile
            420                 425                 430

Tyr Trp Arg Pro Gln Ser Arg Lys Leu Tyr Ala Ile Lys Ser Ser Lys
        435                 440                 445

Met Met Leu Gln Pro Thr Thr
    450                 455

<210> SEQ ID NO 164
<211> LENGTH: 406
<212> TYPE: PRT
<213> ORGANISM: Homo sapiens

<400> SEQUENCE: 164

Met Ser Gly Ala Pro Thr Ala Gly Ala Ala Leu Met Leu Cys Ala Ala
1               5                   10                  15

Thr Ala Val Leu Leu Ser Ala Gln Gly Gly Pro Val Gln Ser Lys Ser

```
            20                  25                  30
Pro Arg Phe Ala Ser Trp Asp Glu Met Asn Val Leu Ala His Gly Leu
            35                  40                  45

Leu Gln Leu Gly Gln Gly Leu Arg Glu His Ala Glu Arg Thr Arg Ser
        50                  55                  60

Gln Leu Ser Ala Leu Glu Arg Arg Leu Ser Ala Cys Gly Ser Ala Cys
65                  70                  75                  80

Gln Gly Thr Glu Gly Ser Thr Asp Leu Pro Leu Ala Pro Glu Ser Arg
                85                  90                  95

Val Asp Pro Glu Val Leu His Ser Leu Gln Thr Gln Leu Lys Ala Gln
            100                 105                 110

Asn Ser Arg Ile Gln Gln Leu Phe His Lys Val Ala Gln Gln Gln Arg
        115                 120                 125

His Leu Glu Lys Gln His Leu Arg Ile Gln His Leu Gln Ser Gln Phe
    130                 135                 140

Gly Leu Leu Asp His Lys His Leu Asp His Glu Val Ala Lys Pro Ala
145                 150                 155                 160

Arg Arg Lys Arg Leu Pro Glu Met Ala Gln Pro Val Asp Pro Ala His
                165                 170                 175

Asn Val Ser Arg Leu His Arg Leu Pro Arg Asp Cys Gln Glu Leu Phe
            180                 185                 190

Gln Val Gly Glu Arg Gln Ser Gly Leu Phe Glu Ile Gln Pro Gln Gly
        195                 200                 205

Ser Pro Pro Phe Leu Val Asn Cys Lys Met Thr Ser Asp Gly Gly Trp
    210                 215                 220

Thr Val Ile Gln Arg Arg His Asp Gly Ser Val Asp Phe Asn Arg Pro
225                 230                 235                 240

Trp Glu Ala Tyr Lys Ala Gly Phe Gly Asp Pro His Gly Glu Phe Trp
                245                 250                 255

Leu Gly Leu Glu Lys Val His Ser Ile Thr Gly Asp Arg Asn Ser Arg
            260                 265                 270

Leu Ala Val Gln Leu Arg Asp Trp Asp Gly Asn Ala Glu Leu Leu Gln
        275                 280                 285

Phe Ser Val His Leu Gly Gly Glu Asp Thr Ala Tyr Ser Leu Gln Leu
    290                 295                 300

Thr Ala Pro Val Ala Gly Gln Leu Gly Ala Thr Thr Val Pro Pro Ser
305                 310                 315                 320

Gly Leu Ser Val Pro Phe Ser Thr Trp Asp Gln Asp His Asp Leu Arg
                325                 330                 335

Arg Asp Lys Asn Cys Ala Lys Ser Leu Ser Gly Gly Trp Trp Phe Gly
            340                 345                 350

Thr Cys Ser His Ser Asn Leu Asn Gly Gln Tyr Phe Arg Ser Ile Pro
        355                 360                 365

Gln Gln Arg Gln Lys Leu Lys Lys Gly Ile Phe Trp Lys Thr Trp Arg
    370                 375                 380

Gly Arg Tyr Tyr Pro Leu Gln Ala Thr Thr Met Leu Ile Gln Pro Met
385                 390                 395                 400

Ala Ala Glu Ala Ala Ser
                405

<210> SEQ ID NO 165
<211> LENGTH: 386
<212> TYPE: PRT
<213> ORGANISM: Artificial Sequence
```

<220> FEATURE:
<223> OTHER INFORMATION: Synthetic

<400> SEQUENCE: 165

Ser Arg Ile Asp Gln Asp Asn Ser Ser Phe Asp Ser Leu Ser Pro Glu
1               5                   10                  15

Pro Lys Ser Arg Phe Ala Met Leu Asp Asp Val Lys Ile Leu Ala Asn
            20                  25                  30

Gly Leu Leu Gln Leu Gly His Gly Leu Lys Asp Phe Val His Lys Thr
        35                  40                  45

Lys Gly Gln Ile Asn Asp Ile Phe Gln Lys Leu Asn Ile Phe Asp Gln
50                  55                  60

Ser Phe Tyr Asp Leu Ser Leu Gln Thr Ser Glu Ile Lys Glu Glu Glu
65                  70                  75                  80

Lys Glu Leu Arg Arg Thr Thr Tyr Lys Leu Gln Val Lys Asn Glu Glu
                85                  90                  95

Val Lys Asn Met Ser Leu Glu Leu Asn Ser Lys Leu Glu Ser Leu Leu
            100                 105                 110

Glu Glu Lys Ile Leu Leu Gln Gln Lys Val Lys Tyr Leu Glu Glu Gln
        115                 120                 125

Leu Thr Asn Leu Ile Gln Asn Gln Pro Glu Thr Pro Glu His Pro Glu
130                 135                 140

Val Thr Ser Leu Lys Thr Phe Val Glu Pro Arg Gly Pro Thr Ile
145                 150                 155                 160

Lys Pro Cys Pro Pro Cys Lys Cys Pro Ala Pro Asn Leu Leu Gly Gly
                165                 170                 175

Pro Ser Val Phe Ile Phe Pro Pro Lys Ile Lys Asp Val Leu Met Ile
            180                 185                 190

Ser Leu Ser Pro Ile Val Thr Cys Val Val Asp Val Ser Glu Asp
            195                 200                 205

Asp Pro Asp Val Gln Ile Ser Trp Phe Val Asn Asn Val Glu Val His
        210                 215                 220

Thr Ala Gln Thr Gln Thr His Arg Glu Asp Tyr Asn Ser Thr Leu Arg
225                 230                 235                 240

Val Val Ser Ala Leu Pro Ile Gln His Gln Asp Trp Met Ser Gly Lys
                245                 250                 255

Glu Phe Lys Cys Lys Val Asn Asn Lys Asp Leu Pro Ala Pro Ile Glu
            260                 265                 270

Arg Thr Ile Ser Lys Pro Lys Gly Ser Val Arg Ala Pro Gln Val Tyr
        275                 280                 285

Val Leu Pro Pro Pro Glu Glu Glu Met Thr Lys Lys Gln Val Thr Leu
290                 295                 300

Thr Cys Met Val Thr Asp Phe Met Pro Glu Asp Ile Tyr Val Glu Trp
305                 310                 315                 320

Thr Asn Asn Gly Lys Thr Glu Leu Asn Tyr Lys Asn Thr Glu Pro Val
                325                 330                 335

Leu Asp Ser Asp Gly Ser Tyr Phe Met Tyr Ser Lys Leu Arg Val Glu
            340                 345                 350

Lys Lys Asn Trp Val Glu Arg Asn Ser Tyr Ser Cys Ser Val Val His
        355                 360                 365

Glu Gly Leu His Asn His His Thr Thr Lys Ser Phe Ser Arg Thr Pro
370                 375                 380

Gly Lys
385

<210> SEQ ID NO 166
<211> LENGTH: 235
<212> TYPE: PRT
<213> ORGANISM: Artificial Sequence
<220> FEATURE:
<223> OTHER INFORMATION: Synthetic

<400> SEQUENCE: 166

```
Gly Ala Pro Ser Arg Val Asp Pro Asp Leu Ser Ser Phe Asp Ser Ala
1               5                   10                  15

Pro Ser Glu Pro Lys Ser Arg Phe Ala Met Leu Asp Asp Val Lys Ile
            20                  25                  30

Leu Ala Asn Gly Leu Leu Gln Leu Gly His Gly Leu Lys Asp Phe Val
        35                  40                  45

His Lys Thr Lys Gly Gln Ile Asn Asp Ile Phe Gln Lys Leu Asn Ile
50                  55                  60

Phe Asp Gln Ser Phe Tyr Asp Leu Ser Leu Arg Thr Asn Glu Ile Lys
65                  70                  75                  80

Glu Glu Glu Lys Glu Leu Arg Arg Thr Thr Ser Thr Leu Gln Val Lys
                85                  90                  95

Asn Glu Glu Val Lys Asn Met Ser Val Glu Leu Asn Ser Lys Leu Glu
            100                 105                 110

Ser Leu Leu Glu Glu Lys Thr Ala Leu Gln His Lys Val Arg Ala Leu
        115                 120                 125

Glu Glu Gln Leu Thr Asn Leu Ile Leu Ser Pro Ala Gly Ala Gln Glu
    130                 135                 140

His Pro Glu Val Thr Ser Leu Lys Ser Phe Val Glu Gln Gln Asp Asn
145                 150                 155                 160

Ser Ile Arg Glu Leu Leu Gln Ser Val Glu Gln Tyr Lys Gln Leu
                165                 170                 175

Ser Gln Gln His Met Gln Ile Lys Glu Ile Glu Lys Gly Leu Arg Lys
            180                 185                 190

Thr Gly Ile Gln Glu Pro Ser Glu Asn Ser Leu Ser Ser Lys Ser Arg
        195                 200                 205

Ala Pro Arg Thr Thr Pro Pro Leu Gln Leu Asn Glu Thr Glu Asn Thr
    210                 215                 220

Glu Gln Asp Ala Ser His His His His His
225                 230                 235
```

<210> SEQ ID NO 167
<211> LENGTH: 182
<212> TYPE: PRT
<213> ORGANISM: Artificial Sequence
<220> FEATURE:
<223> OTHER INFORMATION: Synthetic

<400> SEQUENCE: 167

```
Ser Arg Ile Asp Gln Asp Asn Ser Phe Asp Ser Val Ser Pro Glu
1               5                   10                  15

Pro Lys Ser Arg Phe Ala Met Leu Asp Asp Val Lys Ile Leu Ala Asn
            20                  25                  30

Gly Leu Leu Gln Leu Gly His Gly Leu Lys Asp Phe Val His Lys Thr
        35                  40                  45

Lys Gly Gln Ile Asn Asp Ile Phe Gln Lys Leu Asn Ile Phe Asp Gln
    50                  55                  60

Ser Phe Tyr Asp Leu Ser Leu Gln Thr Ser Glu Ile Lys Glu Glu Glu
```

```
                65                  70                  75                  80
Lys Glu Leu Arg Arg Thr Thr Tyr Lys Leu Gln Val Lys Asn Glu Glu
                    85                  90                  95

Val Lys Asn Met Ser Leu Glu Leu Asn Ser Lys Leu Glu Ser Leu Leu
                100                 105                 110

Glu Glu Lys Ile Leu Leu Gln Gln Lys Val Lys Tyr Leu Glu Glu Gln
                115                 120                 125

Leu Thr Asn Leu Ile Gln Asn Gln Pro Ala Thr Pro Glu His Pro Glu
                130                 135                 140

Val Thr Ser Leu Lys Ser Phe Val Glu Lys Glu Gln Lys Leu Ile Ser
145                 150                 155                 160

Glu Glu Asp Leu Gly Gly Glu Gln Lys Leu Ile Ser Glu Glu Asp Leu
                165                 170                 175

His His His His His His
                180

<210> SEQ ID NO 168
<211> LENGTH: 33
<212> TYPE: PRT
<213> ORGANISM: Artificial Sequence
<220> FEATURE:
<223> OTHER INFORMATION: Synthetic

<400> SEQUENCE: 168

Arg Phe Ala Ser Trp Asp Glu Met Asn Val Leu Ala His Gly Leu Leu
1               5                   10                  15

Gln Leu Gly Gln Gly Leu Arg Glu His Ala Glu Arg Thr Arg Ser Gln
                20                  25                  30

Leu

<210> SEQ ID NO 169
<211> LENGTH: 33
<212> TYPE: PRT
<213> ORGANISM: Artificial Sequence
<220> FEATURE:
<223> OTHER INFORMATION: Synthetic

<400> SEQUENCE: 169

Arg Phe Ala Met Leu Asp Asp Val Lys Ile Leu Ala Asn Gly Leu Leu
1               5                   10                  15

Gln Leu Gly His Gly Leu Lys Asp Phe Val His Lys Thr Lys Gly Gln
                20                  25                  30

Ile

<210> SEQ ID NO 170
<211> LENGTH: 26
<212> TYPE: PRT
<213> ORGANISM: Artificial Sequence
<220> FEATURE:
<223> OTHER INFORMATION: Synthetic

<400> SEQUENCE: 170

Glu Pro Lys Ser Arg Phe Ala Met Leu Asp Asp Val Lys Ile Leu Ala
1               5                   10                  15

Asn Gly Leu Leu Gln Leu Gly His Gly Leu
                20                  25

<210> SEQ ID NO 171
<211> LENGTH: 7
<212> TYPE: PRT
```

```
<213> ORGANISM: Artificial Sequence
<220> FEATURE:
<223> OTHER INFORMATION: Synthetic

<400> SEQUENCE: 171

Ala Gly Ser Ser Pro Gly Gly
 1               5

<210> SEQ ID NO 172
<211> LENGTH: 5
<212> TYPE: PRT
<213> ORGANISM: Artificial Sequence
<220> FEATURE:
<223> OTHER INFORMATION: Synthetic

<400> SEQUENCE: 172

Gly Gly Gly Gly Ser
 1               5

<210> SEQ ID NO 173
<211> LENGTH: 10
<212> TYPE: PRT
<213> ORGANISM: Artificial Sequence
<220> FEATURE:
<223> OTHER INFORMATION: Synthetic

<400> SEQUENCE: 173

Gly Pro Ser Ser Gly Ala Pro Pro Pro Lys
 1               5                  10

<210> SEQ ID NO 174
<211> LENGTH: 6
<212> TYPE: PRT
<213> ORGANISM: Artificial Sequence
<220> FEATURE:
<223> OTHER INFORMATION: Synthetic

<400> SEQUENCE: 174

Gly Gly Gly Gly Ser Lys
 1               5

<210> SEQ ID NO 175
<211> LENGTH: 455
<212> TYPE: PRT
<213> ORGANISM: Rattus norvegicus

<400> SEQUENCE: 175

Met His Thr Ile Lys Leu Leu Leu Phe Val Val Pro Leu Val Ile Ser
 1               5                  10                  15

Ser Arg Val Asp Pro Asp Leu Ser Pro Phe Asp Ser Val Pro Ser Glu
                20                  25                  30

Pro Lys Ser Arg Phe Ala Met Leu Asp Asp Val Lys Ile Leu Ala Asn
            35                  40                  45

Gly Leu Leu Gln Leu Gly His Gly Leu Lys Asp Phe Val His Lys Thr
        50                  55                  60

Lys Gly Gln Ile Asn Asp Ile Phe Gln Lys Leu Asn Ile Phe Asp Gln
65                  70                  75                  80

Cys Phe Tyr Asp Leu Ser Leu Gln Thr Asn Glu Ile Lys Glu Glu Glu
                85                  90                  95

Lys Glu Leu Arg Arg Thr Thr Ser Lys Leu Gln Val Lys Asn Glu Glu
            100                 105                 110

Val Lys Asn Met Ser Leu Glu Leu Asn Ser Lys Leu Glu Ser Leu Leu
        115                 120                 125
```

Glu Glu Lys Met Ala Leu Gln His Arg Val Arg Ala Leu Glu Glu Gln
            130                 135                 140

Leu Thr Ser Leu Val Gln Asn Pro Pro Gly Ala Arg Glu His Pro Glu
145                 150                 155                 160

Val Thr Ser Leu Lys Ser Phe Val Glu Gln Gln Asp Asn Ser Ile Arg
                165                 170                 175

Glu Leu Leu Gln Ser Val Glu Glu Gln Tyr Lys Gln Leu Ser Gln Gln
            180                 185                 190

His Ile Gln Ile Lys Glu Ile Glu Asn Gln Leu Arg Lys Thr Gly Ile
        195                 200                 205

Gln Glu Pro Thr Glu Asn Ser Leu Tyr Ser Lys Pro Arg Ala Pro Arg
    210                 215                 220

Thr Thr Pro Pro Leu His Leu Lys Glu Ala Lys Asn Ile Glu Gln Asp
225                 230                 235                 240

Asp Leu Pro Ala Asp Cys Ser Ala Ile Tyr Asn Arg Gly Glu His Thr
                245                 250                 255

Ser Gly Val Tyr Thr Ile Arg Pro Ser Ser Ser Gln Val Phe Asn Val
            260                 265                 270

Tyr Cys Asp Thr Gln Ser Gly Thr Pro Arg Thr Leu Ile Gln His Arg
        275                 280                 285

Lys Asp Gly Ser Gln Asn Phe Asn Gln Thr Trp Glu Asn Tyr Glu Lys
    290                 295                 300

Gly Phe Gly Arg Leu Asp Gly Glu Phe Trp Leu Gly Leu Glu Lys Ile
305                 310                 315                 320

Tyr Ala Ile Val Lys Gln Ser Asn Tyr Ile Leu Arg Leu Glu Leu Gln
                325                 330                 335

Asp Trp Lys Asp Ser Lys His Tyr Ala Glu Tyr Ser Phe His Leu Gly
            340                 345                 350

Asn His Glu Thr Asn Tyr Thr Leu His Val Ala Glu Ile Ala Ala Asn
        355                 360                 365

Ile Pro Glu Ala Leu Pro Glu His Arg Asp Leu Met Phe Ser Thr Trp
    370                 375                 380

Asp His Arg Ala Lys Gly Gln Leu Tyr Cys Pro Glu Ser Tyr Ser Gly
385                 390                 395                 400

Gly Trp Trp Phe Ser Asp Met Cys Gly Glu Asn Asn Leu Asn Gly Lys
                405                 410                 415

Tyr Asn Lys Pro Arg Ala Lys Ser Lys Pro Glu Arg Arg Arg Gly Ile
            420                 425                 430

Ser Trp Arg Pro Arg Gly Gly Lys Leu Tyr Ser Ile Lys Ser Ser Lys
        435                 440                 445

Met Met Leu Gln Pro Thr Thr
    450                 455

<210> SEQ ID NO 176
<211> LENGTH: 252
<212> TYPE: PRT
<213> ORGANISM: Artificial Sequence
<220> FEATURE:
<223> OTHER INFORMATION: Synthetic

<400> SEQUENCE: 176

Ser Arg Val Asp Pro Asp Leu Ser Pro Phe Asp Ser Val Pro Ser Glu
1               5                   10                  15

Pro Lys Ser Arg Phe Ala Met Leu Asp Asp Val Lys Ile Leu Ala Asn
            20                  25                  30

Gly Leu Leu Gln Leu Gly His Gly Leu Lys Asp Phe Val His Lys Thr
            35                  40                  45

Lys Gly Gln Ile Asn Asp Ile Phe Gln Lys Leu Asn Ile Phe Asp Gln
 50                  55                  60

Cys Phe Tyr Asp Leu Ser Leu Gln Thr Asn Glu Ile Lys Glu Glu Glu
65                  70                  75                  80

Lys Glu Leu Arg Arg Thr Thr Ser Lys Leu Gln Val Lys Asn Glu Glu
                85                  90                  95

Val Lys Asn Met Ser Leu Glu Leu Asn Ser Lys Leu Glu Ser Leu Leu
            100                 105                 110

Glu Glu Lys Met Ala Leu Gln His Arg Val Arg Ala Leu Glu Glu Gln
        115                 120                 125

Leu Thr Ser Leu Val Gln Asn Pro Pro Gly Ala Arg Glu His Pro Glu
130                 135                 140

Val Thr Ser Leu Lys Ser Phe Val Glu Gln Gln Asp Asn Ser Ile Arg
145                 150                 155                 160

Glu Leu Leu Gln Ser Val Glu Gln Tyr Lys Gln Leu Ser Gln Gln
                165                 170                 175

His Ile Gln Ile Lys Glu Ile Glu Asn Gln Leu Arg Lys Thr Gly Ile
            180                 185                 190

Gln Glu Pro Thr Glu Asn Ser Leu Tyr Ser Lys Pro Arg Ala Pro Arg
        195                 200                 205

Thr Thr Pro Pro Leu His Leu Lys Glu Ala Lys Asn Ile Glu Gln Asp
210                 215                 220

Glu Gln Lys Leu Ile Ser Glu Glu Asp Leu Gly Gly Glu Gln Lys Leu
225                 230                 235                 240

Ile Ser Glu Glu Asp Leu His His His His His His
                245                 250

<210> SEQ ID NO 177
<211> LENGTH: 210
<212> TYPE: PRT
<213> ORGANISM: Macaca fascicularis

<400> SEQUENCE: 177

Met Phe Thr Ile Lys Leu Leu Phe Ile Val Pro Leu Val Ile Ser
 1               5                  10                  15

Ser Arg Ile Asp Gln Asp Asn Ser Ser Phe Asp Ser Val Ser Pro Glu
                20                  25                  30

Pro Lys Ser Arg Phe Ala Met Leu Asp Asp Val Lys Ile Leu Ala Asn
            35                  40                  45

Gly Leu Leu Gln Leu Gly His Gly Leu Lys Asp Phe Val His Lys Thr
 50                  55                  60

Lys Gly Gln Ile Asn Asp Ile Phe Gln Lys Leu Asn Ile Phe Asp Gln
65                  70                  75                  80

Ser Phe Tyr Asp Leu Ser Leu Gln Thr Ser Glu Ile Lys Glu Glu Glu
                85                  90                  95

Lys Glu Leu Arg Arg Thr Thr Tyr Lys Leu Gln Val Lys Asn Glu Glu
            100                 105                 110

Val Lys Asn Met Ser Leu Glu Leu Asn Ser Lys Leu Glu Ser Leu Leu
        115                 120                 125

Glu Glu Lys Ile Leu Leu Gln Gln Lys Val Lys Tyr Leu Glu Glu Gln
130                 135                 140

Leu Thr Asn Leu Ile Gln Asn Gln Pro Ala Thr Pro Glu His Pro Glu

```
            145                 150                 155                 160
Val Thr Ser Leu Lys Ser Phe Val Glu Lys Gln Asp Asn Ser Ile Lys
                165                 170                 175

Asp Leu Leu Gln Thr Val Glu Glu Gln Tyr Lys Gln Leu Asn Gln Gln
                180                 185                 190

His Ser Gln Ile Lys Glu Ile Glu Asn Gln Leu Arg Met Thr Asn Ile
            195                 200                 205

Gln Glu
    210

<210> SEQ ID NO 178
<211> LENGTH: 356
<212> TYPE: PRT
<213> ORGANISM: Artificial Sequence
<220> FEATURE:
<223> OTHER INFORMATION: Synthetic

<400> SEQUENCE: 178

Gly Pro Val Gln Ser Lys Ser Pro Arg Phe Ala Ser Trp Asp Glu Met
  1               5                  10                  15

Asn Val Leu Ala His Gly Leu Leu Gln Leu Gly Gln Gly Leu Arg Glu
                 20                  25                  30

His Ala Glu Arg Thr Arg Ser Gln Leu Ser Ala Leu Glu Arg Arg Leu
             35                  40                  45

Ser Ala Cys Gly Ser Ala Cys Gln Gly Thr Glu Gly Ser Thr Asp Leu
         50                  55                  60

Pro Leu Ala Pro Glu Ser Arg Val Asp Pro Glu Val Leu His Ser Leu
 65                  70                  75                  80

Gln Thr Gln Leu Lys Ala Gln Asn Ser Arg Ile Gln Gln Leu Phe His
                 85                  90                  95

Lys Val Ala Gln Gln Arg His Leu Glu Lys Gln His Leu Arg Ile
                100                 105                 110

Gln His Leu Gln Ser Gln Phe Gly Leu Leu Asp His Glu Pro Arg Gly Pro
                115                 120                 125

Thr Ile Lys Pro Cys Pro Pro Cys Lys Cys Pro Ala Pro Asn Leu Leu
            130                 135                 140

Gly Gly Pro Ser Val Phe Ile Phe Pro Pro Lys Ile Lys Asp Val Leu
145                 150                 155                 160

Met Ile Ser Leu Ser Pro Ile Val Thr Cys Val Val Val Asp Val Ser
                165                 170                 175

Glu Asp Asp Pro Asp Val Gln Ile Ser Trp Phe Val Asn Asn Val Glu
            180                 185                 190

Val His Thr Ala Gln Thr Gln Thr His Arg Glu Asp Tyr Asn Ser Thr
        195                 200                 205

Leu Arg Val Val Ser Ala Leu Pro Ile Gln His Gln Asp Trp Met Ser
    210                 215                 220

Gly Lys Glu Phe Lys Cys Lys Val Asn Asn Lys Asp Leu Pro Ala Pro
225                 230                 235                 240

Ile Glu Arg Thr Ile Ser Lys Pro Lys Gly Ser Val Arg Ala Pro Gln
                245                 250                 255

Val Tyr Val Leu Pro Pro Pro Glu Glu Met Thr Lys Lys Gln Val
                260                 265                 270

Thr Leu Thr Cys Met Val Thr Asp Phe Met Pro Glu Asp Ile Tyr Val
            275                 280                 285

Glu Trp Thr Asn Asn Gly Lys Thr Glu Leu Asn Tyr Lys Asn Thr Glu
```

Pro Val Leu Asp Ser Asp Gly Ser Tyr Phe Met Tyr Ser Lys Leu Arg
305                 310                 315                 320

Val Glu Lys Lys Asn Trp Val Glu Arg Asn Ser Tyr Cys Ser Val
                325                 330                 335

Val His Glu Gly Leu His Asn His Thr Thr Lys Ser Phe Ser Arg
            340                 345                 350

Thr Pro Gly Lys
        355

<210> SEQ ID NO 179
<211> LENGTH: 363
<212> TYPE: DNA
<213> ORGANISM: Artificial Sequence
<220> FEATURE:
<223> OTHER INFORMATION: Synthetic

<400> SEQUENCE: 179
gaggtgcagc ttttggagtc tgggggaggc ttggtacagc ctggggggtc cctgagactc      60
tcctgtgcag cctctggatt cacctttagc acctatgcca tgagctgggt ccgccaggct     120
ccagggaagg ggctggaggg ggtctcaggt attagtggta ctggttatag aacatactac     180
gcagactccg tgaagggccg attcaccatc tccagagaca attccaagaa ctcgctgtat     240
ctgcaaatga acagcctgag agccgaggac acggccgtat attactgtgc gaaagatcgg     300
ggcttactat ggttcgggga attaacctac tggggccagg aaccctggt caccgtctcc      360 tca                                                                   363

<210> SEQ ID NO 180
<211> LENGTH: 121
<212> TYPE: PRT
<213> ORGANISM: Artificial Sequence
<220> FEATURE:
<223> OTHER INFORMATION: Synthetic

<400> SEQUENCE: 180

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Ser Trp Val Arg Gln Ala Pro Gly Lys Gly Leu Glu Gly Val
        35                  40                  45

Ser Gly Ile Ser Gly Thr Gly Tyr Arg Thr Tyr Tyr Ala Asp Ser Val
    50                  55                  60

Lys Gly Arg Phe Thr Ile Ser Arg Asp Asn Ser Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Gly Leu Leu Trp Phe Gly Glu Leu Thr Tyr Trp Gly
            100                 105                 110

Gln Gly Thr Leu Val Thr Val Ser Ser
        115                 120

<210> SEQ ID NO 181
<211> LENGTH: 24
<212> TYPE: DNA
<213> ORGANISM: Artificial Sequence
<220> FEATURE:
<223> OTHER INFORMATION: Synthetic

<210> SEQ ID NO 181

```
<400> SEQUENCE: 181
ggattcacct ttagcaccta tgcc                                           24
```

<210> SEQ ID NO 182
<211> LENGTH: 8
<212> TYPE: PRT
<213> ORGANISM: Artificial Sequence
<220> FEATURE:
<223> OTHER INFORMATION: Synthetic

```
<400> SEQUENCE: 182

Gly Phe Thr Phe Ser Thr Tyr Ala
1               5
```

<210> SEQ ID NO 183
<211> LENGTH: 24
<212> TYPE: DNA
<213> ORGANISM: Artificial Sequence
<220> FEATURE:
<223> OTHER INFORMATION: Synthetic

```
<400> SEQUENCE: 183
attagtggta ctggttatag aaca                                           24
```

<210> SEQ ID NO 184
<211> LENGTH: 8
<212> TYPE: PRT
<213> ORGANISM: Artificial Sequence
<220> FEATURE:
<223> OTHER INFORMATION: Synthetic

```
<400> SEQUENCE: 184

Ile Ser Gly Thr Gly Tyr Arg Thr
1               5
```

<210> SEQ ID NO 185
<211> LENGTH: 42
<212> TYPE: DNA
<213> ORGANISM: Artificial Sequence
<220> FEATURE:
<223> OTHER INFORMATION: Synthetic

```
<400> SEQUENCE: 185
gcgaaagatc ggggcttact atggttcggg gaattaacct ac                       42
```

<210> SEQ ID NO 186
<211> LENGTH: 14
<212> TYPE: PRT
<213> ORGANISM: Artificial Sequence
<220> FEATURE:
<223> OTHER INFORMATION: Synthetic

```
<400> SEQUENCE: 186

Ala Lys Asp Arg Gly Leu Leu Trp Phe Gly Glu Leu Thr Tyr
1               5                   10
```

<210> SEQ ID NO 187
<211> LENGTH: 318
<212> TYPE: DNA
<213> ORGANISM: Artificial Sequence
<220> FEATURE:
<223> OTHER INFORMATION: Synthetic

```
<400> SEQUENCE: 187
gacatccaga tgacccagtc tccttccacc ctgtctgcat ctgtaggaga cagagtcacc    60
```

```
atcacttgcc gggccagtca gagtattaat aactggttgg cctggtatca acagaaacca    120
gggaaggccc ctaacctcct gatctataag gcgtctagtt tagaaagtgg ggtcccatca    180
aggttcagcg gcagtggatc tgggacagaa ttcactctca ccatcagcag cctgcagcct    240
gatgattttg caacttatta ctgccaacaa tataatgatt attggacgtt cggccaaggg    300
accaaggtgg aaatcaaa                                                  318
```

<210> SEQ ID NO 188
<211> LENGTH: 106
<212> TYPE: PRT
<213> ORGANISM: Artificial Sequence
<220> FEATURE:
<223> OTHER INFORMATION: Synthetic

<400> SEQUENCE: 188

```
Asp Ile Gln Met Thr Gln Ser Pro Ser Thr Leu Ser Ala Ser Val Gly
  1               5                  10                  15

Asp Arg Val Thr Ile Thr Cys Arg Ala Ser Gln Ser Ile Asn Asn Trp
             20                  25                  30

Leu Ala Trp Tyr Gln Gln Lys Pro Gly Lys Ala Pro Asn Leu Leu Ile
         35                  40                  45

Tyr Lys Ala Ser Ser Leu Glu Ser Gly Val Pro Ser Arg Phe Ser Gly
     50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr Asn Asp Tyr Trp Thr
                 85                  90                  95

Phe Gly Gln Gly Thr Lys Val Glu Ile Lys
            100                 105
```

<210> SEQ ID NO 189
<211> LENGTH: 18
<212> TYPE: DNA
<213> ORGANISM: Artificial Sequence
<220> FEATURE:
<223> OTHER INFORMATION: Synthetic

<400> SEQUENCE: 189

```
cagagtatta ataactgg                                                   18
```

<210> SEQ ID NO 190
<211> LENGTH: 6
<212> TYPE: PRT
<213> ORGANISM: Artificial Sequence
<220> FEATURE:
<223> OTHER INFORMATION: Synthetic

<400> SEQUENCE: 190

```
Gln Ser Ile Asn Asn Trp
  1               5
```

<210> SEQ ID NO 191
<211> LENGTH: 9
<212> TYPE: DNA
<213> ORGANISM: Artificial Sequence
<220> FEATURE:
<223> OTHER INFORMATION: Synthetic

<400> SEQUENCE: 191

```
aaggcgtct                                                              9
```

```
<210> SEQ ID NO 192
<211> LENGTH: 3
<212> TYPE: PRT
<213> ORGANISM: Artificial Sequence
<220> FEATURE:
<223> OTHER INFORMATION: Synthetic

<400> SEQUENCE: 192

Lys Ala Ser
 1

<210> SEQ ID NO 193
<211> LENGTH: 24
<212> TYPE: DNA
<213> ORGANISM: Artificial Sequence
<220> FEATURE:
<223> OTHER INFORMATION: Synthetic

<400> SEQUENCE: 193
caacaatata atgattattg gacg                                              24

<210> SEQ ID NO 194
<211> LENGTH: 8
<212> TYPE: PRT
<213> ORGANISM: Artificial Sequence
<220> FEATURE:
<223> OTHER INFORMATION: Synthetic

<400> SEQUENCE: 194

Gln Gln Tyr Asn Asp Tyr Trp Thr
 1               5
```

ANTI-ANGPTL3 ANTIBODIES AND USES THEREOF

CROSS-REFERENCE TO RELATED APPLICATIONS

This application is a divisional of U.S. patent application Ser. No. 13/517,662 filed Jun. 14, 2012, now U.S. Pat. No. 9,018,356, entitled "Anti-ANGPTL3 Antibodies and Uses Thereof," which claims the benefit under 35 U.S.C. § 119(e) of U.S. provisional application No. 61/498,518, filed on Jun. 17, 2011; and 61/578,309, filed on Dec. 21, 2011, the disclosures of which are herein incorporated by reference in their entireties.

FIELD OF THE INVENTION

The present invention is related to human antibodies and antigen-binding fragments of human antibodies that specifically bind human angiopoietin-like protein 3 (hANGPTL3), and therapeutic methods of using those antibodies.

BACKGROUND

The angiopoietin-like protein 3 (ANGPTL3) gene was identified from the EST database based on signal sequences and amphipathic helices, and a full-length ANGPTL3 cDNA was subsequently isolated from a human fetal liver/spleen cDNA library (Conklin et al., 1999, *Genomics* 62: 477-482). The deduced 460-amino acid hANGPTL3 protein shares 76% amino acid sequence identity with mouse ANGPTL3 and has the characteristic structure of angiopoietins; i.e., a signal peptide, an extended helical domain predicted to form dimeric or trimeric coiled-coils, a short linker peptide, and a globular fibrinogen homology domain (FD) (Conklin et al., 1999, supra). ANGPTL3 contains the 4 conserved cysteine residues implicated in the intramolecular disulfide bonds within the FD; however, ANGPTL3 contains neither the two additional cysteines nor the characteristic calcium-binding motif found in the FDs of angiopoietins (ANGs; i.e., ANG1, ANG2 and ANG4) (Conklin et al., 1999, supra), which are protein growth factors that promote angiogenesis. In addition, unlike ANGs, ANGPTL3 does not bind to Tie2; however, it may also induce angiogenesis by binding to integrin $\alpha_v\beta_3$ via its C-terminal FD (Camenisch et al., 2002, *J Biol Chem* 277:17281-17290).

Comprehensive in vivo data were obtained from the outbred KK mouse model, which is moderately obese with abnormally high levels of plasma insulin, glucose, and lipids, resembling type 2 diabetes mellitus in humans (Koishi et al., 2002, *Nature Genetics* 30:151-157). One sub-strain of mouse, the KK/San, however, was found to exhibit abnormally low plasma lipid levels (hypolipidemia), which were inherited as a Mendelian recessive. The loci was mapped to chromosome 4 and eventually identified to be the gene encoding ANGPTL3, which contained a 4-bp nucleotide sequence insertion in exon 6 (Koishi et al., 2002, supra). Conversely, plasma lipid levels increase after adenovirus-mediated transfer of ANGPTL3 gene, or after administration of recombinant human ANGPTL3 in KK/San mice. This effect was not mediated by changes in genes involved in cholesterol synthesis, lipoprotein clearance or NEFA oxidation (Koishi et al., 2002, supra). Further, in vitro analysis of recombinant protein showed that ANGPTL3 directly inhibits lipoprotein lipase (LPL) activity, indicating that it is a lipid metabolism modulator that regulates very low density lipoprotein (VLDL) triglyceride levels through the inhibition of LPL activity (Shimizugawa et al., 2002, *J Biol Chem* 277(37):33742-33748). It has been shown that the N-terminal coiled-coil domain, especially the N-terminal region residues 17-165, and not the C-terminal FD, of ANGPTL3, is required for its activity of increasing plasma triglyceride levels in mice (Ono et al., 2003, *J Biol Chem* 278:41804-41809).

The amino acid and nucleotide sequences of human ANGPTL3 are shown in SEQ ID NOS:161 and 162, respectively. Antibodies to ANGPTL3 are disclosed in, for example, WO2008/073300 and U.S. Pat. No. 7,935,796.

BRIEF SUMMARY OF THE INVENTION

In a first aspect, the invention provides fully human monoclonal antibodies (mAbs) and antigen-binding fragments thereof that specifically bind and neutralize, inhibit, block, abrogate, reduce or interfere with, at least one activity of ANGTPL3, in particular, human ANGPTL3 (SEQ ID NO:161). The activity of ANGPTL3 that can be neutralized, inhibited, blocked, abrogated, reduced or interfered with, by the antibodies or fragments thereof of the invention, includes, but not by the way of limitation, inhibition of LPL activity, induction of angiogenesis, and the like. In one embodiment, an antibody or fragment thereof of the present invention can neutralize, inhibit, block, abrogate, reduce or interfere with, an activity of hANGPTL3 by binding to an epitope of hANGPTL3 that is directly involved in the targeted activity of hANGPTL3. In another embodiment, an antibody or fragment thereof of the invention can neutralize, inhibit, block, abrogate, reduce or interfere with, an activity of hANGPTL3 by binding to an epitope of hANGPTL3 that is not directly involved in the targeted activity of hANGPTL3, but the antibody or fragment binding thereto sterically or conformationally inhibits, blocks, abrogates, reduces or interferes with, the targeted activity of hANGPTL3. In yet another embodiment, an antibody or fragment thereof of the invention binds to an epitope of hANGPTL3 that is not directly involved in the targeted activity (e.g., inhibiting LPL activity, inducing angiogenesis, and the like) of hANGPTL3 (i.e., a non-blocking antibody), but the antibody or fragment binding thereto results in the enhancement of the clearance of hANGPTL3 from the circulation, compared to the clearance of hANGPTL3 in the absence of the antibody or fragment thereof, thereby indirectly inhibiting, blocking, abrogating, reducing or interfering with, an activity of hANGPTL3. Clearance of hANGPTL3 from the circulation can be particularly enhanced by combining two or more different non-blocking antibodies that do not compete with one another for specific binding to hANGPTL3.

The antibodies (Abs) can be full-length (for example, an IgG1 or IgG4 antibody) or may comprise only an antigen-binding portion (for example, a Fab, F(ab')$_2$ or scFv fragment), and may be modified to affect functionality, e.g., to eliminate residual effector functions (Reddy et al., 2000, *J. Immunol.* 164:1925-1933).

In one embodiment, the invention comprises an antibody or antigen-binding fragment of an antibody comprising a heavy chain variable region (HCVR) selected from the group consisting of SEQ ID NO:2, 18, 34, 50, 66, 82, 98, 114, 130, 146 and 180, or a substantially similar sequence thereof having at least 90%, at least 95%, at least 98% or at least 99% sequence identity. In another embodiment, the antibody or antigen-binding fragment thereof comprises a HCVR having an amino acid sequence selected from the group consisting of SEQ ID NO:2, 18, 34, 66, 82, 114, and 180. In yet another embodiment, the antibody or an antigen-binding fragment thereof comprises a HCVR having an amino acid sequence of SEQ ID NO:66.

In one embodiment, an antibody or antigen-binding fragment of an antibody comprises a light chain variable region (LCVR) selected from the group consisting of SEQ ID NO:10, 26, 42, 58, 74, 90, 106, 122, 138, 154 and 188, or a substantially similar sequence thereof having at least 90%, at least 95%, at least 98% or at least 99% sequence identity. In another embodiment, the antibody or antigen-binding portion of an antibody comprises a LCVR having an amino acid sequence selected from the group consisting of SEQ ID NO:10, 26, 42, 74, 90, 122 and 188. In yet another embodiment, the antibody or antigen-binding portion of an antibody comprises a LCVR having an amino acid sequence of SEQ ID NO: 74.

In further embodiments, the antibody or fragment thereof comprises a HCVR and LCVR sequence pair (HCVR/LCVR) selected from the group consisting of SEQ ID NO:2/10, 18/26, 34/42, 50/58, 66/74, 82/90, 98/106, 114/122, 130/138, 146/154 and 180/188. In one embodiment, the antibody or fragment thereof comprises a HCVR and LCVR sequence pair selected from the group consisting of SEQ ID NO:2/10, 18/26, 34/42, 66/74, 82/90, 114/122 and 180/188. In another embodiment, the antibody or fragment thereof comprises a HCVR and LCVR sequence pair of SEQ ID NO:66/74.

In a second aspect, the invention features an antibody or antigen-binding fragment of an antibody comprising a heavy chain complementarity determining region 3 (HCDR3) amino acid sequence selected from the group consisting of SEQ ID NO:8, 24, 40, 56, 72, 88, 104, 120, 136, 152 and 186, or a substantially similar sequence thereof having at least 90%, at least 95%, at least 98% or at least 99% sequence identity; and a light chain CDR3 (LCDR3) amino acid sequence selected from the group consisting of SEQ ID NO:16, 32, 48, 64, 80, 96, 112, 128, 144, 160 and 194, or substantially similar sequences thereof having at least 90%, at least 95%, at least 98% or at least 99% sequence identity. In one embodiment, the antibody or fragment thereof comprises a HCDR3/LCDR3 amino acid sequence pair comprising SEQ ID NO:8/16, 24/32, 40/48, 56/64, 72/80, 88/96, 104/112, 120/128, 136/144, 152/160 or 186/194. In another embodiment, the antibody or fragment thereof comprises a HCDR3/LCDR3 amino acid sequence pair comprising SEQ ID NO:8/16, 24/32, 40/48, 72/80, 88/96, 120/128 or 186/194. In yet another embodiment, the antibody or fragment thereof comprises a HCDR3/LCDR3 amino acid sequence pair comprising SEQ ID NO:72/80.

In a further embodiment, the antibody or fragment thereof further comprises a heavy chain CDR1 (HCDR1) amino acid sequence selected from the group consisting of SEQ ID NO:4, 20, 36, 52, 68, 84, 100, 116, 132, 148 and 182, or a substantially similar sequence thereof having at least 90%, at least 95%, at least 98% or at least 99% sequence identity; and a heavy chain CDR2 (HCDR2) amino acid sequence selected from the group consisting of SEQ ID NO:6, 22, 38, 54, 70, 86, 102, 118, 134, 150 and 184, or a substantially similar sequence thereof having at least 90%, at least 95%, at least 98% or at least 99% sequence identity; and optionally further comprises a light chain CDR1 (LCDR1) amino acid sequence selected from the group consisting of SEQ ID NO:12, 28, 44, 60, 76, 92, 108, 124, 140, 156 and 190, or a substantially similar sequence thereof having at least 90%, at least 95%, at least 98% or at least 99% sequence identity; and/or a light chain CDR2 (LCDR2) amino acid sequence selected from the group consisting of SEQ ID NO:14, 30, 46, 62, 78, 94, 110, 126, 142, 158 and 192, or a substantially similar sequence thereof having at least 90%, at least 95%, at least 98% or at least 99% sequence identity.

Alternatively, the invention features an antibody or antigen-binding fragment of an antibody comprising a HCDR1/HCDR2/HCDR3 combination selected from the group consisting of SEQ ID NO:4/6/8, 20/22/24, 36/38/40, 52/54/56, 68/70/72, 84/86/88, 100/102/104, 116/118/120, 132/134/136, 148/150/152 and 182/184/186; and/or a LCDR1/LCDR2/LCDR3 combination selected from the group consisting of SEQ ID NO:12/14/16, 28/30/32, 44/46/48, 60/62/64, 76/78/80, 92/94/96, 108/110/112, 124/126/128, 140/142/144, 156/158/160 and 190/192/194. In one embodiment, the heavy and light chain CDR amino acid sequences comprise a CDR sequence combination selected from the group consisting of SEQ ID NO:4/6/8/12/14/16, 20/22/24/28/30/32, 36/38/40/44/46/48, 52/54/56/60/62/64, 68/70/72/76/78/80, 84/86/88/92/94/96, 100/102/104/108/110/112, 116/118/120/124/126/128, 132/134/136/140/142/144, 148/150/152/156/158/160 and 182/184/186/190/192/194. In one embodiment, the heavy and light chain CDR amino acid sequences comprise a CDR sequence combination of SEQ ID NO: 4/6/8/12/14/16, 20/22/24/28/30/32, 36/38/40/44/46/48, 68/70/72/76/78/80, 84/86/88/92/94/96, 116/118/120/124/126/128 or 182/184/186/190/192/194. In another embodiment, the heavy and light chain CDR amino acid sequences comprise a CDR sequence combination of SEQ ID NO:68/70/72/76/78/80.

In a related embodiment, the invention comprises an antibody or antigen-binding fragment of an antibody which specifically binds hANGPTL3, wherein the antibody or fragment thereof comprises heavy and light chain CDR domains contained within HCVR/LCVR pairs selected from the group consisting of SEQ ID NO:2/10, 18/26, 34/42, 50/58, 66/74, 82/90, 98/106, 114/122, 130/138, 146/154 and 180/188. Methods and techniques for identifying CDRs within HCVR and LCVR amino acid sequences are known in the art and can be applied to identify CDRs within the specified HCVR and/or LCVR amino acid sequences disclosed herein. Conventional definitions that can be applied to identify the boundaries of CDRs include the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, "Sequences of Proteins of Immunological Interest," National Institutes of Health, Bethesda, Md. (1991); Al-Lazikani et al., *J. Mol. Biol.* 273:927-948 (1997); and Martin et al., *Proc. Natl. Acad. Sci. USA* 86:9268-9272 (1989). Public databases are also available for identifying CDR sequences within an antibody. In one embodiment, the antibody or fragment thereof comprises CDR sequences contained within a HCVR and LCVR pair of SEQ ID NO: 2/10, 18/26, 34/42, 66/74, 82/90, 114/122 or 180/188. In another embodiment, the antibody or fragment thereof comprises CDR sequences contained within a HCVR and LCVR pair of SEQ ID NO:66/74.

In another related embodiment, the invention provides an antibody or antigen-binding fragment thereof that competes for specific binding to hANGPTL3 with an antibody or antigen-binding fragment comprising heavy and light chain CDR sequences contained in a HCVR/LCVR sequence pair of SEQ ID NO:2/10, 18/26, 34/42, 50/58, 66/74, 82/90, 98/106, 114/122, 130/138, 146/154 or 180/188. In one embodiment, the antibody or antigen-binding fragment of the invention competes for specific binding to hANGPTL3 with an antibody or fragment thereof comprising a HCVR/ LCVR sequence pair of SEQ ID NO:66/74. In another embodiment, the antibody or antigen-binding fragment of the invention competes for specific binding to hANGPTL3 with an antibody or fragment thereof comprising a heavy and light chain CDR sequence combination selected from the group consisting of 4/6/8/12/14/16, 20/22/24/28/30/32, 36/38/40/44/46/48, 52/54/56/60/62/64, 68/70/72/76/78/80, 84/86/88/92/94/96, 100/102/104/108/110/112, 116/118/120/ 124/126/128, 132/134/136/140/142/144, 148/150/152/156/ 158/160 and 182/184/186/190/192/194. In one embodiment, the antibody or antigen-binding fragment thereof of the invention competes for specific binding to hANGPTL3 with an antibody or fragment thereof comprising a heavy and light chain CDR sequence combination of SEQ ID NOS: 68/70/72/76/78/80.

In another related embodiment, the invention provides an antibody or antigen-binding fragment thereof that binds the same epitope on hANGPTL3 that is recognized by an antibody or fragment thereof comprising heavy and light chain CDR sequences from a HCVR/LCVR sequence pair of SEQ ID NO:2/10, 18/26, 34/42, 50/58, 66/74, 82/90, 98/106, 114/122, 130/138, 146/154 or 180/188. In one embodiment, the antibody or antigen-biding fragment of the invention binds the same epitope on hANGPTL3 as that recognized by the antibody or fragment thereof comprising a HCVR/LCVR sequence pair of SEQ ID NO:66/74. In one embodiment, the antibody or fragment thereof of the invention binds the same epitope on hANGPTL3 that is recognized by an antibody or fragment thereof comprising a heavy and light chain CDR sequence combination selected from the group consisting of 4/6/8/12/14/16, 20/22/24/28/ 30/32, 36/38/40/44/46/48, 52/54/56/60/62/64, 68/70/72/76/ 78/80, 84/86/88/92/94/96, 100/102/104/108/110/112, 116/ 118/120/124/126/128, 132/134/136/140/142/144, 148/150/ 152/156/158/160 and 182/184/186/190/192/194. In one embodiment, such an epitope is recognized by an antibody or fragment thereof comprising a heavy and light chain CDR sequence combination of SEQ ID NO:68/70/72/76/78/80.

In a third aspect, the invention features an isolated anti-hANGPTL3 antibody or antigen-binding fragment thereof that binds to an epitope situated within the N-terminal coiled-coil region at residues 17 to 209 of SEQ ID NO:161 and neutralizes, inhibits, abrogates, reduces or interferes with, at least one activity of hANGPTL3. In another embodiment, the invention provides an isolated antibody or antigen-binding fragment of an antibody that specifically binds to an epitope situated within the N-terminal coiled-coil region of hANGPTL3 (SEQ ID NO:161) and neutralizes, inhibits, abrogates, reduces or interferes with, at least one activity of hANGPTL3, with the proviso that the antibody or fragment thereof does not bind to the ANGPTL3 peptide of SEQ ID NO:170 (corresponds to residues Glu32 to Leu57 of hANGPTL3 of SEQ ID NO:161). In one embodiment, the antibody or fragment thereof of the invention specifically binds to an epitope within residues 17 to 200, 17 to 100, 17 to 70, 17 to 65, 17 to 60, 17 to 57, or 17 to 50, of hANGPTL3 (SEQ ID NO:161), optionally with the proviso that the antibody or fragment thereof does not bind to the ANGPTL3 peptide of SEQ ID NO:170. In another embodiment, the antibody or fragment thereof specifically binds to an epitope within residues 40 to 200, 40 to 100, 40 to 70, 50 to 200, 50 to 100, 50 to 70, 58 to 200, 58 to 100, 58 to 70, 58 to 68, or 61 to 66, of hANGPTL3 (SEQ ID NO:161), optionally with the proviso that the antibody or fragment thereof does not bind to the ANGPTL3 peptide of SEQ ID NO:170. In some embodiments, the antibody or antibody fragment binds an epitope which may involve more than one of the enumerated epitopes or residues within the N-terminal coiled-coil region of hANGPTL3, optionally with the proviso that the antibody or fragment thereof does not bind to the ANGPTL3 peptide of SEQ ID NO:170.

In a fourth aspect, the invention provides nucleic acid molecules encoding anti-ANGPTL3 antibodies or fragments thereof, in particular, any one of those described above. Recombinant expression vectors carrying the nucleic acids of the invention, and host cells, e.g., bacterial cells, such as E. coli, or mammalian cells, such as CHO cells, into which such vectors have been introduced, are also encompassed by the invention, as are methods of producing the antibodies by culturing the host cells under conditions permitting production of the antibodies, and recovering the antibodies produced.

In one embodiment, the invention provides an antibody or fragment thereof comprising a HCVR encoded by a nucleic acid sequence selected from the group consisting of SEQ ID NO: 1, 17, 33, 49, 65, 81, 97, 113, 129, 145 and 179, or a substantially identical sequence having at least 90%, at least 95%, at least 98%, or at least 99% homology thereof. In another embodiment, the antibody or fragment thereof comprises a HCVR encoded by a nucleic acid sequence of SEQ ID NO:1, 17, 33, 65, 81, 113 or 179. In yet another embodiment, the antibody or fragment thereof comprises a HCVR encoded by a nucleic acid sequence of SEQ ID NO:65.

In one embodiment, an antibody or antigen-binding fragment thereof comprises a LCVR encoded by a nucleic acid sequence selected from the group consisting of SEQ ID NO: 9, 25, 41, 57, 73, 89, 105, 121, 137, 153 and 187, or a substantially identical sequence having at least 90%, at least 95%, at least 98%, or at least 99% homology thereof. In another embodiment, the antibody or fragment thereof comprises a LCVR encoded by a nucleic acid sequence of SEQ ID NO:9, 25, 41, 73, 89, 121 or 187. In yet another embodiment, the antibody or fragment thereof comprises a LCVR encoded by a nucleic acid sequence of SEQ ID NO:73.

In further embodiments, the antibody or fragment thereof comprises a HCVR and LCVR (HCVR/LCVR) sequence pair encoded by a nucleic acid sequence pair selected from the group consisting of SEQ ID NO:1/9, 17/25, 33/41, 49/57, 65/73, 81/89, 97/105, 113/121, 129/137, 145/153 and 179/187. In one embodiment, the antibody or fragment thereof comprises a HCVR/LCVR sequence pair encoded by a nucleic acid sequence pair of SEQ ID NO:1/9, 17/25, 33/41, 65/73, 81/89, 113/121 or 179/187. In another embodiment, the antibody or fragment thereof comprises a HCVR/ LCVR sequence pair encoded by a nucleic acid sequence pair of SEQ ID NO:65/73.

In one embodiment, the invention features an antibody or antigen-binding fragment of an antibody comprising a HCDR3 domain encoded by a nucleotide sequence selected from the group consisting of SEQ ID NO:7, 23, 39, 55, 71, 87, 103, 119, 135, 151 and 185, or a substantially identical sequence having at least 90%, at least 95%, at least 98%, or at least 99% homology thereof; and a LCDR3 domain encoded by a nucleotide sequence selected from the group consisting of SEQ ID NO:15, 31, 47, 63, 79, 95, 111, 127, 143, 159 and 193, or a substantially identical sequence having at least 90%, at least 95%, at least 98%, or at least 99% homology thereof. In one embodiment, the antibody or fragment thereof comprises a HCDR3 and LCDR3 sequence pair encoded by the nucleic acid sequence pair selected from the group consisting of SEQ ID NO:7/15, 23/31, 39/47, 55/63, 71/79, 87/95, 103/111, 119/127, 135/143, 151/159 and 185/193. In another embodiment, the antibody or fragment thereof comprises a HCDR3 and LCDR3 sequence pair encoded by the nucleic acid sequence pair of SEQ ID NO:7/15, 23/31, 39/47, 71/79, 87/95, 119/127 or 185/193. In yet another embodiment, the antibody or fragment thereof comprises a HCDR3 and LCDR3 sequence pair encoded by the nucleic acid sequence pair of SEQ ID NO:71/79.

In a further embodiment, the antibody or fragment thereof further comprises a HCDR1 domain encoded by a nucleotide sequence selected from the group consisting of SEQ ID NO: 3, 19, 35, 51, 67, 83, 99, 115, 131, 147 and 181, or a substantially identical sequence having at least 90%, at least 95%, at least 98%, or at least 99% homology thereof; and a HCDR2 domain encoded by a nucleotide sequence selected from the group consisting of SEQ ID NO:5, 21, 37, 53, 69, 85, 101, 117, 133, 149 and 183, or a substantially identical sequence having at least 90%, at least 95%, at least 98%, or at least 99% homology thereof; and optionally further comprises a LCDR1 domain encoded by a nucleotide sequence selected from the group consisting of SEQ ID NO:11, 27, 43, 59, 75, 91, 107, 123, 139, 155 and 189, or a substantially identical sequence having at least 90%, at least 95%, at least 98%, or at least 99% homology thereof; and/or a LCDR2 domain encoded by a nucleotide sequence selected from the group consisting of SEQ ID NO:13, 29, 45, 61, 77, 93, 109, 125, 141, 157 and 191, or a substantially identical sequence having at least 90%, at least 95%, at least 98%, or at least 99% homology thereof.

Alternatively, the invention features an antibody or antigen-binding fragment of an antibody comprising a HCDR1/HCDR2/HCDR3 combination encoded by a nucleotide sequence combination selected from the group consisting of SEQ ID NO:3/5/7, 19/21/23, 35/37/39, 51/53/55, 67/69/71, 83/85/87, 99/101/103, 115/117/119, 131/133/135, 147/149/151 and 181/183/185; and/or a LCDR1/LCDR2/LCDR3 combination encoded by a nucleotide sequence combination selected from the group consisting of SEQ ID NO:11/13/15, 27/29/31, 43/45/47, 59/61/63, 75/77/79, 91/93/95, 107/109/111, 123/125/127, 139/141/143, 155/157/159 and 189/191/193. In one embodiment, the antibody or fragment thereof comprises heavy and light chain CDR sequences encoded by a nucleotide sequence combination of SEQ ID NO:67/69/71/75/77/79.

In a fifth aspect, the invention features a human anti-ANGPTL3 antibody or antigen-binding fragment thereof comprising a heavy chain variable region (HCVR) encoded by nucleotide sequence segments derived from $V_H$, $D_H$ and $J_H$ germline sequences, and a light chain variable region (LCVR) encoded by nucleotide sequence segments derived from $V_K$ and $J_K$ germline sequences, wherein the HCVR and the LCVR are encoded by nucleotide sequence segments derived from a germline gene combination selected from the group consisting of: (i) $V_H$3-43, $D_H$3-3, 43, $V_K$1-5 and $J_K$2; (ii) $V_H$3-11, $D_H$1-1, $J_H$4, $V_K$1-39 and $J_K$4; (iii) $V_H$3-30, $D_H$1-7, $J_H$6, $V_K$1-5 and $J_K$1; (iv) $V_H$3-30, $D_H$1-26, $J_H$6, $V_K$1-12 and $J_K$3; (v) $V_H$3-30, $D_H$3-10, $J_H$6, $V_K$1-12 and $J_K$3; and (vi) $V_H$3-23, $D_H$3-10, $J_H$4, $V_K$1-5 and $J_K$1.

In a sixth aspect, the invention features an antibody or antigen-binding fragment thereof that specifically binds to hANGPTL3 with an equilibrium dissociation constant ($K_D$) of about 7 nM or less, about 6 nM or less, about 5 nM or less, about 4 nM or less, about 3 nM or less, about 2 nM or less, or about 1 nM or less, as measured by surface plasmon resonance assay (for example, BIACORE™). In certain embodiments, the antibody of the invention exhibits a $K_D$ of about 800 pM or less, about 700 pM or less; about 600 pM or less; about 500 pM or less; about 400 pM or less; about 300 pM or less; about 200 pM or less; about 100 pM or less; or about 50 pM or less.

In a seventh aspect, the present invention provides an anti-hANGPTL3 antibody or antigen-binding fragment thereof that binds hANGPTL3 protein of SEQ ID NO:161, but does not cross-react with a related protein, such as a human angiopoietin-like protein 4 (hANGPTL4; SEQ ID NO:164), as determined by, for example, ELISA, surface plasmon resonance assay, or LUMINEX® XMAP® Technology, as described herein. ANGPTL4 is another secreted protein that is known to reduce LPL activity and has an N-terminal coiled-coil region and a C-terminal fibrinogen-like domain (Ge et al., 2004, *J Biol Chem* 279:2038-2045; Yau et al., 2009, *J Biol Chem* 284:11942-11952). In related embodiments, the invention provides an anti-hANGPTL3 antibody or antigen binding fragment thereof that binds a hANGPTL3 protein and cross-reacts with a hANGPTL4 protein. In certain embodiments, the binding affinity of the hANGPTL3 antibody or fragment thereof to hANGPTL4 protein is about 75% or less, or about 50% or less, of the binding affinity of the antibody or fragment to the hANGPTL3 protein.

In another related embodiment, the invention provides an anti-hANGPTL3 antibody or antigen binding fragment thereof that does not cross-react with mouse ANGPTL3 (mANGPTL3; SEQ ID NO:163), or rat ANGPTL3 (rANGPTL3; SEQ ID NO:175), but does cross-react with cynomolgus monkey (*Macaca fascicularis*) ANGPTL3 (MfANGPTL3), for example, with the N-terminal 17-170 residues of SEQ ID NO:177 (a partial amino acid sequence of MfANGPTL3). In yet another related embodiment, the invention provides an anti-hANGPTL3 antibody or fragment thereof that cross-reacts with MfANGPTL3, mANGPTL3 and rANGTPL3.

The invention encompasses anti-hANGPTL3 antibodies having a modified glycosylation pattern. In some applications, modification to remove undesirable glycosylation sites may be useful, or e.g., removal of a fucose moiety to increase antibody dependent cellular cytotoxicity (ADCC) function (see Shield et al. (2002) JBC 277:26733). In other applications, removal of N-glycosylation site may reduce undesirable immune reactions against the therapeutic antibodies, or increase affinities of the antibodies. In yet other applications, modification of galactosylation can be made in order to modify complement dependent cytotoxicity (CDC).

In an eighth aspect, the invention features a pharmaceutical composition comprising a recombinant human antibody or fragment thereof which specifically binds hANGPTL3 and a pharmaceutically acceptable carrier. In one embodiment, the invention provides a pharmaceutical composition comprising one or more anti-ANGPTL3 antibodies or fragments thereof of the invention, which do not cross-compete with one another, and a pharmaceutically acceptable carrier. In one embodiment, the pharmaceutical composition of the invention can contain two or more non-blocking antibodies, which do not compete with one another for specific binding to hANGPTL3 and are effective in clearing hANGPTL3 from the circulation. Suitable combinations of non-blocking antibodies include, but are not limited to, a combination of antibodies comprising HCVR and LCVR sequence pairs (HCVR/LCVR) of: (i) SEQ ID NO:82/90 and 180/188, respectively; (ii) SEQ ID NO:114/122 and 180/188, respectively; (iii) SEQ ID NO:82/90 and 18/26, respectively; or (iv) SEQ ID NO:114/122 and 18/26, respectively.

In related embodiments, the invention features a composition which is a combination of an antibody or antigen-binding fragment thereof of the invention, and a second therapeutic agent. The second therapeutic agent may be one or more of any agent such as (1) 3-hydroxy-3-methylglutaryl-coenzyme A (HMG-CoA) reductase inhibitors, such as cerivastatin, atorvastatin, simvastatin, pitavastatin, rosuvastatin, fluvastatin, lovastatin, pravastatin, and the like; (2) inhibitors of cholesterol uptake and/or bile acid re-absorption; (3) niacin, which increases lipoprotein catabolism; (4) fibrates or amphipathic carboxylic acids, which reduce low-density lipoprotein (LDL) level, improve high-density lipoprotein (HDL) and TG levels, and reduce the number of non-fatal heart attacks; and (5) activators of the LXR transcription factor that plays a role in cholesterol elimination such as 22-hydroxycholesterol, or fixed combinations such as ezetimibe plus simvastatin; a statin with a bile resin (e.g., cholestyramine, colestipol, colesevelam), a fixed combination of niacin plus a statin (e.g., niacin with lovastatin); or with other lipid lowering agents such as omega-3-fatty acid ethyl esters (for example, omacor). Furthermore, the second therapeutic agent can be one or more other inhibitors of ANGPTL3 as well as inhibitors of other molecules, such as ANGPTL4, ANGPTL5, ANGPTL6 and proprotein convertase subtilisin/kexin type 9 (PCSK9), which are involved in lipid metabolism, in particular, cholesterol and/or triglyceride homeostasis. Inhibitors of these molecules include small molecules and antibodies that specifically bind to these molecules and block their activity.

In related embodiments, the second therapeutic agent may be one or more anti-cancer agents, such as chemotherapeutic agents, anti-angiogenic agents, growth inhibitory agents, cytotoxic agents, apoptotic agents, and other agents well known in the art to treat cancer or other proliferative diseases or disorders, as well as other therapeutic agents, such as analgesics, anti-inflammatory agents, including non-steroidal anti-inflammatory drugs (NSAIDS), such as Cox-2 inhibitors, and the like, so as to ameliorate and/or reduce the symptoms accompanying the underlying cancer/tumor.

In a ninth aspect, the invention features methods for neutralizing, inhibiting, blocking, abrogating, reducing or interfering with, hANGPTL3 activity using one or more anti-hANGPTL3 antibodies or antigen-binding fragments thereof of the invention. In one embodiment, the invention provides a therapeutic method comprising administering to a subject in need thereof a therapeutically effective amount of a pharmaceutical composition comprising one or more anti-hANGPTL3 antibodies or antigen-binding fragments thereof of the invention and, optionally one or more additional therapeutic agents described above. The anti-ANGPTL3 antibodies or fragments thereof of the invention may be neutralizing antibodies or non-blocking antibodies against ANGPTL3, or combinations thereof.

In related embodiments, the invention provides methods of enhancing the clearance of hANGPTL3 from the circulation of a subject in need thereof, comprising administering to the subject at least two anti-hANGPTL3 antibodies or fragments thereof of the invention that do not compete with one another for binding to hANGPTL3 and preferably do not block at least one activity of hANGPTL3 (i.e., non-blocking antibodies). At least one activity of hANGPTL3 referred to includes, but not the way of limitation, inhibiting LPL activity, inducing angiogenesis, and the like. In one embodiment, a combination of at least two non-blocking anti-hANGPTL3 antibodies or fragments thereof enhances the clearance of hANGPTL3 from the circulation by at least about 20%, about 30%, about 40%, about 50%, about 60%, about 70%, or about 80%, relative to not administering the antibodies or fragments. Circulating levels of hANGPTL3 can be measured by in vitro assays well known in the art and those described herein. In another embodiment, the combination of at least two non-blocking anti-hANGPTL3 antibodies comprises HCVR and LCVR sequence pairs (HCVR/LCVR) of: (i) SEQ ID NO:82/90 and 180/188, respectively; (ii) SEQ ID NO:114/122 and 180/188, respectively; (iii) SEQ ID NO:82/90 and 18/26, respectively; or (iv) SEQ ID NO:114/122 and 18/26, respectively.

The disease or disorder treatable by the methods of the invention is any disease or condition which is improved, ameliorated, inhibited or prevented, or its occurrence rate reduced, compared to that without anti-hANGPTL3 antibody treatment (e.g., ANGPTL3-mediated diseases or disorders), by removing, inhibiting, reducing, or otherwise interfering with, ANGPTL3 activity. Examples of diseases or disorders treatable by the methods of the invention include, but are not limited to, those involving lipid metabolism, such as hyperlipidemia, hyperlipoproteinemia and dyslipidemia, including atherogenic dyslipidemia, diabetic dyslipidemia, hypertriglyceridemia, including severe hypertriglyceridemia with TG>1000 mg/dL, hypercholesterolemia, chylomicronemia, mixed dyslipidemia (obesity, metabolic syndrome, diabetes, etc.), lipodystrophy, lipoatrophy, and the like, which are caused by, for example, decreased LPL activity and/or LPL deficiency, decreased LDL receptor (LDLR) activity and/or LDL receptor deficiency (e.g., homozygous familial hypercholesterolemia with LDLR$^{-/-}$), altered ApoC2, ApoE deficiency, increased ApoB, increased production and/or decreased elimination of very low-density lipoprotein (VLDL), certain drug treatment (e.g., glucocorticoid treatment-induced dyslipidemia), any genetic predisposition, diet, life style, and the like. The methods of the invention can also prevent or treat diseases or disorders associated with or resulting from hyperlipidemia, hyper-lipoproteinemia, and/or dyslipidemia, including, but not limited to, cardiovascular diseases or disorders, such as atherosclerosis, aneurysm, hypertension, angina, stroke, cerebrovascular diseases, congestive heart failure, coronary artery diseases, myocardial infarction, peripheral vascular diseases, and the like; acute pancreatitis; nonalcoholic steatohepatitis (NASH); blood sugar disorders, such as diabetes; obesity, and the like.

Other examples of diseases or disorders treatable by the methods of the invention include cancer/tumor as well as non-neoplastic angiogenesis-associated diseases or disorders, including ocular angiogenic diseases or disorders, such as age-related macular degeneration, central retinal vein occlusion or branch retinal vein occlusion, diabetic retinopathy, retinopathy of prematurity, and the like, inflammatory diseases or disorders, such as arthritis, rheumatoid arthritis (RA), psoriasis, and the like.

Other embodiments will become apparent from a review of the ensuing detailed description.

BRIEF DESCRIPTION OF THE FIGURES

FIG. 1 shows a sequence alignment of Peptides 1-3 used in an anti-hANGPTL3 antibody binding experiment (Example 5) against the relevant portions of hANGPTL3 sequence (i.e., within residues 30 to 70 of SEQ ID NO:161 or GenBank #NP_055310). Peptide 1 (control: ANGPTL4 peptide; SEQ ID NO:168); Peptide 2 (ANGPTL3 peptide; SEQ ID NO:169); and Peptide 3 (ANGPTL3 peptide; SEQ ID NO:170).

DETAILED DESCRIPTION

Figure 2:
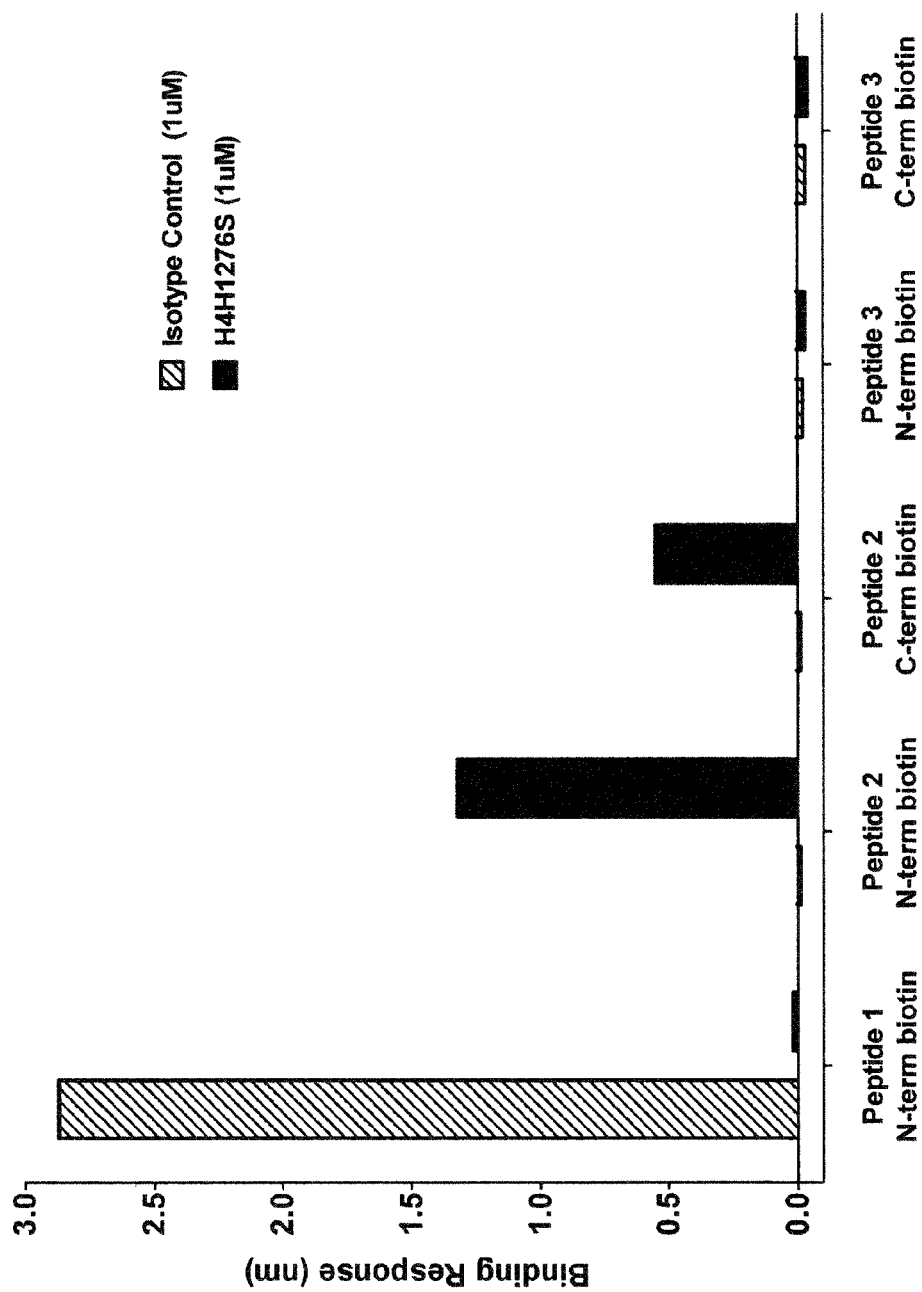
FIG. 2 shows the results of anti-hANGPTL3 antibody binding to the N-terminal coiled-coil peptides of hANGPTL3 (Peptides 2 and 3) or hANGPTL4 (Peptide 1). 要です: Isotype Control; and ■: H4H1276S antibody.

Before the present invention is described in detail, it is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, preferred methods and materials are now described. All publications mentioned herein are incorporated herein by reference in their entirety.

Definitions

The term "human angiopoietin-like protein 3" or "hANGPTL3", as used herein, refers to ANGPTL3 having the nucleic acid sequence shown in SEQ ID NO:162 and the amino acid sequence of SEQ ID NO:161, or a biologically active fragment thereof.

The term "antibody", as used herein, is intended to refer to immunoglobulin molecules comprised of four polypeptide chains, two heavy (H) chains and two light (L) chains inter-connected by disulfide bonds. Each heavy chain is comprised of a heavy chain variable region (HCVR) and a heavy chain constant region ($C_H$; comprised of domains $C_H1$, $C_H2$ and $C_H3$). Each light chain is comprised of a light chain variable region (LCVR) and a light chain constant region (CO. The HCVR and LCVR can be further subdivided into regions of hypervariability, termed complementarity determining regions (CDR), interspersed with regions that are more conserved, termed framework regions (FR). Each HCVR and LCVR is composed of three CDRs and four FRs, arranged from amino-terminus to carboxy-terminus in the following order: FR1, CDR1, FR2, CDR2, FR3, CDR3, and FR4.

Substitution of one or more CDR residues or omission of one or more CDRs is also possible. Antibodies have been described in the scientific literature in which one or two CDRs can be dispensed with for binding. Padlan et al. (1995 FASEB J. 9:133-139) analyzed the contact regions between antibodies and their antigens, based on published crystal structures, and concluded that only about one fifth to one third of CDR residues actually contact the antigen. Padlan also found many antibodies in which one or two CDRs had no amino acids in contact with an antigen (see also, Vajdos et al. 2002 J Mol Biol 320:415-428).

CDR residues not contacting antigen can be identified based on previous studies (for example, residues H60-H65 in CDRH2 are often not required), from regions of Kabat CDRs lying outside Chothia CDRs, by molecular modeling and/or empirically. If a CDR or residue(s) thereof is omitted, it is usually substituted with an amino acid occupying the corresponding position in another human antibody sequence or a consensus of such sequences. Positions for substitution within CDRs and amino acids to substitute can also be selected empirically. Empirical substitutions can be conservative or non-conservative substitutions.

The term "human antibody", as used herein, is intended to include antibodies having variable and constant regions derived from human germline immunoglobulin sequences. The human mAbs of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include mAbs in which CDR sequences derived from the germline of another mammalian species (e.g., mouse), have been grafted onto human FR sequences.

The fully-human anti-hANGPTL3 antibodies disclosed herein may comprise one or more amino acid substitutions, insertions and/or deletions in the framework and/or CDR regions of the heavy and light chain variable domains as compared to the corresponding germline sequences.

Such mutations can be readily ascertained by comparing the amino acid sequences disclosed herein to germline sequences available from, for example, public antibody sequence databases. The present invention includes antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residues(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline back-mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies of the present invention may contain any combination of two or more germline mutations within the framework and/or CDR regions, e.g., wherein certain individual residues are mutated to the corresponding residues of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. Antibodies and antigen-binding fragments obtained in this general manner are encompassed within the present invention.

The present invention also includes anti-ANGPTL3 antibodies comprising variants of any of the HCVR, LCVR, and/or CDR amino acid sequences disclosed herein having one or more conservative substitutions. For example, the present invention includes anti-ANGPTL3 antibodies having HCVR, LCVR, and/or CDR amino acid sequences with, e.g., 10 or fewer, 8 or fewer, 6 or fewer, 4 or fewer, 2 or 1, conservative amino acid substitution(s) relative to any of the HCVR, LCVR, and/or CDR amino acid sequences disclosed herein. In one embodiment, a HCVR comprises the amino acid sequence of SEQ ID NO:487 with 10 or fewer conservative amino acid substitutions therein. In another embodiment, a HCVR comprises the amino acid sequence of SEQ ID NO:487 with 8 or fewer conservative amino acid substitutions therein. In another embodiment, a HCVR comprises the amino acid sequence of SEQ ID NO:487 with 6 or fewer conservative amino acid substitutions therein. In another embodiment, a HCVR comprises the amino acid sequence of SEQ ID NO:487 with 4 or fewer conservative amino acid substitutions therein. In yet another embodiment, a HCVR comprises the amino acid sequence of SEQ ID NO:487 with 2 or 1 conservative amino acid substitution(s) therein. In one embodiment, a LCVR comprises the amino acid sequence of SEQ ID NO:44 with 10 or fewer conservative amino acid substitutions therein. In another embodiment, a LCVR comprises the amino acid sequence of SEQ ID NO:44 with 8 or fewer conservative amino acid substitutions therein. In another embodiment, a LCVR comprises the amino acid sequence of SEQ ID NO:44 with 6 or fewer conservative amino acid substitutions therein. In another embodiment, a LCVR comprises the amino acid sequence of SEQ ID NO:44 with 4 or fewer conservative amino acid substitutions therein. In yet another embodiment, a LCVR comprises the amino acid sequence of SEQ ID NO:44 with 2 or 1 conservative amino acid substitution(s) therein.

Unless specifically indicated otherwise, the term "antibody," as used herein, shall be understood to encompass antibody molecules comprising two immunoglobulin heavy chains and two immunoglobulin light chains (i.e., "full antibody molecules") as well as antigen-binding fragments thereof. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and (optionally) constant domains. Such DNA is known and/or is readily available from, e.g., commercial sources, DNA libraries (including, e.g., phage-display antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H1$; (ii) $V_H$-$C_H2$; (iii) $V_H$-$C_H3$; (iv) $V_H$-$C_H1$-$C_H2$; (V) $V_H$-$C_H1$-$C_H2$-$C_H3$; (VI) $V_H$-$C_H2$-$C_H3$; (vii) $V_H$-$C_L$; (viii) $V_L$-$C_H1$; (iX) $V_L$-$C_H2$; (X) $V_L$-$C_H3$; (xi) $V_L$-$C_H1$-$C_H2$; (XII) $V_L$-$C_H1$-$C_H2$-$C_H3$, (Xiii) $V_L$-$C_H2$-$C_H3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment of an antibody of the present invention may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

As with full antibody molecules, antigen-binding fragments may be monospecific or multispecific (e.g., bispecific). A multispecific antigen-binding fragment of an antibody will typically comprise at least two different variable domains, wherein each variable domain is capable of specifically binding to a separate antigen or to a different epitope on the same antigen. Any multispecific antibody format, including the exemplary bispecific antibody formats disclosed herein, may be adapted for use in the context of an antigen-binding fragment of an antibody of the present invention using routine techniques available in the art.

In certain embodiments, antibody or antibody fragments of the invention may be conjugated to a therapeutic moiety ("immunoconjugate"), such as a cytotoxin, a chemotherapeutic drug, an immunosuppressant or a radioisotope.

The term "specifically binds," or the like, means that an antibody or antigen-binding fragment thereof forms a complex with an antigen that is relatively stable under physiological conditions. Specific binding can be characterized by an equilibrium dissociation constant ($K_D$) of about $1 \times 10^{-6}$ M or less (i.e., a smaller $K_D$ denotes a tighter binding). Methods for determining whether two molecules specifically bind are well known in the art and include, for example, equilibrium dialysis, surface plasmon resonance, and the like. An isolated antibody that specifically binds hANGPTL3 may, however, exhibit cross-reactivity to other antigens, such as ANGPTL3 molecules from other species, for example, cynomolgus monkey ANGPTL3, mouse ANGPTL3, rat ANGPTL3, and/or hANGPTL4 having the amino acid sequence of SEQ ID NO:164. Moreover, multi-specific antibodies (e.g., bispecifics) that bind to hANGPTL3 and one or more additional antigens are nonetheless considered antibodies that "specifically bind" hANGPTL3, as used herein.

The term "high affinity" antibody refers to those antibodies having a binding affinity to hANGPTL3, expressed as $K_D$, of about $2 \times 10^{-9}$ M or less, about $1.5 \times 10^{-9}$ M or less, about $1 \times 10^{-9}$ M or less, about $0.5 \times 10^{-9}$ M or less, about $0.25 \times 10^{-9}$ M or less, about $1 \times 10^{-10}$ M or less, or about $0.5 \times 10^{-10}$ M or less, as measured by surface plasmon resonance, e.g., BIACORE™ or solution-affinity ELISA.

The term "$K_D$", as used herein, is intended to refer to the equilibrium dissociation constant of a particular antibody-antigen interaction.

By the term "slow off rate", "Koff" or "$k_d$" is meant an antibody that dissociates from hANGPTL3 with a rate constant of $4 \times 10^{-3}$ s$^{-1}$ or less, $3 \times 10^{-3}$ s$^{-1}$ or less, $2 \times 10^{-3}$ s$^{-1}$ or less, $1 \times 10^{-3}$ s$^{-1}$ or less, $1 \times 10^{-4}$ s$^{-1}$ or less, as determined by surface plasmon resonance, e.g., BIACORE™.

By the term "intrinsic affinity constant" or "$k_a$" is meant an antibody that associates with hANGPTL3 at a rate constant of about $1 \times 10^3$ M$^{-1}$ s$^{-1}$ or higher, as determined by surface plasmon resonance, e.g., BIACORE™.

An "isolated antibody", as used herein, is intended to refer to an antibody that is substantially free of other mAbs having different antigenic specificities (e.g., an isolated antibody that specifically binds hANGPTL3 is substantially free of mAbs that specifically bind antigens other than hANGPTL3). An isolated antibody that specifically binds hANGPTL3 may, however, have cross-reactivity to other antigens, such as ANGPTL3 molecules from other species, such as cynomolgus monkey, mouse, rat, and/or other related proteins, such as human ANGPTL4.

A "neutralizing", "blocking" or "abrogating" antibody, as used herein (or an antibody that "neutralizes", "blocks" or "abrogates" ANGPTL3 activity), is intended to refer to an antibody whose binding to ANGPTL3 results in direct inhibition of at least one biological activity of ANGPTL3, as assessed by standard in vitro assays known in the art (for example, see Examples below). The terms, "neutralize", "inhibit", "block" and "abrogate", may be used herein interchangeably. A "non-blocking" antibody refers to an antibody whose binding to ANGPTL3 does not directly block a targeted activity of ANGPTL3 as assessed by standard in vitro assays, but yet may be an "interfering" antibody whose binding to ANGPTL3 results in indirect inhibition, reduction, attenuation, or other interference, of at least one biological activity of ANGPTL3 in vivo, e.g., by enhancing the clearance of ANGPTL3 from the circulation. Clearance of ANGPTL3 from the circulation can be particularly enhanced by a combination of at least two non-blocking antibodies. The neutralization, inhibition, abrogation, reduction, attenuation or interference, of a biological activity of ANGPTL3 can be assessed by measuring one or more indicators of ANGPTL3 biological activity by one or more of several standard in vitro or in vivo assays known in the art (also see Examples below).

The term "surface plasmon resonance", as used herein, refers to an optical phenomenon that allows for the analysis of real-time biospecific interactions by detection of alterations in protein concentrations within a biosensor matrix, for example using the BIACORE™ system (Pharmacia Biosensor AB, Uppsala, Sweden and Piscataway, N.J.).

The term "epitope" is a region of an antigen that is bound by an antibody. Epitopes may be defined as structural or functional. Functional epitopes are generally a subset of the structural epitopes and have those residues that directly contribute to the affinity of the interaction. Epitopes may also be conformational, that is, composed of non-linear amino acids. In certain embodiments, epitopes may include determinants that are chemically active surface groupings of molecules such as amino acids, sugar side chains, phosphoryl groups, or sulfonyl groups, and, in certain embodiments, may have specific three-dimensional structural characteristics, and/or specific charge characteristics.

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 90%, and more preferably at least about 95%, 96%, 97%, 98% or 99% of the nucleotide bases, as measured by any well-known algorithm of sequence identity, such as FASTA, BLAST or GAP, as discussed below.

As applied to polypeptides, the term "substantial similarity" or "substantially similar" means that two peptide sequences, when optimally aligned, such as by the programs GAP or BESTFIT using default gap weights, share at least 90% sequence identity, even more preferably at least 95%, 98% or 99% sequence identity. Preferably, residue positions which are not identical differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent or degree of similarity may be adjusted upwards to correct for the conservative nature of the substitution. Means for making this adjustment are well known to those of skill in the art. See, e.g., Pearson (1994) Methods Mol. Biol. 24: 307-331. Examples of groups of amino acids that have side chains with similar chemical properties include 1) aliphatic side chains: glycine, alanine, valine, leucine and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains: aspartate and glutamate, and 7) sulfur-containing side chains: cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443 45. A "moderately conservative" replacement is any change having a nonnegative value in the PAM250 log-likelihood matrix.

Sequence similarity for polypeptides is typically measured using sequence analysis software. Protein analysis software matches similar sequences using measures of similarity assigned to various substitutions, deletions and other modifications, including conservative amino acid substitutions. For instance, GCG software contains programs such as GAP and BESTFIT which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA with default or recommended parameters; a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the invention to a database containing a large number of sequences from different organisms is the computer program BLAST, especially BLASTP or TBLASTN, using default parameters. See, e.g., Altschul et al. (1990) J. Mol. Biol. 215: 403 410 and (1997) Nucleic Acids Res. 25:3389 402.

By the phrase "therapeutically effective amount" is meant an amount that produces the desired effect for which it is administered. The exact amount will depend on the purpose of the treatment, the age and the size of a subject treated, the route of administration, and the like, and will be ascertainable by one skilled in the art using known techniques (see, for example, Lloyd (1999) The Art, Science and Technology of Pharmaceutical Compounding).

Preparation of Human Antibodies

Methods for generating human antibodies in transgenic mice are known in the art. Any such known methods can be used in the context of the present invention to make human antibodies that specifically bind to ANGPTL3.

Using VELOCIMMUNE™ technology or any other known method for generating monoclonal antibodies, high affinity chimeric antibodies to ANGPTL3 are initially isolated having a human variable region and a mouse constant region. As in the experimental section below, the antibodies are characterized and selected for desirable characteristics, including affinity, selectivity, epitope, and the like.

In general, the antibodies of the instant invention possess high affinities, typically possessing $K_D$ of from about $10^{-12}$ M through about $10^{-9}$ M, when measured by binding to antigen either immobilized on solid phase or in solution phase. The mouse constant regions are replaced with desired human constant regions, for example, wild-type IgG1 or IgG4, or modified IgG1 or IgG4, to generate the fully human antibodies of the invention. While the constant region selected may vary according to specific use, high affinity antigen-binding and target specificity characteristics of the antibodies reside in the variable region.

Epitope Mapping and Related Technologies

To screen for antibodies that bind to a particular epitope, a routine cross-blocking assay such as that described in *Antibodies*, Harlow and Lane (Cold Spring Harbor Press, Cold Spring Harb., N.Y.) can be performed. Other methods include alanine scanning mutants, peptide blots (Reineke (2004) Methods Mol Biol 248:443-63), or peptide cleavage analysis. In addition, methods such as epitope excision, epitope extraction and chemical modification of antigens can be employed (Tomer (2000) Protein Science 9: 487-496).

The term "epitope" refers to a site on an antigen to which B and/or T cells respond. B-cell epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, and more usually, at least 5 or 8-10 amino acids in a unique spatial conformation.

Modification-Assisted Profiling (MAP), also known as Antigen Structure-based Antibody Profiling (ASAP) is a method that categorizes large numbers of monoclonal antibodies (mAbs) directed against the same antigen according to the similarities of the binding profile of each antibody to chemically or enzymatically modified antigen surfaces (US 2004/0101920). Each category may reflect a unique epitope either distinctly different from or partially overlapping with epitope represented by another category. This technology allows rapid filtering of genetically identical mAbs, such that characterization can be focused on genetically distinct mAbs. When applied to hybridoma screening, MAP may facilitate identification of rare hybridoma clones that produce mAbs having the desired characteristics. MAP may be used to sort the anti-ANGPTL3 mAbs of the invention into groups of mAbs binding different epitopes.

ANGPTL3 contains an amino-terminal coiled-coil domain and a carboxyl-terminal fibrinogen like domain (FD) and the ANGPTL3 protein forms an oligomer in the absence of intermolecular disulfide bonds (Ge et al., 2005, *J Lipid Res* 46:1484-1490). It has been reported that the N-terminal coiled-coil domain is important in the inhibition of LPL activity (Ono et al., 2003, *J Biol Chem* 278:41804-41809). Thus, in certain embodiments, the anti-hANGPTL3 antibody or antigen-binding fragment of an antibody binds an epitope within the N-terminal coiled-coil domain (residues 17-209) of hANGPTL3 (SEQ ID NO:161) and neutralizes at least one activity of hANGPTL3 (e.g., inhibition of LPL activity). In another embodiments, the anti-hANGPTL3 antibody or antigen-binding fragment thereof binds an epitope within the N-terminal coiled-coil domain of hANGPTL3 and neutralizes at least one activity of hANGPTL3, with the proviso that the antibody or fragment thereof does not bind to the ANGPTL3 peptide of SEQ ID NO:170. In one embodiment, the antibody or fragment thereof specifically binds an epitope within residues 17 to 200, 17 to 100, 17 to 70, 17 to 65, 17 to 60, 17 to 57, 17 to 55, 17 to 50, 17 to 45, 17 to 40, or 17 to 35, of hANGPTL3 (SEQ ID NO:161), optionally with the proviso that the antibody or fragment thereof does not bind to the ANGPTL3 peptide of SEQ ID NO:170. In another embodiment, the antibody or fragment thereof specifically binds an epitope within residues 40 to 200, 40 to 100, 40 to 70, 50 to 200, 50 to 100, 50 to 70, 58 to 200, 58 to 100, 58 to 70, 58 to 68, or 61 to 66 (known as a "heparin-binding motif") of hANGPTL3 (SEQ ID NO:161), optionally with the proviso that the antibody or fragment thereof does not bind to the ANGPTL3 peptide of SEQ ID NO:170. In some embodiments, the antibody or antibody fragment binds an epitope which may involve more than one of the enumerated epitopes or residues within the N-terminal coiled-coil region of hANGPTL3, optionally with the proviso that the antibody or fragment thereof does not bind to the ANGPTL3 peptide of SEQ ID NO:170.

In other embodiments, hANGPTL3 antibody or fragment thereof binds one or more fragments of hANGPTL3, for example, a fragment of at least 5 residues, at least 7 residues, at least 10 residues, at least 20 residues, at least 30 residues, at least 50 residues, at least 70 residues, at least 100 residues, at least 150 residues, or at least 200 residues, of hANGPTL3

(SEQ ID NO:161), optionally with the proviso that the antibody or fragment thereof does not bind to the ANGPTL3 peptide of SEQ ID NO:170.

The present invention includes hANGPTL3 antibodies that bind to the same epitope as any of the specific exemplary antibodies described herein. Likewise, the present invention also includes anti-hANGPTL3 antibodies that compete for binding to hANGPTL3 or a hANGPTL3 fragment with any of the specific exemplary antibodies described herein.

One can easily determine whether an antibody binds to the same epitope as, or competes for binding with, a reference anti-hANGPTL3 antibody by using routine methods known in the art. For example, to determine if a test antibody binds to the same epitope as a reference anti-hANGPTL3 antibody of the invention, the reference antibody is allowed to bind to a hANGPTL3 protein or peptide under saturating conditions. Next, the ability of a test antibody to bind to the hANGPTL3 molecule is assessed. If the test antibody is able to bind to hANGPTL3 following saturation binding with the reference anti-hANGPTL3 antibody, it can be concluded that the test antibody binds to a different epitope than the reference anti-hANGPTL3 antibody. On the other hand, if the test antibody is not able to bind to the hANGPTL3 molecule following saturation binding with the reference anti-hANGPTL3 antibody, then the test antibody may bind to the same epitope as the epitope bound by the reference anti-hANGPTL3 antibody of the invention.

To determine if an antibody competes for binding with a reference anti-hANGPTL3 antibody, the above-described binding methodology is performed in two orientations: In a first orientation, the reference antibody is allowed to bind to a hANGPTL3 molecule under saturating conditions followed by assessment of binding of the test antibody to the hANGPTL3 molecule. In a second orientation, the test antibody is allowed to bind to a hANGPTL3 molecule under saturating conditions followed by assessment of binding of the reference antibody to the ANGPTL3 molecule. If, in both orientations, only the first (saturating) antibody is capable of binding to the ANGPTL3 molecule, then it is concluded that the test antibody and the reference antibody compete for binding to hANGPTL3. As will be appreciated by a person of ordinary skill in the art, an antibody that competes for binding with a reference antibody may not necessarily bind to the identical epitope as the reference antibody, but may sterically block binding of the reference antibody by binding an overlapping or adjacent epitope.

Two antibodies bind to the same or overlapping epitope if each competitively inhibits (blocks) binding of the other to the antigen. That is, a 1-, 5-, 10-, 20- or 100-fold excess of one antibody inhibits binding of the other by at least 50% but preferably 75%, 90% or even 99% as measured in a competitive binding assay (see, e.g., Junghans et al., Cancer Res, 1990:50:1495-1502). Alternatively, two antibodies have the same epitope if essentially all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

Additional routine experimentation (e.g., peptide mutation and binding analyses) can then be carried out to confirm whether the observed lack of binding of the test antibody is in fact due to binding to the same epitope as the reference antibody or if steric blocking (or another phenomenon) is responsible for the lack of observed binding. Experiments of this sort can be performed using ELISA, RIA, surface plasmon resonance, flow cytometry or any other quantitative or qualitative antibody-binding assay available in the art.

Immunoconjugates

The invention encompasses a human anti-ANGPTL3 monoclonal antibody conjugated to a therapeutic moiety ("immunoconjugate"), such as a cytotoxin, a chemotherapeutic drug, an immunosuppressant or a radioisotope. Cytotoxin agents include any agent that is detrimental to cells. Examples of suitable cytotoxin agents and chemotherapeutic agents for forming immunoconjugates are known in the art, see for example, WO 05/103081.

Bispecifics

The antibodies of the present invention may be monospecific, bispecific, or multispecific. Multispecific mAbs may be specific for different epitopes of one target polypeptide or may contain antigen-binding domains specific for more than one target polypeptide. See, e.g., Tutt et al. (1991) J. Immunol. 147:60-69. The human anti-hANGPTL3 mAbs can be linked to or co-expressed with another functional molecule, e.g., another peptide or protein. For example, an antibody or fragment thereof can be functionally linked (e.g., by chemical coupling, genetic fusion, noncovalent association or otherwise) to one or more other molecular entities, such as another antibody or antibody fragment, to produce a bispecific or a multispecific antibody with a second binding specificity.

An exemplary bi-specific antibody format that can be used in the context of the present invention involves the use of a first immunoglobulin (Ig) $C_H3$ domain and a second Ig $C_H3$ domain, wherein the first and second Ig $C_H3$ domains differ from one another by at least one amino acid, and wherein at least one amino acid difference reduces binding of the bispecific antibody to Protein A as compared to a bi-specific antibody lacking the amino acid difference. In one embodiment, the first Ig $C_H3$ domain binds Protein A and the second Ig $C_H3$ domain contains a mutation that reduces or abolishes Protein A binding such as an H95R modification (by IMGT exon numbering; H435R by EU numbering). The second $C_H3$ may further comprise a Y96F modification (by IMGT; Y436F by EU). Further modifications that may be found within the second $C_H3$ include: D16E, L18M, N44S, K52N, V57M, and V82I (by IMGT; D356E, L358M, N384S, K392N, V397M, and V422I by EU) in the case of IgG1 antibodies; N44S, K52N, and V82I (IMGT; N384S, K392N, and V422I by EU) in the case of IgG2 antibodies; and Q15R, N44S, K52N, V57M, R69K, E79Q, and V82I (by IMGT; Q355R, N384S, K392N, V397M, R409K, E419Q, and V422I by EU) in the case of IgG4 antibodies. Variations on the bi-specific antibody format described above are contemplated within the scope of the present invention.

Bioequivalents

The anti-hANGPTL3 antibodies and antibody fragments of the present invention encompass proteins having amino acid sequences that vary from those of the described mAbs, but that retain the ability to bind human ANGPTL3. Such variant mAbs and antibody fragments comprise one or more additions, deletions, or substitutions of amino acids when compared to parent sequence, but exhibit biological activity that is essentially equivalent to that of the described mAbs. Likewise, the anti-hANGPTL3 antibody-encoding DNA sequences of the present invention encompass sequences that comprise one or more additions, deletions, or substitutions of nucleotides when compared to the disclosed sequence, but that encode an anti-hANGPTL3 antibody or antibody fragment that is essentially bioequivalent to an anti-hANGPTL3 antibody or antibody fragment of the invention. Examples of such variant amino acid and DNA sequences are discussed above.

Two antigen-binding proteins, or antibodies, are considered bioequivalent if, for example, they are pharmaceutical equivalents or pharmaceutical alternatives whose rate and extent of absorption do not show a significant difference when administered at the same molar dose under similar experimental conditions, either single does or multiple dose. Some antibodies will be considered equivalents or pharmaceutical alternatives if they are equivalent in the extent of their absorption but not in their rate of absorption and yet may be considered bioequivalent because such differences in the rate of absorption are intentional and are reflected in the labeling, are not essential to the attainment of effective body drug concentrations on, e.g., chronic use, and are considered medically insignificant for the particular drug product studied. In one embodiment, two antigen-binding proteins are bioequivalent if there are no clinically meaningful differences in their safety, purity, and potency.

In one embodiment, two antigen-binding proteins are bioequivalent if a patient can be switched one or more times between the reference product and the biological product without an expected increase in the risk of adverse effects, including a clinically significant change in immunogenicity, or diminished effectiveness, as compared to continued therapy without such switching.

In one embodiment, two antigen-binding proteins are bioequivalent if they both act by a common mechanism or mechanisms of action for the condition or conditions of use, to the extent that such mechanisms are known.

Bioequivalence may be demonstrated by in vivo and in vitro methods. Bioequivalence measures include, e.g., (a) an in vivo test in humans or other mammals, in which the concentration of the antibody or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the antibody (or its target) is measured as a function of time; and (d) in a well-controlled clinical trial that establishes safety, efficacy, or bioavailability or bioequivalence of an antibody.

Bioequivalent variants of anti-hANGPTL3 antibodies of the invention may be constructed by, for example, making various substitutions of residues or sequences or deleting terminal or internal residues or sequences not needed for biological activity. For example, cysteine residues not essential for biological activity can be deleted or replaced with other amino acids to prevent formation of unnecessary or incorrect intramolecular disulfide bridges upon renaturation.

Therapeutic Administration and Formulations

The invention provides therapeutic compositions comprising the anti-hANGPTL3 antibodies or antigen-binding fragments thereof of the present invention and the therapeutic methods using the same. The administration of therapeutic compositions in accordance with the invention will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) *J Pharm Sci Technol* 52:238-311.

The dose may vary depending upon the age and the size of a subject to be administered, target disease, the purpose of the treatment, conditions, route of administration, and the like. When the antibody of the present invention is used for treating various conditions and diseases directly or indirectly associated with ANGPTL3, including hypercholesterolemia, disorders associated with LDL and apolipoprotein B, and lipid metabolism disorders, and the like, in an adult patient, it is advantageous to intravenously or subcutaneously administer the antibody of the present invention at a single dose of about 0.01 to about 20 mg/kg body weight, more preferably about 0.02 to about 7, about 0.03 to about 5, or about 0.05 to about 3 mg/kg body weight. Depending on the severity of the condition, the frequency and the duration of the treatment can be adjusted. In certain embodiments, the antibody or antigen-binding fragment thereof of the invention can be administered as an initial dose of at least about 0.1 mg to about 800 mg, about 1 to about 500 mg, about 5 to about 300 mg, or about 10 to about 200 mg, to about 100 mg, or about 50 mg. In certain embodiments, the initial dose may be followed by administration of a second or a plurality of subsequent doses of the antibody or antigen-binding fragment thereof in an amount that can be approximately the same or less than that of the initial dose, wherein the subsequent doses are separated by at least 1 day to 3 days; at least one week, at least 2 weeks; at least 3 weeks; at least 4 weeks; at least 5 weeks; at least 6 weeks; at least 7 weeks; at least 8 weeks; at least 9 weeks; at least 10 weeks; at least 12 weeks; or at least 14 weeks.

Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see, e.g., Wu et al. (1987) J. Biol. Chem. 262:4429-4432). Methods of introduction include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

The pharmaceutical composition can be also delivered in a vesicle, in particular a liposome (see Langer (1990) Science 249:1527-1533; Treat et al. (1989) in Liposomes in the Therapy of Infectious Disease and Cancer, Lopez Berestein and Fidler (eds.), Liss, New York, pp. 353-365; Lopez-Berestein, ibid., pp. 317-327; see generally ibid.).

In certain situations, the pharmaceutical composition can be delivered in a controlled release system. In one embodiment, a pump may be used (see Langer, supra; Sefton (1987) CRC Crit. Ref. Biomed. Eng. 14:201). In another embodiment, polymeric materials can be used; see, Medical Applications of Controlled Release, Langer and Wise (eds.), *CRC Pres.*, Boca Raton, Fla. (1974). In yet another embodiment, a controlled release system can be placed in proximity of the composition's target, thus requiring only a fraction of the systemic dose (see, e.g., Goodson, in Medical Applications of Controlled Release, supra, vol. 2, pp. 115-138, 1984).

The injectable preparations may include dosage forms for intravenous, subcutaneous, intracutaneous and intramuscular injections, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule. A pharmaceutical composition of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the present invention. Examples include, but certainly are not limited to AUTOPEN™ (Owen Mumford, Inc., Woodstock, UK), DISETRONIC™ pen (Disetronic Medical Systems, Burghdorf, Switzerland), HUMALOG MIX 75/25™ pen, HUMALOG™ pen, HUMALIN 70/30™ pen (Eli Lilly and Co., Indianapolis, Ind.), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPENTm, OPTIPEN PRO™, OPTIPEN STARLET™, and OPTICLIK™ (Sanofi-Aventis, Frankfurt, Germany), to name only a few. Examples of disposable pen delivery devices having applications in subcutaneous delivery of a pharmaceutical composition of the present invention include, but certainly are not limited to the SOLOSTAR™ pen (Sanofi-Aventis), the FLEXPEN™ (Novo Nordisk), and the KWIKPEN™ (Eli Lilly).

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the aforesaid antibody contained is generally about 0.1 to about 800 mg per dosage form in a unit dose; especially in the form of injection, the aforesaid antibody is contained in about 1 to about 500 mg, in about 5 to 300 mg, in about 8 to 200 mg, and in about 10 to about 100 mg for the other dosage forms.

Combination Therapies

The invention further provides therapeutic methods for treating diseases or disorders, which is directly or indirectly associated with hANGPTL3, by administering a hANGPTL3 antibody or fragment thereof of the invention in combination with one or more additional therapeutic agents. The additional therapeutic agent may be one or more of any agent that is advantageously combined with one or more antibodies or fragments thereof of the invention, including HMG-CoA reductase inhibitors, such as cerovastatin, atorvastatin, simvastatin, pitavastin, rosuvastatin, fluvastatin, lovastatin, pravastatin, and the like; niacin; various fibrates, such as fenofibrate, bezafibrate, ciprofibrate, clofibrate, gemfibrozil, and the like; LXR transcription factor activators, and the like. Furthermore, the hANGPTL3 antibody or fragment thereof of the invention can be co-administered with other ANGPTL3 inhibitors as well as inhibitors of other molecules, such as ANGPTL4, ANGPTL5, ANGPTL6 and proprotein convertase subtilisin/kexin type 9 (PCSK9), which are involved in lipid metabolism, in particular, cholesterol and/or triglyceride homeostasis. Inhibitors of these molecules include small molecules and antibodies that specifically bind to these molecules and block their activity (see, for example, anti-PCSK9 antibodies disclosed in U.S. 2010/0166768 A1).

Furthermore, the additional therapeutic agent may be one or more anti-cancer agents, such as chemotherapeutic agents, anti-angiogenic agents, growth inhibitory agents, cytotoxic agents, apoptotic agents, and other agents well known in the art to treat cancer or other proliferative diseases or disorders. Examples of anti-cancer agents include, but are not limited to, an anti-mitotic agent, such as docetaxel, paclitaxel, and the like; a platinum-based chemotherapeutic compound, such as cisplatin, carboplatin, iproplatin, oxaliplatin, and the like; or other conventional cytotoxic agent, such as 5-fluorouracil, capecitabine, irinotecan, leucovorin, gemcitabine, and the like, and anti-angiogenic agents, including vascular endothelial growth factor (VEGF) antagonists, such as anti-VEGF antibodies, e.g., bevacizumab (AVASTIN®, Genentech) and a receptor-based blocker of VEGF, e.g., "VEGF trap" described in U.S. Pat. No. 7,070,959, delta-like ligand 4 (Dll4) antagonists, such as anti-Dll4 antibodies as described in U.S. Patent Application Publication No. 2008/0181899, and a fusion protein containing the extracellular domain of Dll4, e.g., Dll4-Fc as described in U.S. Patent Application Publication No. 2008/0107648; inhibitors of receptor tyrosine kinases and/or angiogenesis, including sorafenib (NEXAVAR® by Bayer Pharmaceuticals Corp.), sunitinib (SUTENT® by Pfizer), pazopanib (VOTRIENT™ by GlaxoSmithKline), toceranib (PALLADIA™ by Pfizer), vandetanib (ZACTIMA™ by AstraZeneca), cediranib (RECENTIN® by AstraZeneca), regorafenib (BAY 73-4506 by Bayer), axitinib (AG013736 by Pfizer), lestaurtinib (CEP-701 by Cephalon), erlotinib (TARCEVA® by Genentech), gefitinib (IRESSA™ by AstraZeneca), BIBW 2992 (TOVOK™ by Boehringer Ingelheim), lapatinib (TYKERB® by GlaxoSmithKline), neratinib (HKI-272 by Wyeth/Pfizer), and the like, and pharmaceutically acceptable salts, acids or derivatives of any of the above. In addition, other therapeutic agents, such as analgesics, anti-inflammatory agents, including non-steroidal anti-inflammatory drugs (NSAIDS), such as Cox-2 inhibitors, and the like, may be also co-administered with the hANGPTL3 antibody or fragment thereof of the invention so as to ameliorate and/or reduce the symptoms accompanying the underlying cancer/tumor.

The hANGPTL3 antibody or fragment thereof of the invention and the additional therapeutic agent(s) can be co-administered together or separately. Where separate dosage formulations are used, the antibody or fragment thereof of the invention and the additional agents can be administered concurrently, or separately at staggered times, i.e., sequentially, in appropriate orders.

Diagnostic Uses of the Antibodies

The anti-ANGPTL3 antibodies of the present invention can be also used to detect and/or measure ANGPTL3 in a sample, e.g., for diagnostic purposes. For example, an anti-ANGPTL3 Ab or fragment thereof, can be used to diagnose a condition or disease characterized by aberrant expression (e.g., over-expression, under-expression, lack of expression, etc.) of ANGPTL3. Exemplary diagnostic assays for ANGPTL3 may comprise, e.g., contacting a sample obtained from a patient, with an anti-ANGPTL3 Ab of the invention, wherein the anti-ANGPTL3 antibody is labeled with a detectable label or reporter molecule or used to selectively capture and isolate ANGPTL3 protein from patient samples. Alternatively, an unlabeled anti-ANGPTL3 Ab can be used in diagnostic applications in combination with a secondary antibody which is itself detectably labeled. The detectable label or reporter molecule can be a radioisotope, such as $^3$H, $^{14}$C, $^{32}$P, $^{35}$S, $^{131}$I or $^{125}$I; a fluorescent or chemiluminescent moiety, such as fluorescein isothiocyanate, or rhodamine; or an enzyme such as alkaline phosphatase, β-galactosidase, horseradish peroxidase, or luciferase. Assays that can be used to detect or measure ANGPTL3 in a sample include enzyme-linked immunosorbent assay (ELISA), radioimmunoassay (RIA), fluorescence-activated cell sorting (FACS), and the like.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used but some experimental errors and deviations should be accounted for. Unless indicated otherwise, molecular weight is average molecular weight, temperature is in degrees Centigrade, and pressure is at or near atmospheric.

Example 1. Generation of Human Antibodies to Human ANGPTL3

VELOCIMMUNE™ mice were immunized with human ANGPTL3, and the antibody immune response monitored by antigen-specific immunoassay using serum obtained from these mice. Anti-hANGPTL3 expressing B cells were harvested from the spleens of immunized mice shown to have elevated anti-hANGPTL3 antibody titers and were fused with mouse myeloma cells to form hybridomas. The hybridomas were screened and selected to identify cell lines expressing hANGPTL3-specific antibodies using assays as described below. The assays identified several cell lines that produced chimeric anti-hANGPTL3 antibodies, e.g., H1M896N.

Human ANGPTL3-specific antibodies were also isolated directly from antigen-immunized B cells without fusion to myeloma cells, as described in U.S. 2007/0280945 A1.

Heavy and light chain variable regions were cloned to generate fully human anti-hANGPTL3 antibodies of IgG4 isotype designated as H4H1248P, H4H1250P, H4H1263S, H4H1268S, H4H1276S, H4H1279P, H4H1282P, H4H1292P, H4H1295P and H4H1296P. Stable recombinant antibody-expressing CHO cell lines were established.

Example 2. Variable Gene Utilization Analysis

To analyze the structure of antibodies produced, the nucleic acids encoding antibody variable regions were cloned and sequenced. From the nucleic acid sequence and predicted amino acid sequence of the antibodies, gene usage was identified for each Heavy Chain Variable Region (HCVR) and Light Chain Variable Region (LCVR). Table 1 shows the gene usage for selected antibodies in accordance with the invention.

TABLE 1

| Antibody | HCVR | | | LCVR | |
|---|---|---|---|---|---|
| | $V_H$ | $D_H$ | $J_H$ | $V_K$ | $J_K$ |
| H4H1248P | 3-30 | 1-26 | 6 | 1-12 | 3 |
| H4H1250P | 3-30 | 1-7 | 6 | 1-5 | 1 |
| H4H1263S | 3-30 | 3-10 | 6 | 1-12 | 3 |
| H4H1268S | 6-1 | 6-6 | 4 | 1-5 | 1 |
| H4H1276S | 3-43 | 3-3 | 3 | 1-5 | 2 |
| H4H1279P | 3-11 | 1-1 | 4 | 1-39 | 4 |
| H4H1282P | 1-18 | 3-10 | 4 | 1-9 | 4 |
| H4H1292P | 3-11 | 1-1 | 4 | 1-39 | 4 |
| H4H1295P | 1-18 | 6-25 | 4 | 2-30 | 2 |
| H4H1296P | 3-11 | 1-1 | 4 | 1-39 | 4 |
| H1M896N | 3-23 | 3-10 | 4 | 1-5 | 1 |

Table 2 shows the heavy and light chain variable region amino acid sequence pairs of selected anti-hANGPTL3 antibodies and their corresponding antibody identifiers. The N, P and S designations refer to antibodies having heavy and light chains with identical CDR sequences but with sequence variations in regions that fall outside of the CDR sequences (i.e., in the framework regions). Thus, N, P and S variants of a particular antibody have identical CDR sequences within their heavy and light chain variable regions but contain modifications within the framework regions.

TABLE 2

| Name | HCVR/LCVR SEQ ID NOs |
|---|---|
| H4H1248P | 2/10 |
| H4H1250P | 18/26 |
| H4H1263S | 34/42 |
| H4H1268S | 50/58 |
| H4H1276S | 66/74 |
| H1M896N | 180/188 |
| H4H1279P | 82/90 |
| H4H1282P | 98/106 |
| H4H1292P | 114/122 |
| H4H1295P | 130/138 |
| H4H1296P | 146/154 |
| — | — |

Example 3. Kinetic Parameters of Anti-hANGPTL3 Antibodies Binding to ANGPTL3

All kinetic binding experiments were performed at 25° C. or 37° C. on a BIACORE™ T200 label-free molecular interaction instrument (GE Healthcare) using a CM5 sensor chip. Briefly, an antigen capture surface was generated by covalently coupling either an anti-mouse IgG-specific antibody (anti-mFc; GE Healthcare; catalog #BR-1008-38) or an anti-pentahistidine-specific antibody (Qiagen; catalog #34660) to the surface of a CM5 sensor chip using a standard amine coupling method. Using HBS-EP (10 mM HEPES, 150 mM NaCl, 3 mM EDTA, 0.05% Surfactant P20, pH 7.4) or PBSP (10 mM sodium phosphate, 2.7 mM KCl, 137 mM NaCl, 0.025% Surfactant P20, pH 7.2 or 5.75) as the running buffer, human and species variants of ANGPTL3 with oligohistidine tags were captured on the anti-penta-histidine coupled surface until a binding response of 4.4-46.5 RUs was achieved. The captured recombinant proteins were: full-length mature human ANGPTL3 (i.e., amino acid residues 17-460 of SEQ ID NO:161) with a C-terminal decahistidine tag [hANGPTL3(17-460)-His; R&D Systems, MN; catalog #3829-AN], N-terminal coiled-coil domain of hANGPTL3 (i.e., amino acid residues 17-170 of SEQ ID NO:161) containing a C-terminal hexahistidine tag [hANGPTL3(17-170)-His], N-terminal coiled-coil domain of ANGPTL3 from *Macaca fascicularis* [i.e., amino acid residues 17-170 of SEQ ID NO:177 (a partial sequence of *Macaca fascicularis* ANGPTL3)] containing a myc-myc-hexahistidine tag [MfANGPTL3(17-170)-mmH; SEQ ID NO:167], full-length mature ANGPTL3 from *Mus musculus* (i.e., amino acid residues 17-455 of SEQ ID NO:163) with a C-terminal decahistidine tag [mANGPTL3(17-455)-His; R&D Systems, MN; catalog #136-AN], N-terminal coiled-coil domain of ANGPTL3 from *Mus musculus* (i.e., amino acid residues 17-240 of SEQ ID NO:163) containing a hexahistidine tag [mANGPTL3(17-240)-His; SEQ ID NO:166], and N-terminal coiled-coil domain of ANGPTL3 from *Rattus norvegicus* (i.e., amino acid residues 17-240 of SEQ ID NO:175) containing a myc-myc-hexahistidine tag [rANGPTL3(17-240)-mmH; SEQ ID NO:176]. In addition, the N-terminal coiled-coil domain of hANGPTL3 (i.e., amino acid residues 17-169 of SEQ ID NO:161) containing a C-terminal mouse Fc fusion [hANGPTL3(17-169)-mFc; SEQ ID NO:165] was captured on the anti-mFc coupled surface until a binding response of 24.8±1.5 RUs was achieved. To measure association and dissociation rates for formation of the antibody/antigen complex, a single (Tables 3 and 7) or multiple (Tables 4-6) concentrations of antibody were injected across the captured protein surface at a flow rate of 50 μl/minute for 3 minutes and dissociation of the complex was monitored for 20 minutes. Binding data were processed and fitted to a 1:1 binding model with mass transport using Scrubber version 2.0a (BioLogic Software). The kinetic half-lives ($t_{1/2}$) were calculated from the dissociation rate constant, kd.

Table 3 shows the binding of various anti-ANGPTL3 antibodies to hANGPTL3 at 25° C., pH 7.4, in HBS-EP buffer.

TABLE 3

| Ab Clones | Protein | ka ($M^{-1}s^{-1}$) | kd ($s^{-1}$) | $K_D$ (nM) | $t_{1/2}$ (min) |
|---|---|---|---|---|---|
| H4H1248P | hANGPTL3(17-169)-mFc | 4.57E+05 | 2.72E−03 | 5.95 | 4 |
|  | hANGPTL3(17-460)-His | 4.40E+05 | 2.47E−03 | 5.62 | 5 |
| H4H1250P | hANGPTL3(17-169)-mFc | 1.25E+06 | 6.51E−04 | 0.519 | 18 |
|  | hANGPTL3(17-460)-His | 9.04E+05 | 6.57E−04 | 0.726 | 18 |

TABLE 3-continued

| Ab Clones | Protein | ka ($M^{-1}s^{-1}$) | kd ($s^{-1}$) | $K_D$ (nM) | $t_{1/2}$ (min) |
|---|---|---|---|---|---|
| H4H1263S | hANGPTL3(17-169)-mFc | 6.77E+05 | 4.22E−03 | 6.23 | 3 |
|  | hANGPTL3(17-460)-His | 5.08E+05 | 1.26E−03 | 2.47 | 9 |
| H4H1268S | hANGPTL3(17-169)-mFc | 1.16E+06 | 8.35E−04 | 0.721 | 14 |
|  | hANGPTL3(17-460)-His | 1.29E+06 | 1.89E−03 | 1.47 | 6 |
| H4H1276S | hANGPTL3(17-169)-mFc | 5.82E+05 | 3.83E−04 | 0.659 | 30 |
|  | hANGPTL3(17-460)-His | 3.44E+05 | 4.64E−04 | 1.35 | 25 |
| H4H1279P | hANGPTL3(17-169)-mFc | 6.58E+05 | 5.53E−06 | 0.00841 | 2088 |
|  | hANGPTL3(17-460)-His | 2.88E+05 | 1.14E−04 | 0.394 | 102 |
| H4H1282P | hANGPTL3(17-169)-mFc | 1.28E+06 | 5.92E−05 | 0.0463 | 195 |
|  | hANGPTL3(17-460)-His | 9.57E+05 | 9.26E−05 | 0.0968 | 125 |
| H4H1292P | hANGPTL3(17-169)-mFc | 6.86E+05 | 1.77E−04 | 0.257 | 65 |
|  | hANGPTL3(17-460)-His | 3.41E+05 | 2.48E−04 | 0.727 | 47 |
| H4H1295P | hANGPTL3(17-169)-mFc | 3.52E+05 | 7.95E−05 | 0.226 | 145 |
|  | hANGPTL3(17-460)-His | 3.73E+05 | 7.35E−05 | 0.197 | 157 |
| H4H1296P | hANGPTL3(17-169)-mFc | 6.41E+05 | 3.92E−05 | 0.0611 | 295 |
|  | hANGPTL3(17-460)-His | 3.01E+05 | 4.12E−05 | 0.137 | 280 |

As shown in Table 3, the anti-hANGPLT3 antibodies bound to the full-length protein with a C-terminal decahistidine tag [hANGPTL3(17-460)-His] with calculated equilibrium dissociation constants ($K_D$=kd/ka) ranging from 96.8 pM to 5.62 nM and to the N-terminal coiled-coil domain with a C-terminal Fc fusion [hANGPTL3(17-169)-mFc] with $K_D$s ranging from 8.41 pM to 6.23 nM.

Tables 4 and 5 show the cross-species binding of H4H1276S to ANGPTL3 at 25° C. and 37° C., respectively, at pH 7.4, in HBS-EP buffer. Table 6 shows the binding of H4H1276S to human and cynomolgus ANGPTL3, at 25° C. or 37° C., at pH 5.75 or pH 7.2, in PBSP buffer.

TABLE 4

| | | 25° C. | | | |
|---|---|---|---|---|---|
| Ab Clone | Protein | ka ($M^{-1}s^{-1}$) | kd ($s^{-1}$) | $K_D$ (nM) | $t_{1/2}$ (min) |
| H4H1276S | hANGPTL3(17-170)-His | 9.73E+05 | 9.12E−04 | 0.938 | 12.7 |
|  | hANGPTL3(17-460)-His | 5.88E+05 | 2.89E−04 | 0.491 | 40.0 |
|  | MfANGPTL3(17-170)-mmH | 1.35E+06 | 5.35E−04 | 0.396 | 21.6 |
|  | mANGPTL3(17-240)-His | 6.70E+05 | 3.07E−04 | 0.458 | 37.6 |
|  | mANGPTL3(17-455)-His | 1.29E+06 | 3.46E−04 | 0.268 | 33.4 |
|  | rANGPTL3(17-240)-mmH | 1.35E+06 | 7.18E−04 | 0.530 | 16.1 |

TABLE 5

| Ab Clone | Protein | 37° C. | | | |
|---|---|---|---|---|---|
| | | ka (M$^{-1}$s$^{-1}$) | kd (s$^{-1}$) | $K_D$ (nM) | $t_{1/2}$ (min) |
| H4H1276S | hANGPTL3(17-170)-His | 1.59E+06 | 2.41E−03 | 1.52 | 4.8 |
| | hANGPTL3(17-460)-His | 6.32E+05 | 8.12E−04 | 1.29 | 14.2 |
| | MfANGPTL3(17-170)-mmH | 1.87E+06 | 1.17E−03 | 0.625 | 9.9 |
| | mANGPTL3(17-240)-His | 8.19E+05 | 9.64E−04 | 1.18 | 12.0 |
| | mANGPTL3(17-455)-His | 1.94E+06 | 7.91E−04 | 0.408 | 14.6 |
| | rANGPTL3(17-240)-mmH | 2.05E+06 | 1.93E−03 | 0.940 | 6.0 |

TABLE 6

| Ab Clone | Protein | ka (M$^{-1}$s$^{-1}$) | kd (s$^{-1}$) | $K_D$ (nM) | $t_{1/2}$ (min) |
|---|---|---|---|---|---|
| H4H1276S pH 7.2 25° C. | hANGPTL3(17-170)-His | 1.00E+06 | 1.10E−03 | 1.09 | 10.5 |
| | hANGPTL3(17-460)-His | 5.99E+05 | 4.02E−04 | 0.670 | 28.8 |
| | MfANGPTL3(17-170)-mmH | 1.45E+06 | 5.38E−04 | 0.370 | 21.5 |
| H4H1276S pH 5.75 25° C. | hANGPTL3(17-170)-His | 2.80E+05 | 6.72E−03 | 24.0 | 1.7 |
| | hANGPTL3(17-460)-His | 7.32E+04 | 4.94E−03 | 67.5 | 2.3 |
| | MfANGPTL3(17-170)-mmH | 2.06E+05 | 4.32E−03 | 21.0 | 2.7 |
| H4H1276S pH 7.2 37° C. | hANGPTL3(17-170)-His | 1.57E+06 | 2.73E−03 | 1.74 | 4.2 |
| | hANGPTL3(17-460)-His | 6.67E+05 | 1.18E−03 | 1.76 | 9.8 |
| | MfANGPTL3(17-170)-mmH | 1.94E+06 | 1.36E−03 | 0.700 | 8.5 |
| H4H1276S pH 5.75 37° C. | hANGPTL3(17-170)-His | 1.22E+06 | 3.24E−02 | 26.7 | 0.4 |
| | hANGPTL3(17-460)-His | 4.71E+04 | 1.07E−02 | 227 | 1.1 |
| | MfANGPTL3(17-170)-mmH | 2.78E+05 | 5.21E−03 | 18.8 | 2.2 |

As shown in Tables 4-6, antibody H4H1276S exhibited binding to ANGPTL3 from monkey, mouse, and rat with binding affinities and kinetic constants similar to those for binding to human ANGPTL3.

Table 7 shows the binding of selected anti-ANGPTL3 antibodies to hANGPTL3 and mANGPTL3 at 37° C., pH 7.4, in HBS-EP buffer. NB: Not bound.

As shown in Table 7, the anti-hANGPLT3 antibodies bound to the full-length protein with a C-terminal decahistidine tag [hANGPTL3(17-460)-His] at pH 7.4 and 37° C. with calculated equilibrium dissociation constants ($K_D$=kd/ka) ranging from 158 pM to 1.02 nM and to mouse ANGPTL3 [mANGPTL3(17-455)-His] with $K_D$s ranging from 167 pM to 682 pM, except for H4H1248P and H4H1263S, which did not show detectable binding to mANGPTL3. Also shown are the kinetic half-lives ($t_{1/2}$).

Example 4. Biacore Cross-Competition Study for Anti-ANGPTL3 Antibodies

Cross competition experiments were performed at 25° C. on a Biacore essentially as described in Example 3 above. Briefly, using HBS-EP as the running buffer, full-length hANGPTL3 (i.e., amino acid residues 17-460 of SEQ ID NO:161) with a C-terminal decahistidine tag [hANGPTL3 (17-460)-His; R&D Systems, MN; catalog #3829-AN] was captured on the anti-penta-histidine coupled surface until a binding response of 64 RUs was achieved. To determine whether two antibodies could bind simultaneously to the captured ANGPTL3, antibody pairs were injected sequentially, each at 167 nM at a flow rate of 4 μl/minute for 15 minutes, over the surface, and the maximum binding response signal (RU) was measured for each binding event. The results are shown in Table 8 with binding response for the first antibody (mAb1), followed by binding response of the second antibody (mAb2) on the ANGPTL3 surface pre-loaded with the first antibody. Numbers in bold indicate that the antibody pairs are able to bind to hANGPTL3 simultaneously. Numbers in italics indicate that that the antibody pairs are able to bind to hANGPTL3 simultaneously when added sequentially in one direction but not the other. Brackets indicate self-self competition.

TABLE 7

| Ab Clones | Protein | ka (M$^{-1}$s$^{-1}$) | kd (s$^{-1}$) | $K_D$ (nM) | $t_{1/2}$ (min) |
|---|---|---|---|---|---|
| H1M896N | hANGPTL3(17-460)-His | 3.36E+06 | 5.30E−04 | 1.58E−10 | 22 |
| | mANGPTL3(17-455)-His | 3.62E+06 | 2.47E−03 | 6.82E−10 | 5 |
| H4H1248P | hANGPTL3(17-460)-His | 1.96E+06 | 1.93E−03 | 9.86E−10 | 6 |
| | mANGPTL3(17-455)-His | NB | NB | NB | NB |
| H4H1250P | hANGPTL3(17-460)-His | 3.50E+06 | 1.13E−03 | 3.24E−10 | 10 |
| | mANGPTL3(17-455)-His | 3.18E+06 | 1.55E−03 | 4.86E−10 | 7 |
| H4H1263S | hANGPTL3(17-460)-His | 4.74E+06 | 1.81E−03 | 3.81E−10 | 6 |
| | mANGPTL3(17-455)-His | NB | NB | NB | NB |
| H4H1279P | hANGPTL3(17-460)-His | 4.74E+06 | 1.81E−03 | 3.81E−10 | 6 |
| | mANGPTL3(17-455)-His | 2.15E+06 | 3.59E−04 | 1.67E−10 | 32 |
| H4H1292P | hANGPTL3(17-460)-His | 1.89E+06 | 1.94E−03 | 1.02E−09 | 6 |
| | mANGPTL3(17-455)-His | 3.92E+06 | 1.49E−03 | 3.80E−10 | 8 |

TABLE 8

| Ab Clones | hANGPTL3(17-460)-His captured (RU) | 25 μg/ml mAb1 binding response (RU) | 25 μg/ml mAb2 binding response (RU) | | | |
|---|---|---|---|---|---|---|
| | | | H1M896N | H4H1250P | H4H1279P | H4H1292P |
| H1M896N | 64 ± 4 | 171 ± 1.8 | [−4] | −4 | 47 | 50 |
| H4H1250P | | 210 ± 8.3 | −4 | [13] | 9 | 8 |
| H4H1279P | | 45 ± 1.8 | 186 | 213 | [−3] | −1 |
| H4H1292P | | 48 ± 0.7 | 182 | 220 | −3 | [−2] |
| Negative Control | | 81 ± 1.8 | 149 | 187 | 47 | 48 |

As shown in Table 8, antibody pairs H1M896N/H4H1279P and H1M896N/H4H1292P were able to bind simultaneously to immobilized ANGPTL3, regardless of the order of addition of the antibodies. H4H1250P bound to ANGPTL3 pre-bound with H4H1279P; however, when the order of antibody addition was reversed, H4H1279P exhibited a binding signal approximately 24% of the expected maximal response after ANGPTL3 was pre-bound with H4H1250P. Similarly, H4H1250P bound to ANGPTL3 pre-bound with H4H1292P; however, when the order of antibody addition was reversed, H4H1292P exhibited a binding signal approximately 20% of the expected maximal response after ANGPTL3 was pre-bound with H4H1250P.

Example 5. Anti-hANGPTL3 Antibody Binding to ANGPTL3 N-terminal Coiled-Coil Peptides To assess the binding of the anti-ANGPTL3 antibody H4H1276S to peptides derived from the N-terminal coiled-coil region of ANGPTL3, a label-free biosensor binding assay was performed using OCTET® RED system (FortéBio, Inc.). For immobilization onto the sensor, peptides were labeled with either an N-terminal biotin tag [separated by a flexible linker, amino acids "AGSSPGG" (SEQ ID NO:171), for Peptide 1 and Peptide 2; and amino acids "GGGGS" (SEQ ID NO:172) for Peptide 3], or a C-terminal biotin tag [separated by a flexible linker, amino acids "GPSSGAPPPK" (SEQ ID NO:173), for Peptide 1 and Peptide 2; and amino acids "GGGGSK" (SEQ ID NO:174) for Peptide 3]. The peptide sequences tested were: A negative control peptide, N-terminal biotin tagged Peptide1 (SEQ ID NO:168; residues Arg34 to Leu66 of human ANTGPTL4 of SEQ ID NO:164); and peptides derived from the N-terminal coiled-coil region of ANGPTL3, i.e., N-terminal biotin tagged Peptide 2 (SEQ ID NO:169; residues Arg36 to Leu68 of hANGPTL3 of SEQ ID NO:161); C-terminal biotin tagged Peptide 2; N-terminal biotin tagged Peptide 3 (SEQ ID NO:170; corresponds to residues Glu32 to Leu57 of hANGPTL3 of SEQ ID NO:161); and C-terminal biotin tagged Peptide 3. Peptide sequences are also shown in FIG. 1. Streptavidin-coated biosensor tips were coated with the biotinylated peptides resulting in 1.22-2.26 nm of binding response units depending on the peptide. The peptide-coated biosensor tips were then dipped into wells containing 1 μM of either anti-ANGPTL3 antibody H4H1276S or an isotype-matched negative control antibody, and binding was monitored for 2.5 minutes. The binding response of H4H1276S and the isotype control antibody to each of the peptides is summarized in FIG. 2. It was observed that H4H1276S binds to the ANGPTL3 linear sequence defined by Peptide 2 but not the overlapping but distinct sequence defined by Peptide 3 (see also FIG. 1). The isotype control antibody also served as a positive control for loading of Peptide 1 (i.e., hANGPTL4 peptide) onto the biosensor, because this isotype control antibody specifically recognizes hANGPTL4. As shown in FIG. 2, the binding of the control antibody to Peptide 1 confirmed that Peptide 1 was present on the sensor surface and so were the other peptides.

Example 6. Inhibition of hANGPTL3 by Anti-hANGPTL3 Antibodies in LPL Bioassays Lipoprotein Lipase (LPL) plays a critical role in lipid metabolism in humans. LPL catalyzes hydrolysis of triglycerides and releases fatty acids to be metabolized. ANGPTL3 inhibits LPL activity leading to increased level of lipids (Oike et al., 2005, Trends in Molecular Medicine 11(10): 473-479). The N-terminal coiled-coil region of ANGPTL3 inhibits LPL when expressed without the C-terminal fibrinogen region and therefore appears to confer its inhibitory function. A cell-free bioassay was developed to determine the ability of anti-ANGPTL3 antibodies to inhibit ANGPTL3-induced decrease in LPL activity.

Inhibition of hANGPTL3 activity by anti-ANGPTL3 antibodies was determined using the CONFLUOLIP™ Continuous Fluorometric Lipase Test (Progen, Germany) using three hANGPTL3 proteins: full-length mature hANGPTL3 (i.e., amino acid residues 17-460 of SEQ ID NO:161) with a C-terminal decahistidine tag [hANGPTL3(17-460)-His; R&D Systems, MN; catalog #3829-AN], the N-terminal coiled-coil region (i.e., amino acid residues 17-169 of SEQ ID NO:161) with a C-terminal mouse Fc fusion [hANGPTL3(17-169)-mFc; SEQ ID NO:165], and the N-terminal coiled-coil domain of hANGPTL3 (i.e., amino acid residues 17-170 of SEQ ID NO:161) containing a C-terminal hexahistidine tag [hANGPTL3(17-170)-His].

Briefly, bovine LPL (final concentration of 2 nM), human ApoCII (a cofactor of LPL, final concentration of 0.23 μM), and BSA (final concentration of 2 mg/mL) in PBS were premixed. The hANGPTL3 recombinant proteins were added to the Apo/LPL mixture (final concentrations of 80-100 nM). The Apo/LPL/ANGPTL3 protein mixtures were then added together with serially diluted anti-hANGPTL3 antibodies and incubated at room temperature for 30 minutes. Following the incubation, 100 μl of reconstituted lipase substrate, 1-trinitrophenyl-amino-dodecanoyl-2-pyrendecanoyl-3-0-hexadecyl-sn-glyeerol (LS-A, Progen), was added to 25 μl of the antibody mixture to a 96-well assay plate and incubated at 37° C. for two hours. Fluorescence was then measured at 342 nm/400 nm (excitation/emission) using a FLEXSTATION® 3 Microplate Reader (Molecular Devices, CA). Fluorescence is directly proportional to LPL activity.

Antibody H4H1276S exhibited inhibition of hANGPTL3's inhibitory activity against LPL. A full dose-response using the hANGPTL3 protein in the LPL assay was first performed to determine the ANGPTL3 $EC_{50}$ for each experiment, and $IC_{50}$ determinations for the antibody were then performed using constant concentrations of ANGPTL3 protein, as shown in Table 8. The antibody concentrations required for 50% maximum inhibition ($IC_{50}$) was determined to be 9.6 nM for 80 nM hANGPTL3(17-460)-His, 2.9 nM for 100 nM hANGPTL3(17-170)-His and 21 nM for 80 nM hANGPTL3(17-169)-mFc, respectively. Antibody concentrations ranged from 0 to 300 nM for testing human ANGPTL3 proteins.

Similarly, H4H1276S was tested in the LPL bioassay for its ability to inhibit cross-species orthologs: the cynomolgus monkey N-terminal region (amino acid residues 17-170 of SEQ ID NO:177) expressed with an C-terminal myc-myc-hexa-histidine tag [MfANGPTL3(17-170)-mmH; SEQ ID NO:167], the mouse ortholog N-terminal region amino acid residues 17-240 of SEQ ID NO:163 with a C-terminal hexa-histidine tag [mANGPTL3(17-240)-His; SEQ ID NO:166], and full-length mature ANGPTL3 from *Mus musculus* (i.e., amino acid residues 17-455 of SEQ ID NO:163) with a C-terminal decahistidine tag [mANGPTL3(17-455)-His; R&D Systems, MN; catalog #136-AN]. IC50s were determined to be 10 nM for 500 nM constant MfANGPTL3 (17-170)-mmH, 14 nM for 80 nM constant mANGPTL3 (17-455)-His, and 31 nM for 500 nM constant mANGPTL3 (17-240)-His. Antibody concentrations ranged from 0 to 600 nM for testing monkey and mouse ANGPTL3 proteins. The results are summarized in Table 9.

Antibodies against the N-terminal region of the homologous protein ANGPTL4 have also been shown to block the inhibitory function of ANGPTL4 on LPL (Lee et al., 2009, J. Biol. Chem. 284:13735-13745). Therefore, to evaluate possible cross-reactivity to ANGPTL4, the inhibitory anti-ANGPTL3 antibody H4H1276S was also tested against human ANGPTL4 in the LPL lipase assay, conducted as described above for the ANGPTL3 proteins. A recombinant form of the coiled-coil region of human ANGPTL4 (residues 26-148 of SEQ ID NO:164) with a C-terminal mouse IgG2a Fc fusion [hANGPTL4(26-148)-mFc, SEQ ID NO:178] exhibited an EC50 in the LPL assay of 0.2 nM (Table 9). H4H1276S, tested through a concentration range of 0-600 nM, did not block this inhibition (NB: Not bound; in Table 9).

of 47 nM [for hANGPTL3(17-169)-mFc] and 341 nM [for mANGPTL3(17-240)-His]. The following pairs, when added at final concentrations for each antibody of at least 200 nM, did not block the inhibition of LPL by either hANGPTL3(17-169)-mFc at 80 nM or mANGPTL3(17-240)-His at 500 nM: H1M896N+H4H1279P; H4H1250P+H4H1279P; H4H1248P+H4H1292P; and H4H1263S+H4H1292P. In this same assay, H4H1276S alone blocked these same constant concentrations of human and mouse ANGPTL3 with IC50s of 33 nM and 64 nM, respectively.

Example 7.1. In Vivo Effect of Anti-ANGPTL3 Antibody on Serum Lipid Levels

The effect of the anti-hANGPTL3 antibody H4H1726S on serum lipid levels was determined in C57Bl/6 mice. Mice were pre-bled 7 days before the experiment and put into groups of six mice each for each antibody dose tested. Antibodies were administered at 5 mg/kg (H4H1726S) and 10 mg/kg [H4H1726S and isotype-matched hIgG4(S108P) control with irrelevant specificity] dose levels by subcutaneous injection on day 0 of the study. Mice were bled after 4 hours of fasting at days 1, 4, 7 and 12 after antibody injections and serum lipid levels (triglycerides, total cholesterol, non-HDL cholesterol, LDL cholesterol and HDL cholesterol) were determined in the serum by an ADVIA® 1800 Chemistry System (Siemens). Averages were calculated for each of the time points for each antibody. Results, expressed as (mean±SEM) of serum lipid concentration, are shown in Tables 10-14.

TABLE 10

| Days after injection | Serum triglycerides (mg/dL) | | | | | |
|---|---|---|---|---|---|---|
| | Control Ab (10 mg/kg) | | H4H1276S (5 mg/kg) | | H4H1276S (10 mg/kg) | |
| | Mean | SEM | Mean | SEM | Mean | SEM |
| −7 | 87.83 | 6.18 | 89.83 | 3.65 | 87.17 | 5.062 |
| 1 | 123.16 | 7.02 | 68.00 | 2.84 | 53.83 | 2.52 |

TABLE 9

| | Human ANGPTL3 (17-460)-His | Human ANGPTL3 (17-170)-His | Human ANGPTL3 (17-169)-mFc | Monkey ANGPTL3 (17-170)-mmH | Mouse ANGPTL3 (17-455)-His | Mouse ANGPTL3 (17-240)-His | Human ANGPTL4 (26-148)-mFc |
|---|---|---|---|---|---|---|---|
| $EC_{50}$ (nM) | 50 | 91 | 16 | 625 | 33 | 199 | 0.2 |
| Constant ANGPTL3 or 4 (nM) | 80 | 100 | 80 | 500 | 80 | 500 | 2 |
| $IC_{50}$ H4H 1276S (nM) | 9.6 | 2.9 | 21 | 10 | 14 | 31 | NB |
| IgG4 cont. | NB | NB | NB | NB | NB | NB | NB |

As shown above, H4H1276S inhibited human ANGPTL3 (full-length and N-terminal), monkey ANGPTL3 (N-terminal) protein and mouse ANGPTL3 (full-length and N-terminal) activity at comparable degrees with an $IC_{50}$ range of about 3-31 nM.

A subset of antibodies were also tested to determine if combinations of two ANGPTL3 non-blocking antibodies added simultaneously could block the LPL inhibitory activity of ANGPTL3. Pairs of antibodies were tested for inhibiting the N-terminal domains of both human and mouse ANGPTL3, i.e., hANGPTL3(17-169)-mFc and mANGPTL3(17-240)-His, respectively. For this assay, the ANGPTL3 proteins exhibited IC50 values for blocking LPL TABLE 10-continued

| Days after injection | Serum triglycerides (mg/dL) | | | | | |
|---|---|---|---|---|---|---|
| | Control Ab (10 mg/kg) | | H4H1276S (5 mg/kg) | | H4H1276S (10 mg/kg) | |
| | Mean | SEM | Mean | SEM | Mean | SEM |
| 4 | 99.66 | 10.15 | 62.16 | 5.82 | 50.67 | 3.51 |
| 7 | 99.83 | 4.57 | 55.83 | 4.95 | 39.67 | 2.55 |
| 12 | 82.00 | 5.75 | 76.83 | 10.56 | 53.00 | 6.51 |

TABLE 11

| | Total cholesterol (mg/dL) | | | | | |
|---|---|---|---|---|---|---|
| Days after | Control Ab (10 mg/kg) | | H4H1276S (5 mg/kg) | | H4H1276S (10 mg/kg) | |
| injection | Mean | SEM | Mean | SEM | Mean | SEM |
| −7 | 82.50 | 2.11 | 80.33 | 1.15 | 81.33 | 2.14 |
| 1 | 87.83 | 1.87 | 71.50 | 5.48 | 63.67 | 3.38 |
| 4 | 75.00 | 2.58 | 59.50 | 3.51 | 51.00 | 2.98 |
| 7 | 83.50 | 1.77 | 67.00 | 1.79 | 61.33 | 2.33 |
| 12 | 87.83 | 1.82 | 83.00 | 4.30 | 69.33 | 3.22 |

TABLE 12

| | Non-HDL cholesterol (mg/dL) | | | | | |
|---|---|---|---|---|---|---|
| Days after | Control Ab (10 mg/kg) | | H4H1276S (5 mg/kg) | | H4H1276S (10 mg/kg) | |
| injection | Mean | SEM | Mean | SEM | Mean | SEM |
| −7 | 41.18 | 0.75 | 38.78 | 0.81 | 40.23 | 1.18 |
| 1 | 42.18 | 0.55 | 35.75 | 3.05 | 32.70 | 1.94 |
| 4 | 36.40 | 1.04 | 29.63 | 2.16 | 27.55 | 1.78 |
| 7 | 40.82 | 0.75 | 34.67 | 1.83 | 32.02 | 1.68 |
| 12 | 41.72 | 0.87 | 39.85 | 2.21 | 35.13 | 1.47 |

TABLE 13

| | LDL cholesterol (mg/dL) | | | | | |
|---|---|---|---|---|---|---|
| Days after | Control Ab (10 mg/kg) | | H4H1276S (5 mg/kg) | | H4H1276S (10 mg/kg) | |
| injection | Mean | SEM | Mean | SEM | Mean | SEM |
| −7 | 4.68 | 0.35 | 4.40 | 0.34 | 4.47 | 0.21 |
| 1 | 5.40 | 0.41 | 5.20 | 0.79 | 5.33 | 0.71 |
| 4 | 4.80 | 0.45 | 4.88 | 0.67 | 5.33 | 0.73 |
| 7 | 5.38 | 0.46 | 5.83 | 0.48 | 6.40 | 0.67 |
| 12 | 5.67 | 0.59 | 6.12 | 0.65 | 5.35 | 0.48 |

TABLE 14

| | HDL cholesterol (mg/dL) | | | | | |
|---|---|---|---|---|---|---|
| Days after | Control Ab (10 mg/kg) | | H4H1276S (5 mg/kg) | | H4H1276S (10 mg/kg) | |
| injection | Mean | SEM | Mean | SEM | Mean | SEM |
| −7 | 41.32 | 1.57 | 41.55 | 0.90 | 41.10 | 1.37 |
| 1 | 45.65 | 1.85 | 35.75 | 2.54 | 30.97 | 2.13 |
| 4 | 38.60 | 2.26 | 29.87 | 1.62 | 23.45 | 1.66 |
| 7 | 42.68 | 1.81 | 32.33 | 1.25 | 29.32 | 1.72 |
| 12 | 46.12 | 1.94 | 43.15 | 2.52 | 34.20 | 1.99 |

Levels of circulating H4H1726S (Serum Ab) were also determined using a standard ELISA assay. Briefly, plates were coated with a goat anti-human Fc antibody (Sigma-Aldrich) to capture Serum Ab. Serum was then added to the plates and captured human antibody was detected by chemiluminescence using a horseradish peroxidase (HRP) conjugated goat anti-human IgG antibody (Sigma-Aldrich). Results, expressed as (mean±SEM) of are shown in Table 15. Control: Mice that received an isotype-matched Control Ab.

TABLE 15

| | Serum Ab (μg/mL) | | | | | |
|---|---|---|---|---|---|---|
| Days after | Control Ab (10 mg/kg) | | H4H1276S (5 mg/kg) | | H4H1276S (10 mg/kg) | |
| injection | Mean | SEM | Mean | SEM | Mean | SEM |
| 1 | 65.00 | 8.05 | 36.38 | 7.57 | 126.23 | 9.96 |
| 4 | 59.16 | 4.94 | 29.91 | 4.32 | 86.28 | 6.77 |
| 7 | 58.23 | 6.02 | 30.86 | 5.11 | 54.24 | 8.96 |
| 12 | 41.35 | 9.76 | 5.48 | 1.79 | 39.04 | 7.08 |

Single administration of H4H1276S to C57Bl/6 mice at 10 mg/kg led to ~60% reduction in circulating triglycerides 7 days after the antibody administration (compared to isotype control). The administration of H4H1276S also led to a significant reduction in total cholesterol, non-HDL cholesterol and HDL cholesterol and had no effect on LDL cholesterol. A reduction in lipid levels was also observed, but less pronounced, at the 5 mg/kg compared to 10 mg/kg dose levels; e.g., serum triglycerides were reduced by 44% (compared to isotype control) 7 days after antibody administration.

Example 7.2. In Vivo Effect of Anti-ANGPTL3 Antibodies on Serum Lipid Levels

The evaluation of the in vivo effects of anti-hANGPTL3 antibodies H4H1276S and comparator antibody 4.9.1 on serum lipid levels was conducted in C57Bl/6 mice. Antibody 4.9.1 was prepared based on the amino acid sequences of SEQ ID No: 24 (VH) and SEQ ID No: 32 (VL) as disclosed in US Patent Application Publication No. 2008/0177045 and as a mouse IgG1 isotype. Mice were pre-bled 7 days before the experiment and put into groups of six mice per group. Antibodies H4H1276S, 4.9.1, and isotype-matched negative controls (human IgG4 and mouse IgG1, respectively) with irrelevant specificity were administered at 10 mg/kg dose by subcutaneous injection on day 0 of the study. Mice were bled after 4 hours of fasting at days 1, 7, 11 and 20 after injection of antibodies, and serum lipids levels (triglycerides, total cholesterol, non-HDL cholesterol, LDL cholesterol and HDL cholesterol) were determined in the serum using an ADVIA® 1800 Chemistry System (Siemens). Average lipid concentrations were calculated for each of the time point for each antibody. Results, expressed as (mean±SEM) of serum lipid concentration, are shown in Tables 16-20.

TABLE 16

| | Serum triglycerides (mg/dL) | | | | | | | |
|---|---|---|---|---|---|---|---|---|
| Days after | Control (IgG4) | | H4H1276S | | Control (IgG1) | | 4.9.1 | |
| injection | Mean | SEM | Mean | SEM | Mean | SEM | Mean | SEM |
| −7 | 109.16 | 9.05 | 109.16 | 6.44 | 112.80 | 6.87 | 109.17 | 7.24 |
| 1 | 81.67 | 6.76 | 46.00 | 3.59 | 95.20 | 8.92 | 41.83 | 2.42 |
| 7 | 95.67 | 5.42 | 49.67 | 3.86 | 101.80 | 7.55 | 96.00 | 3.70 |

TABLE 16-continued

| | Serum triglycerides (mg/dL) | | | | | | | |
|---|---|---|---|---|---|---|---|---|
| Days after | Control (IgG4) | | H4H1276S | | Control (IgG1) | | 4.9.1 | |
| injection | Mean | SEM | Mean | SEM | Mean | SEM | Mean | SEM |
| 11 | 100.83 | 6.20 | 51.00 | 5.89 | 117.00 | 6.00 | 92.00 | 4.50 |
| 20 | 82.17 | 4.36 | 72.67 | 3.47 | 79.40 | 6.59 | 73.83 | 5.03 |

TABLE 17

| | Total cholesterol (mg/dL) | | | | | | | |
|---|---|---|---|---|---|---|---|---|
| Days after | Control (IgG4) | | H4H1276S | | Control (IgG1) | | 4.9.1 | |
| injection | Mean | SEM | Mean | SEM | Mean | SEM | Mean | SEM |
| −7 | 80.81 | 0.95 | 80.92 | 3.05 | 80.32 | 2.84 | 79.37 | 2.76 |
| 1 | 82.82 | 2.11 | 67.33 | 3.60 | 82.98 | 2.17 | 71.35 | 1.82 |
| 7 | 79.20 | 1.81 | 63.58 | 3.98 | 85.02 | 7.27 | 82.07 | 4.36 |
| 11 | 89.97 | 3.18 | 69.02 | 2.11 | 83.92 | 2.49 | 84.58 | 1.08 |
| 20 | 92.43 | 1.10 | 80.17 | 3.20 | 87.47 | 2.58 | 88.40 | 2.84 |

TABLE 18

| | Non-HDL cholesterol (mg/dL) | | | | | | | |
|---|---|---|---|---|---|---|---|---|
| Days after | Control (IgG4) | | H4H1276S | | Control (IgG1) | | 4.9.1 | |
| injection | Mean | SEM | Mean | SEM | Mean | SEM | Mean | SEM |
| −7 | 42.44 | 1.18 | 42.87 | 1.03 | 43.20 | 2.44 | 41.73 | 1.40 |
| 1 | 40.85 | 1.48 | 35.33 | 1.79 | 40.68 | 0.87 | 36.97 | 1.49 |
| 7 | 39.03 | 1.04 | 33.72 | 2.86 | 43.30 | 4.35 | 40.47 | 2.35 |
| 11 | 44.68 | 1.93 | 35.18 | 1.64 | 40.28 | 0.95 | 41.38 | 1.05 |
| 20 | 47.40 | 0.67 | 42.10 | 1.51 | 44.72 | 1.66 | 44.40 | 1.57 |

TABLE 19

| | LDL cholesterol (mg/dL) | | | | | | | |
|---|---|---|---|---|---|---|---|---|
| Days after | Control (IgG4) | | H4H1276S | | Control (IgG1) | | 4.9.1 | |
| injection | Mean | SEM | Mean | SEM | Mean | SEM | Mean | SEM |
| −7 | 3.93 | 0.07 | 4.20 | 0.26 | 4.38 | 0.26 | 4.20 | 0.18 |
| 1 | 3.95 | 0.28 | 4.25 | 0.37 | 3.92 | 0.17 | 4.62 | 0.37 |
| 7 | 3.75 | 0.14 | 5.25 | 1.08 | 5.76 | 1.61 | 4.57 | 0.73 |
| 11 | 5.05 | 0.26 | 5.47 | 0.23 | 4.88 | 0.27 | 4.78 | 0.23 |
| 20 | 5.72 | 0.34 | 4.95 | 0.32 | 4.97 | 0.28 | 5.65 | 0.46 |

TABLE 20

| | HDL cholesterol (mg/dL) | | | | | | | |
|---|---|---|---|---|---|---|---|---|
| Days after | Control (IgG4) | | H4H1276S | | Control (IgG1) | | 4.9.1 | |
| injection | Mean | SEM | Mean | SEM | Mean | SEM | Mean | SEM |
| −7 | 38.37 | 0.95 | 38.00 | 2.27 | 37.12 | 1.88 | 37.63 | 1.52 |
| 1 | 41.97 | 1.32 | 32.00 | 1.89 | 42.30 | 2.09 | 34.38 | 0.85 |
| 7 | 40.17 | 0.93 | 29.87 | 1.23 | 41.72 | 2.97 | 41.60 | 2.47 |
| 11 | 45.28 | 1.80 | 33.83 | 1.15 | 43.64 | 1.70 | 43.20 | 1.57 |
| 20 | 45.03 | 0.75 | 38.07 | 1.79 | 42.75 | 1.69 | 44.00 | 1.83 |

A single 10 mg/kg dose of H4H1276S in C57Bl/6 mice resulted in reduction of plasma triglyceride levels compared to isotype control on days 1, 7, 11 and 20 after antibody injection; and this effect was more sustained compared to a single treatment at the same dose level with the comparator 4.9.1 (Table 16). Administration of H4H1276S also led to a reduction in total cholesterol (Table 17) and HDL cholesterol (Table 20) in C57Bl/6 mice.

Example 8. In Vivo Effect of H4H1276S on Serum Lipid Levels in Hyperlipidemic ApoE$^{-/-}$ Mice The effect of anti-hANGPTL3 antibody H4H1276S on serum lipids levels was determined in apoE$^{-/-}$ mice. These mice are hyperlipidemic with the majority of their circulating cholesterol found in the form of VLDL and LDL. Mice were pre-bled 7 days before the experiment and put into groups of six mice per group. The antibodies, H4H1276S and an isotype-matched (hIgG4) control with irrelevant specificity, were administered at 10 mg/kg dose by subcutaneous injection on day 0 of the study. Mice were bled after 4 hours of fasting at days 1, 4, 7 and 11 after injection of antibodies; and serum lipids levels (triglycerides, total cholesterol, non-HDL cholesterol, LDL cholesterol and HDL cholesterol) were determined in the serum using an ADVIA® 1800 Chemistry System (Siemens). Average lipid concentrations were calculated for each of the time points for each antibody-treated group. Results, expressed as (mean±SEM) of serum lipid concentration, are shown in Tables 21-25.

TABLE 21

| | Serum triglycerides (mg/dL) | | | |
|---|---|---|---|---|
| Days after | Control (hIgG4) | | H4H1276S | |
| injection | Mean | SEM | Mean | SEM |
| −7 | 134.17 | 11.81 | 141.67 | 17.14 |
| 1 | 156.33 | 19.06 | 61.33 | 3.66 |
| 4 | 181.00 | 7.70 | 70.50 | 4.46 |
| 7 | 190.67 | 27.65 | 52.50 | 6.22 |
| 11 | 170.00 | 28.85 | 133.00 | 13.56 |

TABLE 22

| | Total cholesterol (mg/dL) | | | |
|---|---|---|---|---|
| Days after | Control (hIgG4) | | H4H1276S | |
| injection | Mean | SEM | Mean | SEM |
| −7 | 450.67 | 25.68 | 479.33 | 13.76 |
| 1 | 497.50 | 37.77 | 386.33 | 28.59 |
| 4 | 395.00 | 14.37 | 281.20 | 20.83 |
| 7 | 447.33 | 22.18 | 295.50 | 12.86 |
| 11 | 463.80 | 36.01 | 398.03 | 23.13 |

TABLE 23

| | Non-HDL cholesterol (mg/dL) | | | |
|---|---|---|---|---|
| Days after | Control (hIgG4) | | H4H1276S | |
| injection | Mean | SEM | Mean | SEM |
| −7 | 435.87 | 25.59 | 464.53 | 13.97 |
| 1 | 476.30 | 37.29 | 371.25 | 28.65 |
| 4 | 375.61 | 14.51 | 266.26 | 21.19 |
| 7 | 427.66 | 21.45 | 280.75 | 12.55 |
| 11 | 442.27 | 34.19 | 379.55 | 22.31 |

TABLE 24

| | LDL cholesterol (mg/dL) | | | |
|---|---|---|---|---|
| Days after | Control (hIgG4) | | H4H1276S | |
| injection | Mean | SEM | Mean | SEM |
| −7 | 14.27 | 1.63 | 14.87 | 0.90 |
| 1 | 17.42 | 2.94 | 11.23 | 1.81 |
| 4 | 10.28 | 1.52 | 6.62 | 0.83 |
| 7 | 11.82 | 1.40 | 6.32 | 0.45 |
| 11 | 13.90 | 2.54 | 10.21 | 1.14 |

TABLE 25

| | HDL cholesterol (mg/dL) | | | |
|---|---|---|---|---|
| Days after | Control (hIgG4) | | H4H1276S | |
| injection | Mean | SEM | Mean | SEM |
| −7 | 14.80 | 0.37 | 14.80 | 0.54 |
| 1 | 21.20 | 1.00 | 15.08 | 0.53 |
| 4 | 19.33 | 0.94 | 14.53 | 0.75 |
| 7 | 19.77 | 0.78 | 14.58 | 0.72 |
| 11 | 21.53 | 1.89 | 18.48 | 1.00 |

Single administration of H4H1276S to apoE$^{-/-}$ mice at 10 mg/kg led to ~72% (mean) reduction in circulating triglycerides (Table 21) and ~46% (mean) reduction in LDL cholesterol (Table 24) 7 days after the antibody administration (compared to the isotype-matched control Ab, i.e., hIgG4). The administration of H4H1276S also led to a reduction in total cholesterol (Table 22) and non-HDL cholesterol (Table 23).

Levels of circulating H4H1276S (Serum Ab) were also determined using a standard ELISA assay. Briefly, plates were coated with a goat anti-human Fc antibody (Sigma-Aldrich) to capture Serum Ab. Serum was then added to the plates and captured antibodies were detected by chemiluminescence using a horseradish peroxidase (HRP) conjugated goat anti-human IgG antibody (Sigma-Aldrich). Results, expressed as (mean±SEM), are shown in Table 26 (Control: mice that received an isotype-matched control Ab, i.e., hIgG4).

TABLE 26

| | Serum Ab (µg/mL) | | | |
|---|---|---|---|---|
| Days after | Control (hIgG4) (10 mg/kg) | | H4H1276S (10 mg/kg) | |
| injection | Mean | SEM | Mean | SEM |
| 1 | 89.98 | 16.70 | 115.29 | 19.75 |
| 4 | 67.18 | 2.38 | 86.61 | 5.32 |

TABLE 26-continued

| | Serum Ab (µg/mL) | | | |
|---|---|---|---|---|
| Days after | Control (hIgG4) (10 mg/kg) | | H4H1276S (10 mg/kg) | |
| injection | Mean | SEM | Mean | SEM |
| 7 | 58.52 | 2.00 | 39.85 | 6.91 |
| 12 | 43.26 | 1.76 | 3.18 | 2.64 |

Example 9. In Vivo Effect of H4H1276S on Circulating Lipid Levels in Hyperlipidemic Ldlr$^{-/-}$ Mice The effect of the anti-hANGPTL3 antibody H4H1726S on serum lipid levels was determined in Ldlr$^{-/-}$ mice. These mice are hyperlipemic with a majority of circulating cholesterol found in the form of LDL due to the lack of LDLR, the major receptor for LDL cholesterol uptake.

Mice were pre-bled 7 days before the experiment and put into groups of six mice. The antibodies, H4H1726S and isotype-matched (hIgG4) negative control, were administered at 10 mg/kg dose by subcutaneous injection on day 0 of the study. Mice were bled after 4 hours of fasting at days 1, 4, 7 and 11 after antibody injection and serum lipids levels (triglycerides, total cholesterol, non-HDL cholesterol, LDL cholesterol and HDL cholesterol) were determined using an ADVIA® 1800 Chemistry System (Siemens) clinical chemistry analyzer. Averages were calculated for each time point for each antibody. Results, expressed as (mean±SEM) of serum lipids concentration (triglycerides, total cholesterol, non-HDL cholesterol, LDL cholesterol and HDL cholesterol), are shown in Tables 27-31, respectively. (Control=mice that received an isotype-matched control antibody).

TABLE 27

| | Serum triglycerides (mg/dL) | | | |
|---|---|---|---|---|
| | Antibody | | | |
| Days after | Control (10 mg/kg) | | H4H1726S (10 mg/kg) | |
| injection | Mean | SEM | Mean | SEM |
| −7 | 114.50 | 11.08 | 110.83 | 6.89 |
| 1 | 131.50 | 6.18 | 74.17 | 3.30 |
| 4 | 112.67 | 8.94 | 68.00 | 3.91 |
| 7 | 136.67 | 11.55 | 92.67 | 12.16 |
| 11 | 142.33 | 7.10 | 95.83 | 8.67 |

TABLE 28

| | Total cholesterol (mg/dL) | | | |
|---|---|---|---|---|
| | Antibody | | | |
| Days after | Control (10 mg/kg) | | H4H1726S (10 mg/kg) | |
| injection | Mean | SEM | Mean | SEM |
| −7 | 237.95 | 7.33 | 236.99 | 5.68 |
| 1 | 241.97 | 10.58 | 206.98 | 9.68 |
| 4 | 229.88 | 7.61 | 172.96 | 4.49 |
| 7 | 234.74 | 10.49 | 176.28 | 7.47 |
| 11 | 251.87 | 18.82 | 201.73 | 10.12 |

TABLE 29

Non-HDL cholesterol (mg/dL)

| Days after injection | Antibody | | | |
|---|---|---|---|---|
| | Control (10 mg/kg) | | H4H1726S (10 mg/kg) | |
| | Mean | SEM | Mean | SEM |
| −7 | 180.81 | 7.47 | 182.79 | 5.93 |
| 1 | 184.35 | 10.22 | 155.93 | 8.74 |
| 4 | 175.13 | 7.26 | 130.79 | 4.66 |
| 7 | 174.84 | 9.26 | 126.56 | 6.63 |
| 11 | 190.00 | 17.07 | 145.43 | 7.34 |

TABLE 30

LDL cholesterol (mg/dL)

| Days after injection | Antibody | | | |
|---|---|---|---|---|
| | Control (10 mg/kg) | | H4H1726S (10 mg/kg) | |
| | Mean | SEM | Mean | SEM |
| −7 | 62.75 | 2.18 | 62.75 | 1.81 |
| 1 | 63.25 | 2.40 | 53.82 | 4.09 |
| 4 | 60.97 | 3.14 | 49.65 | 2.72 |
| 7 | 59.52 | 2.99 | 46.05 | 2.13 |
| 11 | 63.23 | 3.07 | 54.28 | 1.67 |

TABLE 31

HDL cholesterol (mg/dL)

| Days after injection | Antibody | | | |
|---|---|---|---|---|
| | Control (10 mg/kg) | | H4H1726S (10 mg/kg) | |
| | Mean | SEM | Mean | SEM |
| −7 | 57.13 | 1.56 | 54.20 | 1.89 |
| 1 | 57.62 | 0.88 | 51.05 | 0.98 |
| 4 | 54.75 | 2.23 | 42.17 | 1.89 |
| 7 | 59.90 | 2.51 | 49.72 | 2.35 |
| 11 | 61.87 | 2.48 | 56.30 | 3.43 |

As shown in Tables 27-31, administration of H4H1726S to Ldlr$^{-/-}$ mice led to a significant reduction in plasma triglycerides with a maximal observed reduction of 44% (based on mean values). Significant reductions in LDL cholesterol (up to 23%), as well as total cholesterol, non-HDL cholesterol and HDL cholesterol, were also observed in H4H1726S-treated subjects. Reduction of LDL cholesterol in mice deficient for the major receptor for LDL cholesterol uptake (LDLR) suggests an LDLR-independent mechanism for LDL cholesterol reduction by ANGPTL3 inhibition.

Levels of circulating H4H1726S (Serum Ab) were also determined using a standard ELISA assay. Briefly, plates were coated with a goat anti-human Fc antibody (Sigma-Aldrich) to capture Serum Ab. Serum was then added to the plates and captured antibodies were detected by chemiluminescence using a horseradish peroxidase (HRP) conjugated goat anti-human IgG antibody (Sigma-Aldrich). Results, expressed as (mean±SEM) of are shown in Table 32. (Control=mice that received an isotype-matched control antibody).

TABLE 32

Serum Ab (µg/mL)

| Days after injection | Antibody | | | |
|---|---|---|---|---|
| | Control (10 mg/kg) | | H4H1726S (10 mg/kg) | |
| | Mean | SEM | Mean | SEM |
| 1 | 44.59 | 1.95 | 58.79 | 5.95 |
| 4 | 42.28 | 6.12 | 47.21 | 10.24 |
| 7 | 41.76 | 3.87 | 28.88 | 5.97 |
| 11 | 37.25 | 6.85 | 21.02 | 4.86 |

As shown in Table 32, serum levels of H4H1726S decreased to about 21 µg/mL by day 11 following injection of mice with 10 mg/kg of antibody.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

The invention claimed is:

1. A method for preventing or treating a disease or disorder which is prevented, ameliorated, improved or inhibited by reduction or inhibition of ANGPTL3 activity, the method comprising administering to a subject in need thereof a therapeutically effective amount of a pharmaceutical composition comprising an isolated human antibody or antigen-binding fragment thereof that specifically binds human angiopoietin-like protein 3 (hANGPTL3) of SEQ ID NO:161 and neutralizes, reduces, or interferes with at least one activity of hANGPTL3, and a pharmaceutically acceptable carrier, wherein the antibody or antigen-binding fragment comprises a heavy chain complementarity determining region HCDR1/HCDR2/HCDR3 sequence combination comprising SEQ ID NO: 68/70/72; and a light chain complementarity determining region LCDR1/LCDR2/LCDR3 sequence combination comprising SEQ ID NO: 76/78/80, wherein the disease or disorder is hypertriglyceridemia.

2. The method of claim 1, further comprising administering to the subject one or more additional therapeutic agents selected from the group consisting of an inhibitor of HMG-CoA reductase; an inhibitor of cholesterol uptake or bile acid re-absorption, or both; an agent which increases lipoprotein catabolism; and an activator of the LXR transcription factor.

3. The method of claim 1, further comprising administering to the subject one or more additional therapeutic agents selected from the group consisting of a statin, niacin, fibrate, anti-hANGPTL4 antibody and anti-PCSK9 antibody.

4. The method of claim 1, wherein the fragment is a single chain antibody, an Fab, or an F(ab')$_2$.

5. The method of claim 1, wherein the antibody or antigen-binding fragment thereof comprises a heavy chain variable region/light chain variable region (HCVR/LCVR) pair comprising SEQ ID NO:66/74.

* * * * *